United States Patent
Funahashi et al.

(10) Patent No.: US 11,616,200 B2
(45) Date of Patent: *Mar. 28, 2023

(54) COMPOUND, MATERIAL FOR ORGANIC ELECTROLUMINESCENT ELEMENT, ORGANIC ELECTROLUMINESCENT ELEMENT, AND ELECTRONIC APPARATUS

(71) Applicant: IDEMITSU KOSAN CO., LTD., Tokyo (JP)

(72) Inventors: Masakazu Funahashi, Chiba (JP); Takahiro Fujiyama, Kisarazu (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,224

(22) Filed: Jun. 23, 2022

(65) Prior Publication Data

US 2022/0344590 A1 Oct. 27, 2022

Related U.S. Application Data

(63) Continuation of application No. 17/828,080, filed on May 31, 2022, which is a continuation of application No. 16/400,789, filed on May 1, 2019, now abandoned, which is a continuation of application No. 14/910,120, filed as application No. PCT/JP2015/055983 on Feb. 27, 2015, now abandoned.

(30) Foreign Application Priority Data

Feb. 28, 2014 (JP) ................. 2014-039015

(51) Int. Cl.
| | | |
|---|---|---|
| H01L 51/00 | (2006.01) | |
| C07D 333/76 | (2006.01) | |
| C07D 307/91 | (2006.01) | |
| C09K 11/06 | (2006.01) | |
| H01L 51/50 | (2006.01) | |

(52) U.S. Cl.
CPC .......... *H01L 51/006* (2013.01); *C07D 307/91* (2013.01); *C07D 333/76* (2013.01); *C09K 11/06* (2013.01); *H01L 51/0061* (2013.01); *H01L 51/0071* (2013.01); *H01L 51/0073* (2013.01); *H01L 51/0074* (2013.01); *C09K 2211/1007* (2013.01); *C09K 2211/1011* (2013.01); *C09K 2211/1088* (2013.01); *C09K 2211/1092* (2013.01); *H01L 51/0052* (2013.01); *H01L 51/0067* (2013.01); *H01L 51/0072* (2013.01); *H01L 51/5012* (2013.01); *H01L 51/5056* (2013.01); *H01L 51/5064* (2013.01)

(58) Field of Classification Search
CPC ............... H01L 51/006; H01L 51/0061; H01L 51/0071; H01L 51/0073; H01L 51/0074
See application file for complete search history.

(56) References Cited

U.S. PATENT DOCUMENTS

| | | |
|---|---|---|
| 2010/0001636 A1 | 1/2010 | Yabunouchi |
| 2011/0084258 A1 | 4/2011 | Kim et al. |
| 2011/0215308 A1 | 9/2011 | Im et al. |

(Continued)

FOREIGN PATENT DOCUMENTS

| | | |
|---|---|---|
| CN | 103108859 A | 5/2013 |
| CN | 105683150 A | 6/2016 |

(Continued)

OTHER PUBLICATIONS

Office Action dated Jun. 3, 2022, in corresponding Korean Patent Application No. 2022-7016168, (with English-language Translation).

(Continued)

*Primary Examiner* — Anthony Ho
(74) *Attorney, Agent, or Firm* — Oblon, McClelland, Maier & Neustadt, L.L.P.

(57) ABSTRACT

A compound represented by formula (1):

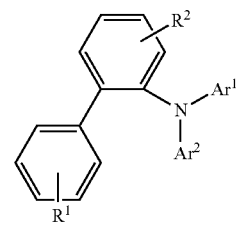

wherein $Ar^1$ and $Ar^2$ each represents a group represented by formula (3);

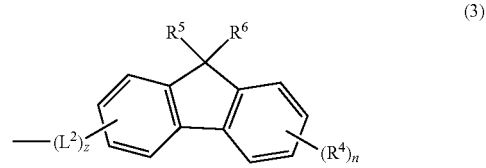

and $R^1$ represents a naphthylphenyl group, a biphenylyl group, a terphenylyl group, a biphenylenyl group, a naphthyl group, or a phenylnaphthyl group; $R^2$ represents a hydrogen atom; $R^5$ and $R^6$ are as defined in the description is provided. An electroluminescence device which contains the compound of formula (1) is also provided.

30 Claims, No Drawings

(56) References Cited

U.S. PATENT DOCUMENTS

| | | |
|---|---|---|
| 2011/0278551 A1 | 11/2011 | Yabunouchi |
| 2012/0043533 A1 | 2/2012 | Mizuki et al. |
| 2012/0112169 A1 | 5/2012 | Mizuki et al. |
| 2012/0258426 A1 | 10/2012 | Kato |
| 2012/0326137 A1 | 12/2012 | Song et al. |
| 2013/0001528 A1 | 1/2013 | Chang et al. |
| 2013/0153878 A1 | 6/2013 | Mizuki et al. |
| 2013/0207046 A1 | 8/2013 | Pflumm et al. |
| 2013/0293579 A1 | 11/2013 | Wu et al. |
| 2014/0167003 A1 | 6/2014 | Kato et al. |
| 2014/0312340 A1 | 10/2014 | Funahashi et al. |
| 2014/0326961 A1 | 11/2014 | Han et al. |
| 2014/0346482 A1 | 11/2014 | Mizuki et al. |
| 2014/0353646 A1 | 12/2014 | Mizuki et al. |
| 2014/0374720 A1 | 12/2014 | Kato et al. |
| 2015/0115239 A1 | 4/2015 | Pflumm et al. |
| 2015/0179953 A1 | 6/2015 | Mujica-Fernaud et al. |
| 2015/0207075 A1 | 7/2015 | Mujica-Fernaud et al. |
| 2015/0243891 A1 | 8/2015 | Kato et al. |
| 2015/0263292 A1 | 9/2015 | Kato et al. |
| 2015/0364692 A1 | 12/2015 | Kawamura et al. |
| 2016/0181526 A1 | 6/2016 | Kato et al. |
| 2017/0025619 A1 | 1/2017 | Kim et al. |
| 2019/0088886 A1 | 3/2019 | Ogita et al. |

FOREIGN PATENT DOCUMENTS

| | | |
|---|---|---|
| DE | 10 2010 045 405 A1 | 3/2012 |
| EP | 2 891 648 A1 | 7/2015 |
| EP | 2 891 653 A1 | 7/2015 |
| JP | 11-144875 | 5/1999 |
| JP | 2095-44791 A | 2/2005 |
| JP | 2010-37312 A | 2/2010 |
| KR | 10-2011-0011647 | 2/2011 |
| KR | 10-2011-0015213 | 2/2011 |
| KR | 10-2012-0072320 | 7/2012 |
| KR | 10-2016-0143627 A | 12/2016 |
| KR | 10-2404303 | 5/2022 |
| WO | WO 2009/145016 A1 | 12/2003 |
| WO | WO 2007/125714 A1 | 11/2007 |
| WO | 2010/044130 A1 | 4/2010 |
| WO | 2010/122610 A1 | 10/2010 |
| WO | WO 2011/021520 A1 | 2/2011 |
| WO | 2012/034627 A1 | 3/2012 |
| WO | 2013/039184 A1 | 3/2013 |
| WO | 2013/039221 A1 | 3/2013 |
| WO | 2013/042775 A1 | 3/2013 |
| WO | 2013/077385 A1 | 5/2013 |
| WO | 2013/087142 A1 | 6/2013 |
| WO | WO 2013/135352 | 9/2013 |
| WO | WO 2013/135352 A1 | 9/2013 |
| WO | 2014/015935 A2 | 1/2014 |
| WO | 2014/015938 A1 | 1/2014 |
| WO | WO 2014/015937 A1 | 1/2014 |
| WO | WO 2014/034795 A1 | 3/2014 |
| WO | 2014/072017 A | 5/2014 |
| WO | 2014/129764 A1 | 8/2014 |
| WO | 2015/000549 A1 | 1/2015 |
| WO | 2015/004875 A1 | 1/2015 |
| WO | 2015/022051 A1 | 2/2015 |

OTHER PUBLICATIONS

International Search Report dated May 12, 2015 in PCT/JP15/55983 Filed Feb. 27, 2015.
Extended European Setarch Report dated Oct. 4, 2017 in Patent Application No. 15756019.4.
Combined Chinese Office Action and Search Report dated Mar. 28, 2018 in corresponding Patent Application No. 201580001551.2 (with English Translation of Category of Cited Documents), 7 pages.
Office Action dated May 29, 2018 in corresponding Japanese Patent Application No. 2017-037575 (with English Translation), 11 pages.
Office Action dated Mar. 11, 2019, in the corresponding Chinese patent application with machine translation.
Office Action dated Mar. 10, 2021 in corresponding European Patent Application No. 15 756 019.4, 6 pages.
Office Action dated Jul. 1, 2021, in corresponding Korean Patent Application No. 10-2016-7003056 (with English-language Translation).
Office Action dated Sep. 13, 2022. in corresponding Chinese Patent Application No. 201910439899.X.

COMPOUND, MATERIAL FOR ORGANIC ELECTROLUMINESCENT ELEMENT, ORGANIC ELECTROLUMINESCENT ELEMENT, AND ELECTRONIC APPARATUS

CROSS REFERENCE TO RELATED APPLICATIONS

This application is a continuation application of prior U.S. application Ser. No. 17/828,080, filed May 31, 2022, the disclosure of which is incorporated herein by reference in its entirety. U.S. application Ser. No. 17,828,080 is a continuation application of prior U.S. application Ser. No. 16/400,789, filed May 1, 2019, the disclosure of which is incorporated herein by reference in its entirety. U.S. application Ser. No. 16/400,789 is a continuation application of prior U.S. application Ser. No. 14/910,120, filed Feb. 4, 2016, the disclosure of which is incorporated herein by reference in its entirety. U.S. application Ser. No. 14/910,120 is the national stage of PCT/JP2015/055983, filed Feb. 27, 2015, the disclosure of which is incorporated herein by reference in its entirety. U.S. application Ser. No. 14/910,120 claims priority to Japanese Application No. 2014-039015, filed Feb. 28, 2014, the disclosure of which is incorporated herein by reference in its entirety.

TECHNICAL FIELD

The present invention relates to compounds, materials for organic electroluminescence devices comprising the compounds, organic electroluminescence devices comprising the compounds, and electronic equipment comprising the organic electroluminescence device.

BACKGROUND ART

An organic electroluminescence (EL) device is generally composed of an anode, a cathode, and one or more organic thin film layers which are sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, the development of a compound which transports electrons or holes into a light emitting region efficiently and facilitates the recombination of electrons and holes is important to obtain a high efficiency organic EL device.

The drive of an organic EL device at lower voltage is effective for reducing the power consumption and also effective for improving the emission efficiency and the device lifetime. To reduce the driving voltage, a charge transporting material having a high electron mobility and/or a high hole mobility is required.

Patent Literatures 1 to 4 disclose amine compounds having a fluorene structure, a dibenzofuran structure and an aryl group. However, the proposed amine compounds are insufficient in the hole mobility. Therefore, a compound having a higher hole mobility has been sill required.

CITATION LIST

Patent Literature

Patent Literature 1: WO 2010/044130
Patent Literature 2: WO 2012/034627
Patent Literature 3: WO 2013/087142
Patent Literature 4: WO 2014/015938

SUMMARY OF INVENTION

Technical Problem

The present invention has been made to solve the above problem and an object of the invention is to provide an organic EL device which is capable of driving at a low voltage and has long lifetime and high emission efficiency and a material for organic EL devices which realize such an organic EL device.

Solution to Problem

As a result of extensive research in view of achieving the above object, the inventors have found that the compound represented by formula (1) has a high hole mobility and further found that an organic EL device which is capable of driving at a low voltage and has long lifetime and high emission efficiency is obtained by using such a compound.

In an aspect, the present invention provides a compound represented by formula (1) (also referred to as "compound (1)"):

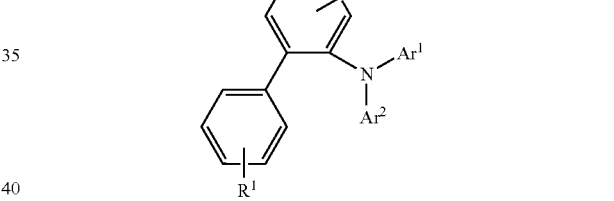

wherein one of $R^1$ and $R^2$ represents a substituted or unsubstituted aryl group having 6 to 50 ring carbon atoms and the other represents a hydrogen atom, a substituted or unsubstituted alkyl group having 1 to 20 carbon atoms, a substituted or unsubstituted heteroaryl group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group; or both $R^1$ and $R^2$ each independently represent a substituted or unsubstituted aryl group having 6 to 50 ring carbon atoms;

when one or both of $R^1$ and $R^2$ represent a substituted or unsubstituted aryl group having 6 to 50 ring carbon atoms, the aryl group and a benzene ring to which $R^1$ or $R^2$ is bonded may be crosslinked;

$Ar^1$ represents a group represented by formula (2) or (3);

$Ar^2$ represents a group selected from a group represented by formula (2), a group represented by formula (3), and a substituted or unsubstituted aryl group having 6 to 50 ring carbon atoms:

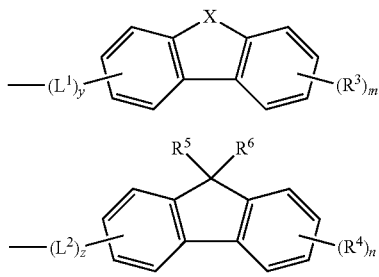

in formula (2):

X represents an oxygen atom or a sulfur atom;

$L^1$ represents a substituted or unsubstituted arylene group having 6 to 50 ring carbon atoms;

y represents 0 or 1, and when y is 0, $(L^1)_0$ represents a single bond;

$R^3$ represents a substituted or unsubstituted alkyl group having 1 to 20 carbon atoms, a substituted or unsubstituted aryl group having 6 to 50 ring carbon atoms, a substituted or unsubstituted heteroaryl group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group; and m represents an integer of 0 to 4, when m is an integer of 2 to 4, two to four groups $R^3$ may be the same or different and may be bonded to each other to form a ring, and when m is 0, $(R^3)_0$ represents a hydrogen atom; in formula (3):

$R^5$ and $R^6$ each independently represent a hydrogen atom, a substituted or unsubstituted alkyl group having 1 to 20 carbon atoms, a substituted or unsubstituted aryl group having 10 to 50 ring carbon atoms, a substituted or unsubstituted heteroaryl group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group;

$L^2$ represents a substituted or unsubstituted arylene group having 6 to 50 ring carbon atoms;

z represents 0 or 1, and when z is 0, $(L^2)_0$ represents a single bond;

$R^4$ represents a substituted or unsubstituted alkyl group having 1 to 20 carbon atoms, a substituted or unsubstituted aryl group having 6 to 50 ring carbon atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group;

n represents an integer of 0 to 4, when n is an integer of 2 to 4, two to four groups $R^4$ may be the same or different and may be bonded to each other to form a ring, and when n is 0, $(R^4)_0$ represents a hydrogen atom.

In another aspect, the present invention provides a material for organic EL devices which comprises the compound (1).

In still another aspect, the present invention provides an organic EL device which comprises an anode, a cathode, and at least one organic thin film layer between the anode and the cathode, wherein the at least one organic thin film layer comprises a light emitting layer and at least one layer of the at least one organic thin film layer comprises the compound (1).

In still another aspect, the present invention provides an electronic equipment which comprises the organic EL device mentioned above.

Advantageous Effects of Invention

An organic EL device which is capable of driving at a low voltage and has long lifetime and high emission efficiency is obtained by using the compound (1).

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each represents an integer of 1 or more.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optimal substituent referred to by "substituted or unsubstituted" used herein is, unless otherwise noted, at least one preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms which includes 1 to 5, preferably 1 to 3, more preferably 1 or 2 heteroatoms, wherein the heteroatoms are the same or different and selected from a nitrogen atom, an oxygen atom and a sulfur atom; a haloalkyl group having 1 to 50, preferably 1 to 18, more preferably 1 to 8 carbon atoms wherein one or more, preferably 1 to 15, more preferably 1 to 7 hydrogen atoms or all the hydrogen atoms are substituted with the same or different halogen atoms selected from a fluorine atom, a chlorine atom, a bromine atom, and a iodine atom; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

Of the above substituents, more preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a mono- or di-substituted amino group wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

The above optional substituent may further has the substituent mentioned above. The optional substituents may be bonded to each other to form a ring.

The "substituted or unsubstituted carbazolyl group" used herein includes the following carbazolyl groups:

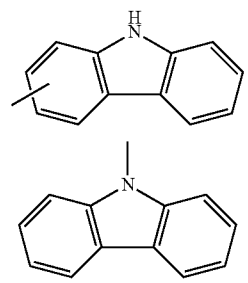

a substituted carbazolyl group having the optional substituent mentioned above, and the following substituted carbazolyl groups:

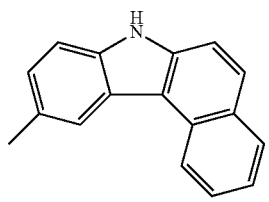

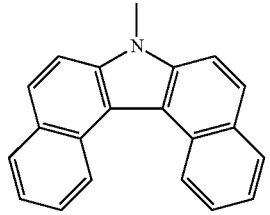

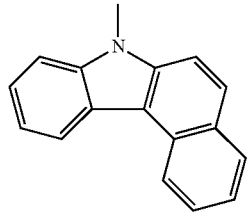

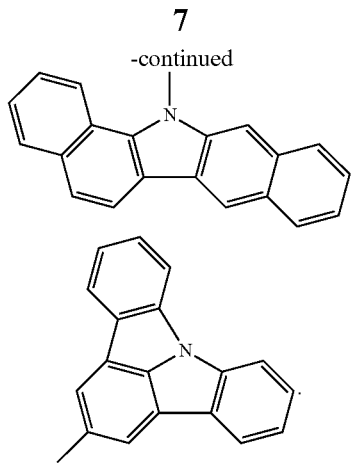

The compound (1) is represented by formula (1):

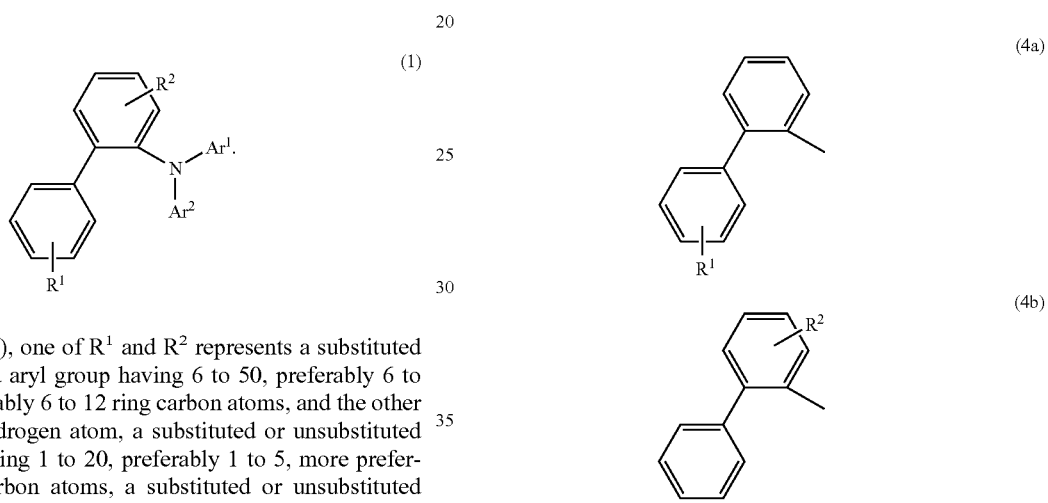

In formula (1), one of $R^1$ and $R^2$ represents a substituted or unsubstituted aryl group having 6 to 50, preferably 6 to 24, more preferably 6 to 12 ring carbon atoms, and the other represents a hydrogen atom, a substituted or unsubstituted alkyl group having 1 to 20, preferably 1 to 5, more preferably 1 to 4 carbon atoms, a substituted or unsubstituted heteroaryl group having 3 to 50, preferably 3 to 24, more preferably 3 to 12 ring atoms, a halogen atom, a substituted or unsubstituted fluoroalkyl group having 1 to 20, preferably 1 to 5, more preferably 1 to 4 carbon atoms, a substituted or unsubstituted alkoxy group having 1 to 20, preferably 1 to 5, more preferably 1 to 4 carbon atoms, a substituted or unsubstituted fluoroalkoxy group having 1 to 20, preferably 1 to 5, more preferably 1 to 4 carbon atoms, a substituted or unsubstituted aryloxy group having 6 to 50, preferably 6 to 24, more preferably 6 to 12 ring carbon atoms, or a cyano group; or both of $R^1$ and $R^2$ each independently represent a substituted or unsubstituted aryl group having 6 to 50 ring carbon atoms.

The other of $R^1$ and $R^2$ is preferably selected from a hydrogen atom, a substituted or unsubstituted alkyl group having 1 to 20 carbon atoms, a substituted or unsubstituted heteroaryl group having 3 to 50 ring atoms, and a halogen atom, more preferably a hydrogen atom or a substituted or unsubstituted alkyl group having 1 to 20 carbon atoms, and still more preferably a hydrogen atom.

In an embodiment of the invention, $R^1$ is a substituted or unsubstituted aryl group having 6 to 50 ring carbon atoms, and $R^2$ is selected from a hydrogen atom, a substituted or unsubstituted alkyl group having 1 to 20 carbon atoms, a substituted or unsubstituted heteroaryl group having 3 to 50 ring atoms, and a halogen atom, preferably a hydrogen atom or a substituted or unsubstituted alkyl group having 1 to 20 carbon atoms, and more preferably a hydrogen atom.

In an embodiment of the invention, the group in formula (1) which is represented by formula (4):

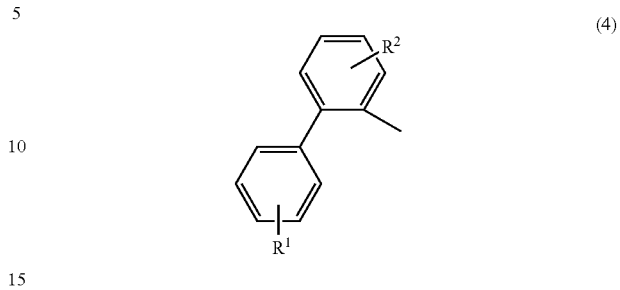

is preferably represented by formula (4a) or (4b) and more preferably by formula (4a):

wherein $R^1$ and $R^2$ each represent a substituted or unsubstituted aryl group having 6 to 50 ring carbon atoms.

Formula (4a) is preferably represented by

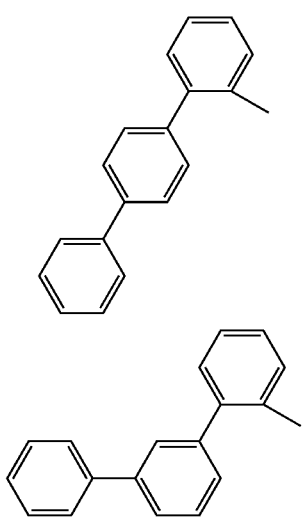

-continued

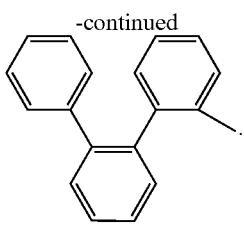

Formula (4b) is preferably represented by

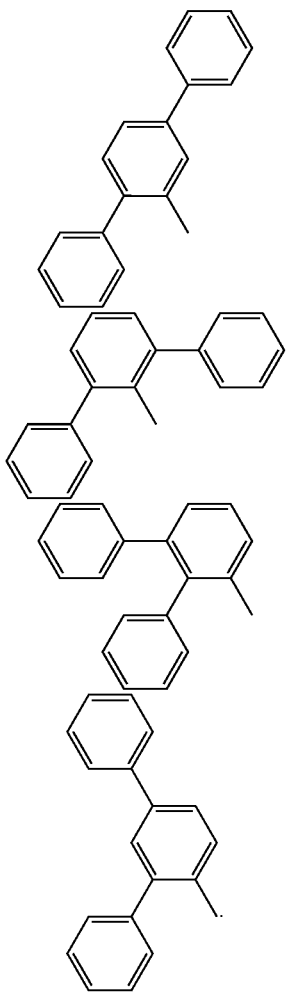

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the substituted or unsubstituted aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group. Preferred are a phenyl group, a naphthylphenyl group, a biphenylyl group, a terphenylyl group, a naphthyl group, and a 9,9-dimethylfluorenyl group, with a phenyl group, a biphenylyl group, a naphthyl group, and a 9,9-dimethylfluorenyl group being more preferred, and a phenyl group being still more preferred.

The heterocyclic group having 3 to 50 ring atoms comprises at least one, preferably 1 to 3 heteroatoms which may be the same or different, such as a nitrogen atom, a sulfur atom and an oxygen atom. Examples of the heterocyclic group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group, with a benzofuranyl group, a benzothiophenyl group, a dibenzofuranyl group, and a dibenzothiophenyl group being more preferred.

Examples of the halogen atom include a fluorine atom, a chlorine atom, a bromine atom, and a iodine atom, with a fluorine atom being preferred.

Examples of the fluoroalkyl group having 1 to 20 carbon atoms include those derived from the above alkyl group having 1 to 20 carbon atoms by replacing at least one hydrogen atom, preferably 1 to 7 hydrogen atoms or all hydrogen atoms with a fluorine atom or fluorine atoms. Preferred examples thereof are a heptafluoropropyl group, a pentafluoroethyl group, a 2,2,2-trifluoroethyl group, and a trifluoromethyl group, with a pentafluoroethyl group, a 2,2,2-trifluoroethyl group, and a trifluoromethyl group being more preferred, and a trifluoromethyl group being still more preferred.

The alkoxy group having 1 to 20 carbon atoms is represented by —$OR^{10}$, wherein $R^{10}$ is the above alkyl group having 1 to 20 carbon atoms. Preferred examples thereof include a t-butoxy group, a propoxy group, an ethoxy group, and a methoxy group, with an ethoxy group and a methoxy group being more preferred, and a methoxy group being still more preferred.

The fluoroalkoxy group having 1 to 20 carbon atoms is represented by —OR$^{11}$, wherein R$^{11}$ is the above fluoroalkyl group having 1 to 20 carbon atoms. Preferred examples thereof include a heptafluoropropoxy group, a pentafluoroethoxy group, a 2,2,2-trifluoroethoxy group, and a trifluoromethoxy group, with a pentafluoroethoxy group, a 2,2,2-trifluoroethoxy group, and a trifluoromethoxy group being more preferred, and a trifluoromethoxy group being still more preferred.

The aryloxy group having 6 to 50 ring carbon atoms is represented by —OR$^{12}$, wherein R$^{12}$ is the above aryl group having 6 to 50 ring carbon atoms, preferably a terphenyl group, a biphenyl group and a phenyl group, more preferably a biphenyl group and a phenyl group, and still more preferably a phenyl group.

When one or both of R$^1$ and R$^2$ each represent a substituted or unsubstituted aryl group having 6 to 50 ring carbon atoms, the aryl group and the benzene ring to which R$^1$ or R$^2$ is bonded may be crosslinked. Examples of the crosslinking group include —O—, —S—, —NR$^a$—, and —CR$^b$R$^c$—.

R$^a$, R$^b$ and R$^c$ each represent a hydrogen atom, a substituted or unsubstituted alkyl group having 1 to 20 carbon atoms, a substituted or unsubstituted aryl group having 6 to 50 ring carbon atoms, a substituted or unsubstituted heteroaryl group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group. R$^b$ and R$^c$ may be the same or different and may be bonded to each other to form a ring.

R$^a$ is preferably a hydrogen atom, a substituted or unsubstituted alkyl group having 1 to 20 carbon atoms, or a substituted or unsubstituted aryl group having 6 to 50 ring carbon atoms. R$^b$ and R$^c$ are each preferably a substituted or unsubstituted alkyl group having 1 to 20 carbon atoms or a substituted or unsubstituted aryl group having 6 to 50 ring carbon atoms and more preferably a substituted or unsubstituted alkyl group having 1 to 20 carbon atoms.

Examples, preferred examples, more preferred examples, and still more preferred examples of the alkyl group having 1 to 20 carbon atoms, the aryl group having 6 to 50 ring carbon atoms, the heteroaryl group having 3 to 50 ring atoms, the halogen atom, the fluoroalkyl group having 1 to 20 carbon atoms, the alkoxy group having 1 to 20 carbon atoms, the fluoroalkoxy group having 1 to 20 carbon atoms, and the aryloxy group having 6 to 50 ring carbon atoms are the same as those of the corresponding groups described above with respect to R$^1$ and R$^2$.

Examples of the crosslinked structure formed by the aryl group and the benzene ring to which R$^1$ or R$^2$ is bonded include a dibenzofuran structure, a dibenzothiophene structure, a carbazole structure, a N-arylcarbazole structure, a N-alkylcarbazole structure, a fluorene structure, a 9,9-dialkylfluorene structure, and a 9,9-diarylfluorene structure. The aryl group and the alkyl group in the carbazole structure and the fluorene structure are selected from the alkyl group having 1 to 20 carbon atoms and the aryl group having 6 to 50 ring carbon atoms each mentioned above.

In formula (1), Ar$^1$ represents a group represented by formula (2) or (3), preferably a group represented by formula (2). Ar$^2$ represents a group selected from a group represented by formula (2), a group represented by formula (3), and a substituted or unsubstituted aryl group having 6 to 50, preferably 6 to 24, and more preferably 6 to 12 ring carbon atoms, and preferably represents a substituted or unsubstituted aryl group having 6 to 50 ring carbon atoms.

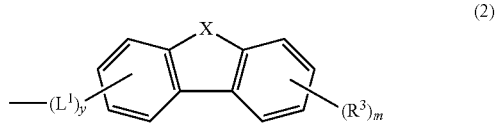

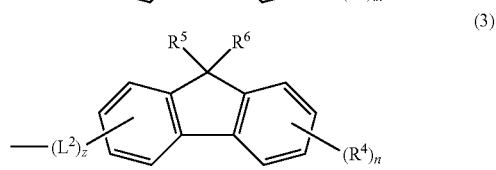

In formula (2), X represents an oxygen atom or an sulfur atom, preferably an oxygen atom.

L$^1$ represents a substituted or unsubstituted arylene group having 6 to 50, preferably 6 to 24, and more preferably 6 to 12 ring carbon atoms.

The arylene group having 6 to 50 ring carbon atoms is a divalent group which is derived from the aryl group having 6 to 50 ring carbon atoms mentioned above with respect to R$^1$ and R$^2$ by removing one hydrogen atom, and preferably a terpnenyldiyl group (inclusive of isomeric groups), a biphenyldiyl group (inclusive of isomeric groups), and a phenylene group (inclusive of isomeric groups), more preferably a biphenyldiyl group (inclusive of isomeric groups) and a phenylene group (inclusive of isomeric groups), and still more preferably an o-phenylene group, a m-phenylene group and a p-phenylene group.

The subscript y is 0 or 1 and preferably 1. When y is 0, (L$^1$)$_0$ is a single bond.

R$^3$ is selected from a substituted or unsubstituted alkyl group having 1 to 20, preferably 1 to 5, more preferably 1 to 4 carbon atoms, a substituted or unsubstituted aryl group having 6 to 50, preferably 6 to 24, more preferably 6 to 12 ring carbon atoms, a substituted or unsubstituted heteroaryl group having 3 to 50, preferably 3 to 24, more preferably 3 to 12 ring atoms, a halogen atom, a substituted or unsubstituted fluoroalkyl group having 1 to 20, preferably 1 to 5, more preferably 1 to 4 carbon atoms, a substituted or unsubstituted alkoxy group having 1 to 20, preferably 1 to 5, more preferably 1 to 4 carbon atoms, a substituted or unsubstituted fluoroalkoxy group having 1 to 20, preferably 1 to 5, more preferably 1 to 4 carbon atoms, a substituted or unsubstituted aryloxy group having 6 to 50, preferably 6 to 24, more preferably 6 to 12 ring carbon atoms, and a cyano group; preferably selected from the substituted or unsubstituted alkyl group, the substituted or unsubstituted aryl group, and the substituted or unsubstituted heteroaryl group; more preferably selected from the substituted or unsubstituted alkyl group and the substituted or unsubstituted aryl group, and still more preferably selected from the substituted or unsubstituted aryl group.

Examples, preferred examples, more preferred examples, and still more preferred examples of the alkyl group having 1 to 20 carbon atoms, the aryl group having 6 to 50 ring carbon atoms, the heteroaryl group having 3 to 50 ring atoms, the halogen atom, the fluoroalkyl group having 1 to 20 carbon atoms, the alkoxy group having 1 to 20 carbon atoms, the fluoroalkoxy group having 1 to 20 carbon atoms, and the aryloxy group having 6 to 50 ring carbon atoms are the same as those of the corresponding groups described above with respect to $R^1$ and $R^2$.

The subscript m is an integer of 0 to 4, preferably an integer of 0 to 2, more preferably 0 or 1, and still more preferably 0. When m is an integer of 2 to 4, two to four groups $R^3$ may be the same or different, and two groups $R^3$ may be bonded to each other to form a ring. When m is 0, $(R^3)_0$ is a hydrogen atom.

In formula (2), $L^1$ is bonded to 1-, 2-, 3-, or 4-position, preferably 2- or 4-position of the dibenzofuran structure or the dibenzothiophene structure:

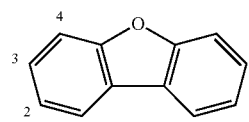

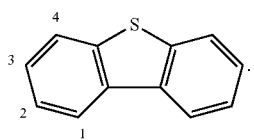

In an embodiment of the invention, formula (2) is represented by formula (2a) or (2b):

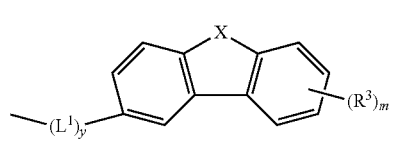

(2a)

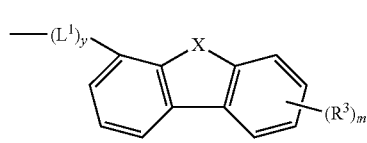

(2b)

wherein $L^1$, y, X, $R^3$, and m are as defined above.

In another embodiment of the invention, formula (2) is represented by formula (2a') or (2b'):

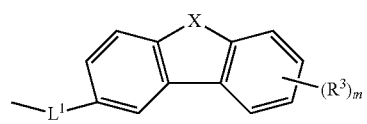

(2a')

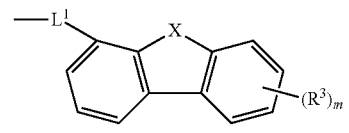

(2b')

wherein $L^1$, X, $R^3$, and m are as defined above.

Formula (2a') is preferably represented by formula (2a") and formula (2b') is preferably represented by (2b"):

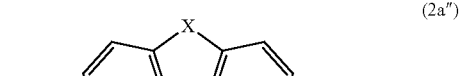

(2a")

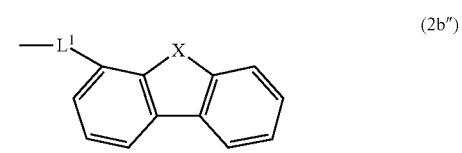

(2b")

wherein $L^1$ and X are as defined above.

In still another embodiment of the invention, formula (2) is represented by formula (2a"-1) or (2b"-1):

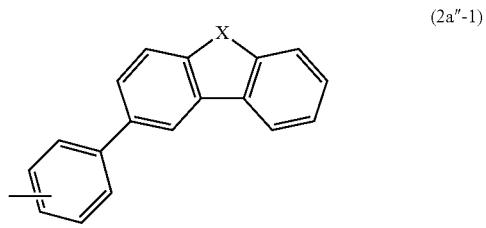

(2a"-1)

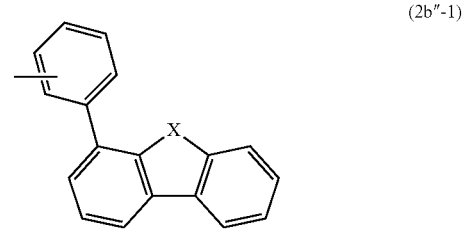

(2b"-1)

wherein X is as defined above.

In still another embodiment of the invention, formula (2) is represented by any of the following groups:

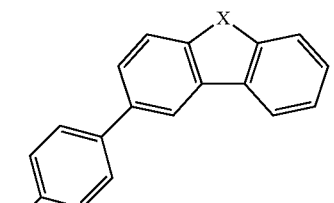

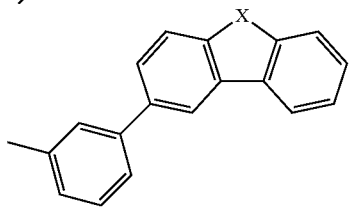

-continued

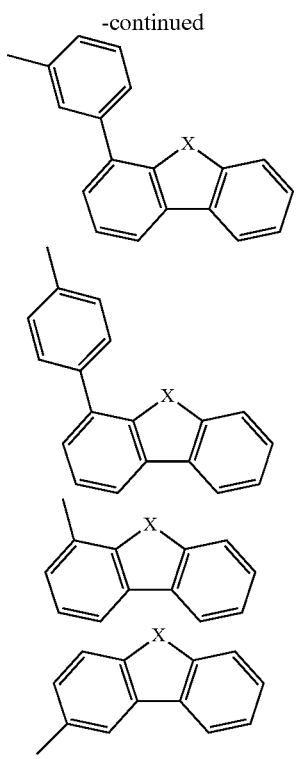

wherein X is as defined above.

In formula (3), $R^5$ and $R^6$ are each independently a hydrogen atom, a substituted or unsubstituted alkyl group having 1 to 20, preferably 1 to 5, more preferably 1 to 4 carbon atoms, a substituted or unsubstituted aryl group having 10 to 50, preferably 10 to 24, more preferably 10 to 12 ring carbon atoms, a substituted or unsubstituted heteroaryl group having 3 to 50, preferably 3 to 24, more preferably 3 to 12 ring atoms, a halogen atom, a substituted or unsubstituted fluoroalkyl group having 1 to 20, preferably 1 to 5, more preferably 1 to 4 carbon atoms, a substituted or unsubstituted alkoxy group having 1 to 20, preferably 1 to 5, more preferably 1 to 4 carbon atoms, a substituted or unsubstituted fluoroalkoxy group having 1 to 20, preferably 1 to 5, more preferably 1 to 4 carbon atoms, a substituted or unsubstituted aryloxy group having 6 to 50, preferably 6 to 24, more preferably 6 to 12 ring carbon atoms, or cyano group; preferably selected from the substituted or unsubstituted alkyl group and the substituted or unsubstituted aryl group; and more preferably selected from the substituted or unsubstituted alkyl group.

Examples, preferred examples, more preferred examples, and still more preferred examples of the alkyl group having 1 to 20 carbon atoms, the heteroaryl group having 3 to 50 ring atoms, the halogen atom, the fluoroalkyl group having 1 to 20 carbon atoms, the alkoxy group having 1 to 20 carbon atoms, the fluoroalkoxy group having 1 to 20 carbon atoms, and the aryloxy group having 6 to 50 ring carbon atoms are the same as those of the corresponding groups described above with respect to $R^1$ and $R^2$.

Examples of the substituted or unsubstituted aryl group having 10 to 50 ring carbon atoms include a naphthylphenyl group, a biphenylyl group, a terphenylyl group, a biphenylenyl group, a naphthyl group, a phenylnaphthyl group, an acenaphthylenyl group, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group. Preferred are a naphthylphenyl group, a biphenylyl group, a terphenylyl group, a naphthyl group, and a 9,9-dimethylfluorenyl group, with a biphenylyl group, a naphthyl group, and a 9,9-dimethylfluorenyl group being more preferred, and a biphenylyl group and a naphthyl group being still more preferred.

In formula (3), $L^2$ represents a substituted or unsubstituted arylene group having 6 to 50, preferably 6 to 24, more preferably 6 to 12 ring carbon atoms.

The arylene group having 6 to 50 ring carbon atoms is a divalent group which is derived from the aryl group having 6 to 50 ring carbon atoms mentioned above with respect to $R^1$ and $R^2$ by removing one hydrogen atom, and preferably a terpnenyldiyl group (inclusive of isomeric groups), a biphenyldiyl group (inclusive of isomeric groups), and a phenylene group (inclusive of isomeric groups), more preferably a biphenyldiyl group (inclusive of isomeric groups) and a phenylene group (inclusive of isomeric groups), and still more preferably an o-phenylene group, a m-phenylene group and a p-phenylene group.

The subscript z is 0 or 1 and preferably 0. When z is 0, $(L^2)_0$ is a single bond.

$R^4$ is selected from a substituted or unsubstituted alkyl group having 1 to 20, preferably 1 to 5, more preferably 1 to 4 carbon atoms, a substituted or unsubstituted aryl group having 6 to 50, preferably 6 to 24, more preferably 6 to 12 ring carbon atoms, a halogen atom, a substituted or unsubstituted fluoroalkyl group having 1 to 20, preferably 1 to 5, more preferably 1 to 4 carbon atoms, a substituted or unsubstituted alkoxy group having 1 to 20, preferably 1 to 5, more preferably 1 to 4 carbon atoms, a substituted or unsubstituted fluoroalkoxy group having 1 to 20, preferably 1 to 5, more preferably 1 to 4 carbon atoms, a substituted or unsubstituted aryloxy group having 6 to 50, preferably 6 to 24, more preferably 6 to 12 ring carbon atoms, and a cyano group; preferably selected from the substituted or unsubstituted alkyl group and the substituted or unsubstituted aryl group; and more preferably selected from the substituted or unsubstituted aryl group.

Examples, preferred examples, more preferred examples, and still more preferred examples of the alkyl group having 1 to 20 carbon atoms, the aryl group having 6 to 50 ring carbon atoms, the halogen atom, the fluoroalkyl group having 1 to 20 carbon atoms, the alkoxy group having 1 to 20 carbon atoms, the fluoroalkoxy group having 1 to 20 carbon atoms, and the aryloxy group having 6 to 50 ring carbon atoms are the same as those of the corresponding groups described above with respect to $R^1$ and $R^2$.

The subscript n is an integer of 0 to 4, preferably an integer of 0 to 2, more preferably 0 and 1, and still more preferably 0. When m is an integer of 2 to 4, two to four groups $R^4$ may be the same or different, and two groups $R^4$ may be bonded to each other to form a ring. When n is 0, $(R^4)_0$ is a hydrogen atom.

In a preferred embodiment of the invention, one of $R^1$ and $R^2$ is the substituted or unsubstituted aryl group having 6 to 50 ring carbon atoms; the other is a hydrogen atom; and n is 0. In another preferred embodiment of the invention, one of $R^1$ and $R^2$ is the substituted or unsubstituted aryl group having 6 to 50 ring carbon atoms; the other is the substituted or unsubstituted alkyl group having 1 to 20 carbon atoms, the substituted or unsubstituted heteroaryl group having 3 to 50 ring atoms, the halogen atom, the substituted or unsubstituted fluoroalkyl group having 1 to 20 carbon atoms, the substituted or unsubstituted alkoxy group having 1 to 20 carbon atoms, the substituted or unsubstituted fluoroalkoxy group having 1 to 20 carbon atoms, the substituted or unsubstituted aryloxy group having 6 to 50 ring carbon atoms, or a cyano group; and n is an integer of 0 to 4.

In formula (3), $L^2$ is bonded to 1-, 2-, 3-, or 4-position, preferably 2-position of the fluorene structure:

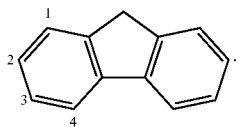

In an embodiment of the invention, formula (3) is represented by formula (3a):

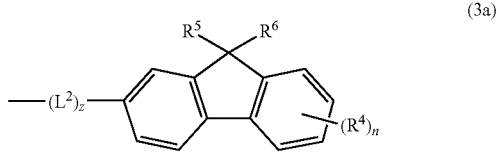

wherein $L^2$, z, $R^4$, $R^5$, $R^6$, and are as defined above.

In another embodiment of the invention, formula (3) is represented by formula (3a'):

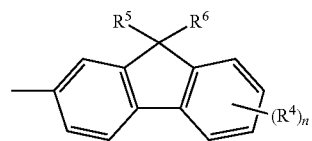

wherein $R^4$, $R^5$, $R^6$, and n are as defined above.

Formula (3a') is preferably represented by formula (3a"):

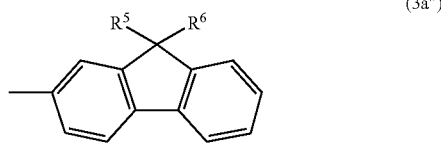

wherein $R^5$ and $R^6$ are as defined above.

In another embodiment of the invention, formula (3) is preferably represented by the following group:

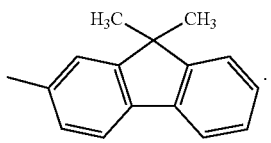 [SMILES: Cc1ccc2c(c1)C(C)(C)c1ccccc1-2]

Examples of the aryl group in the substituted or unsubstituted aryl group having 6 to 50 ring carbon atoms for $Ar^2$ include a phenyl group, a biphenylyl group, a terphenylyl group, a biphenylenyl group, a naphthyl group, an acenaphthylenyl, an anthryl group, a benzanthryl group, an aceanthryl group, a phenanthryl group, a triphenylenyl group, a bonzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group.

Examples of the substituted aryl group include those having the optional substituent mentioned above and further include a naphthylphenyl group, a phenylnaphthyl group, a 9,9-dimethylfluorenyl group, a 9,9-diphenylfluorenyl group, a 9,9-bis(p-methylphenyl)fluorenyl group, a 7-phenyl-9,9-diphenylfluorenyl group, a p-(9,9-diphenylfluorenyl)phenyl group, a 7-phenyl-9,9-dimethylfluorenyl group, a 9,9'-spirobifluorenyl group, a spiro[9H-fluorenyl-9,1'-cyclopentane] group, and a spiro[9H-fluorenyl-9,1'-cyclohexane] group.

The substituted or unsubstituted aryl group is preferably a phenyl group, a biphenylyl group, a terphenylyl group, a naphthyl group, a naphthylphenyl group, a 9,9-dimethylfluorene-2-yl group, a 9,9-diphenylfluorene-2-yl group, a 9,9-bis(p-methylphenyl)fluorene-2-yl group, a 7-phenyl-9,9-diphenylfluorene-2-yl group, a p-(9,9-diphenylfluorene-2-yl)phenyl group, and a 9,9'-spirobifluorene-2-yl group; more preferably a phenyl group, a biphenylyl group, a terphenylyl group, a naphthyl group, a naphthylphenyl group, a 9,9-dimethylfluorene-2-yl group, a 9,9-diphenylfluorene-2-yl group, a 9,9-bis(p-methylphenyl)fluorene-2-yl group, a 7-phenyl-9,9-diphenylfluorene-2-yl group, and a p-(9,9-diphenylfluorene-2-yl)phenyl group; and still more preferably a phenyl group, a biphenylyl group, a naphthyl group, a 9,9-dimethylfluorene-2-yl group, and a 9,9-diphenylfluorene-2-yl group.

In an embodiment of the invention, the substituted or unsubstituted aryl group is preferably a terphenylyl group, a phenyl-substituted terphenylyl group, a naphthyl group, a naphthylphenyl group, a 9,9-dimethylfluorene-2-yl group, a 9,9-diphenylfluorene-2-yl group, a 9,9-bis(p-methylphenyl)fluorene-2-yl group, a 7-phenyl-9,9-diphenylfluorene-2-yl group, a p-(9,9-diphenylfluorene-2-yl)phenyl group, and a 9,9'-spirobifluorene-2-yl group; more preferably a terphenylyl group, a phenyl-substituted terphenylyl group, a naphthyl group, a naphthylphenyl group, a 9,9-dimethylfluorene-2-yl group, a 9,9-diphenylfluorene-2-yl group, a 9,9-bis(p-methylphenyl)fluorene-2-yl group, a 7-phenyl-9,9-diphenylfluorene-2-yl group, and a p-(9,9-diphenylfluorene-2-yl)phenyl group; and still more preferably a terphenylyl group, a phenyl-substituted terphenylyl group, a naphthyl group, a 9,9-dimethylfluorene-2-yl group, and a 9,9-diphenylfluorene-2-yl group. Particularly, when $Ar^1$ is represented by formula (3) and $R^5$ and $R^6$ each represent an unsubstituted alkyl group having 1 to 20 carbon atoms, the substituted or unsubstituted aryl group for $Ar^2$ is preferably selected from the aryl group mentioned above.

The compound (1) is preferably represented by formula (1a) or (1b):

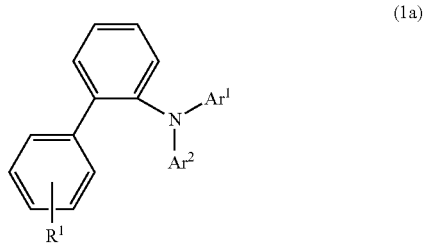

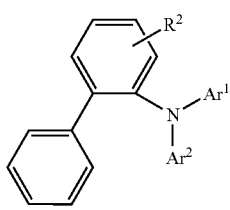

(1b)

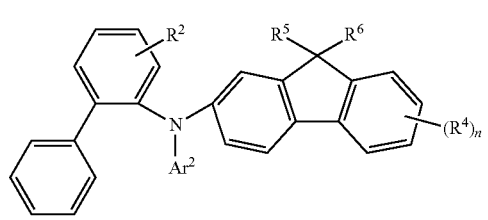

(1b-3)

wherein $R^1$ and $R^2$ each represent a substituted or unsubstituted aryl group having 6 to 50 ring carbon atoms, and $Ar^1$ and $Ar^2$ are as defined in formula (1). The compound (1) is also preferably represented by any of formulae (1a-1) to (1a-3) and (1b-1) to (1b-3):

wherein $R^1$ and $R^2$ each represent a substituted or unsubstituted aryl group having 6 to 50 ring carbon atoms;

$R^5$ and $R^6$ are as defined in formula (1) and each preferably represent a substituted or unsubstituted alkyl group having 1 to 20 carbon atoms;

$Ar^2$ is as defined in formula (1) and preferably represents a substituted or unsubstituted aryl group having 6 to 50 ring carbon atoms; and $L^1$, X, $R^3$, $R^4$, m, and n are as defined in formula (1).

The compound (1) is more preferably represented by any of formulae (1a-1') to (1a-3') and (1b-1') to (1b-3');

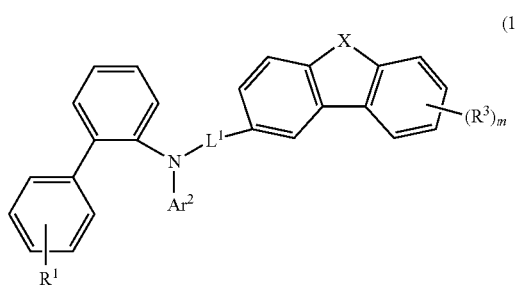

(1a-1)

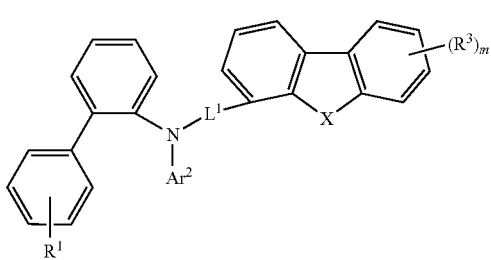

(1a-2)

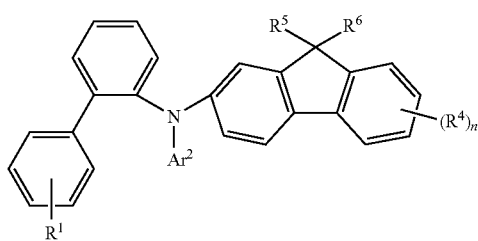

(1a-3)

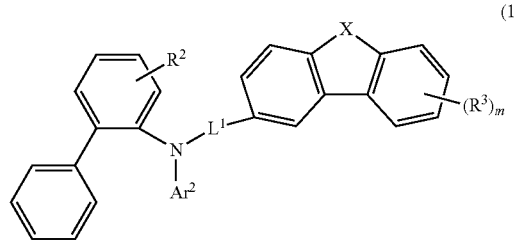

(1b-1)

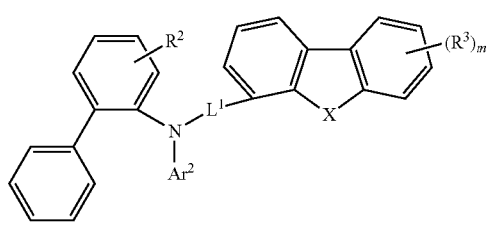

(1b-2)

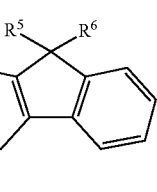

(1a-1')

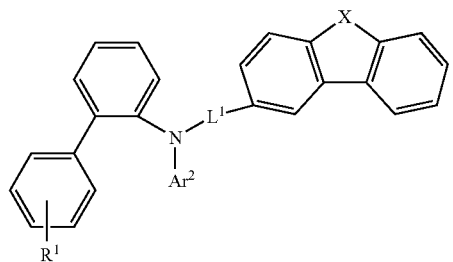

(1a-2')

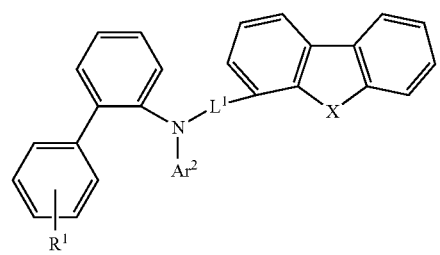

(1a-3')

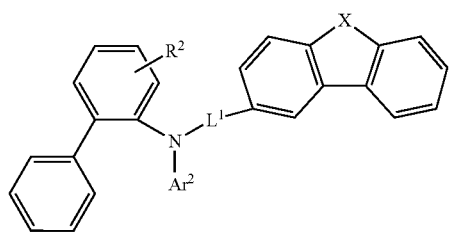

(1b-1')

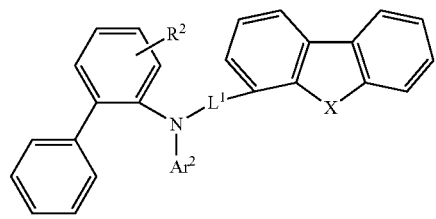

(1b-2')

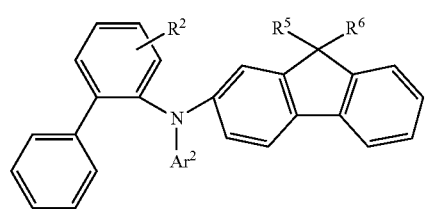

(1b-3')

R¹ and R² each represent a substituted or unsubstituted aryl group having 6 to 50 ring carbon atoms;

R⁵ and R⁶ are as defined in formula (1) and each preferably represent a substituted or unsubstituted alkyl group having 1 to 20 carbon atoms;

Ar² is as defined in formula (1) and preferably represents a substituted or unsubstituted aryl group having 6 to 50 ring carbon atoms; and L¹ and X are as defined in formula (1).

Examples of the compound (1) are shown below, although not limited thereto.

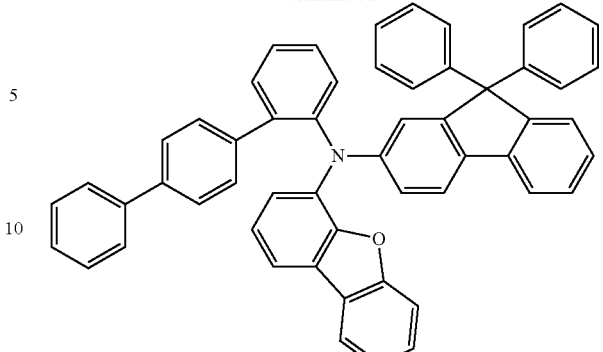

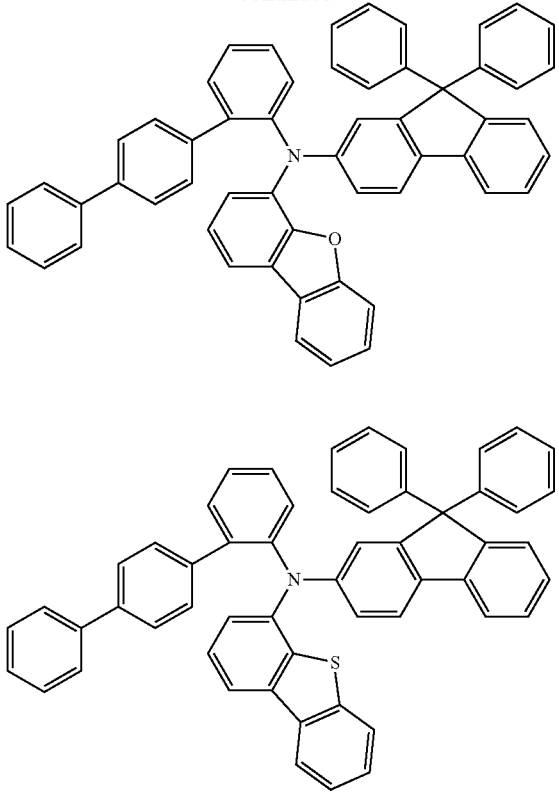

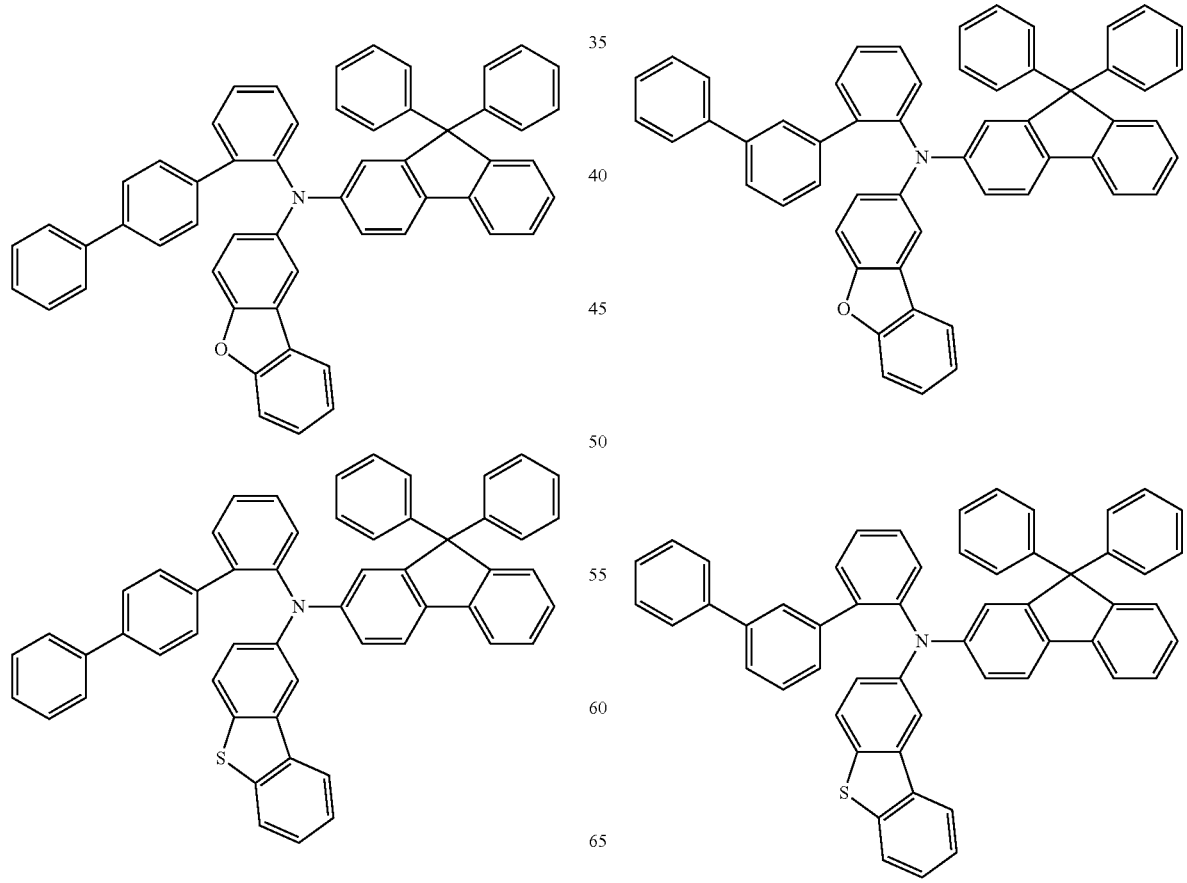

-continued
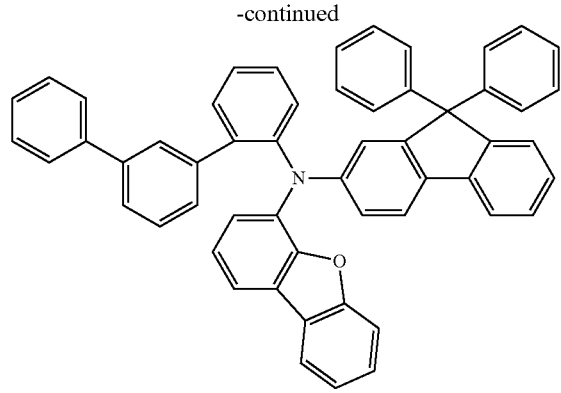
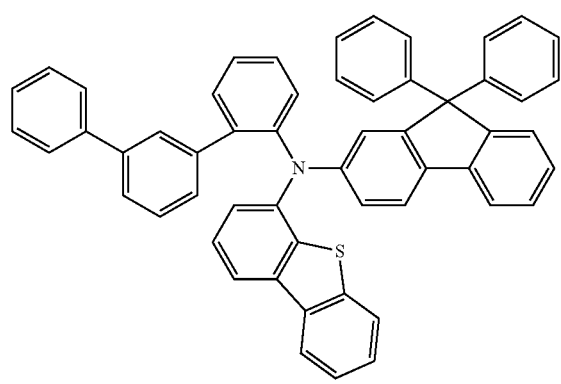
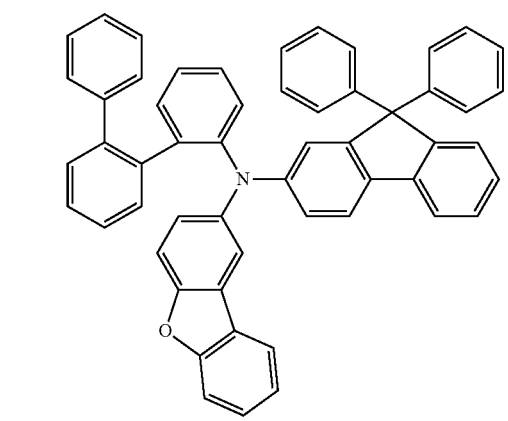
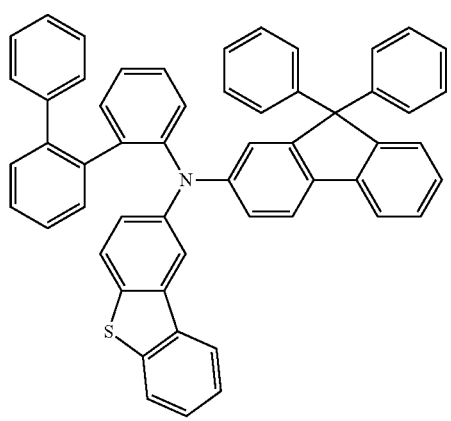
-continued
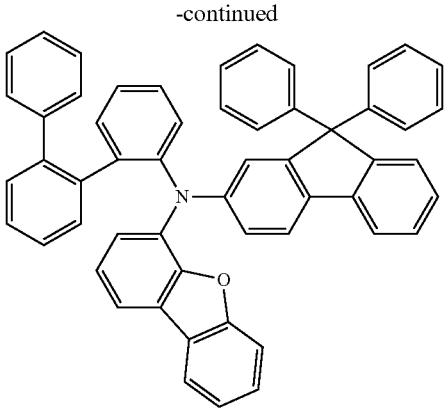
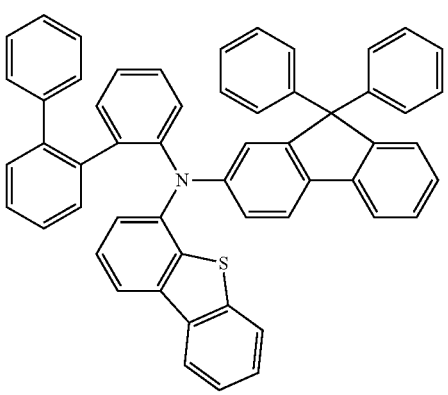
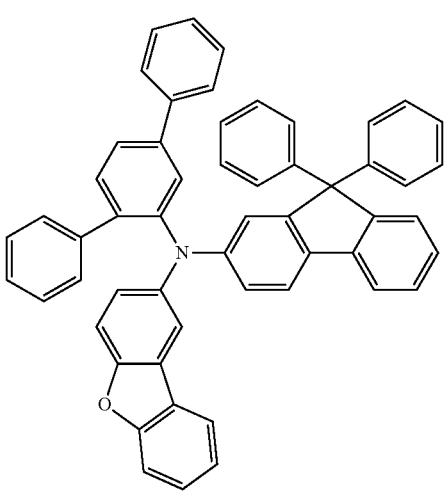

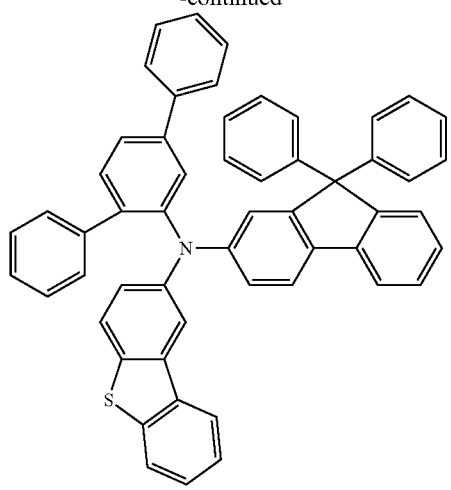
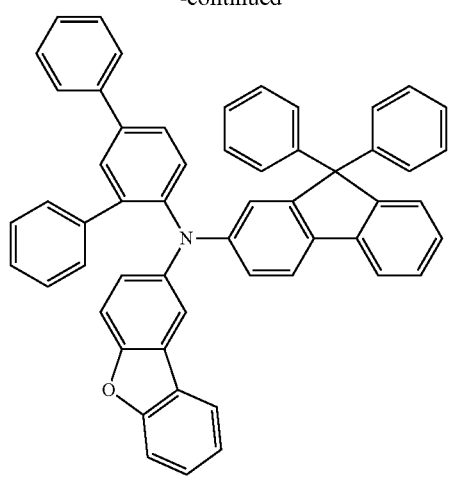
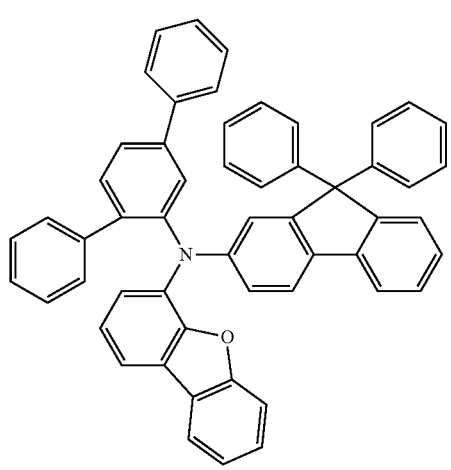
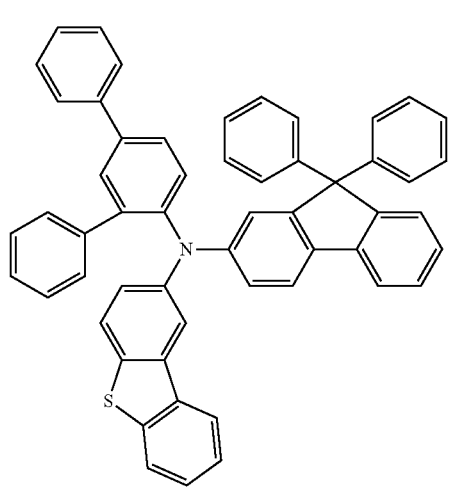
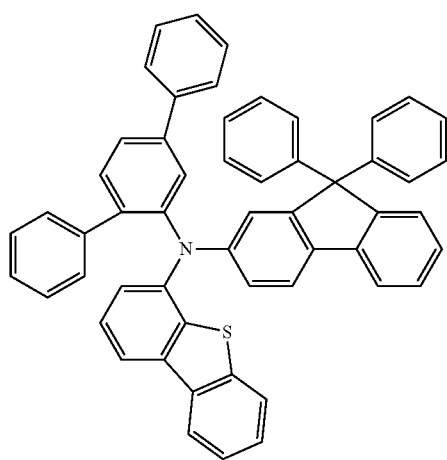 [SMILES: c1ccc(-c2ccc(-c3ccccc3)c(N(c3ccc4c(c3)C(c3ccccc3)(c3ccccc3)c3ccccc3-4)c3cccc4c3sc3ccccc34)c2)cc1]
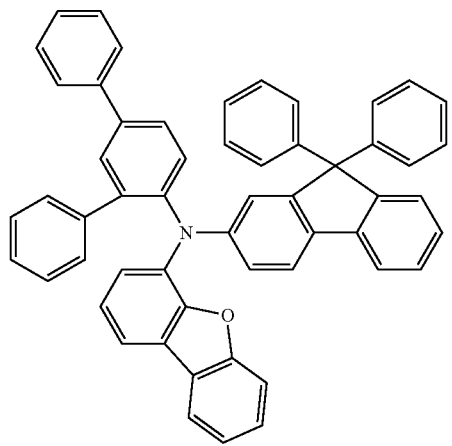 [SMILES: c1ccc(-c2ccc(N(c3ccc4c(c3)C(c3ccccc3)(c3ccccc3)c3ccccc3-4)c3cccc4c3sc3ccccc34)c(-c3ccccc3)c2)cc1]

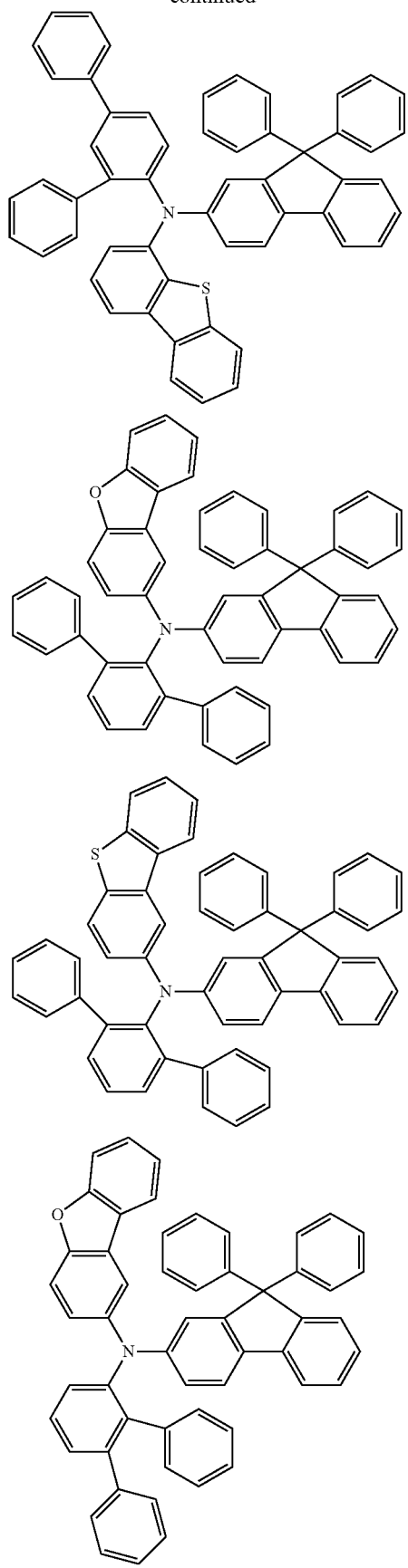
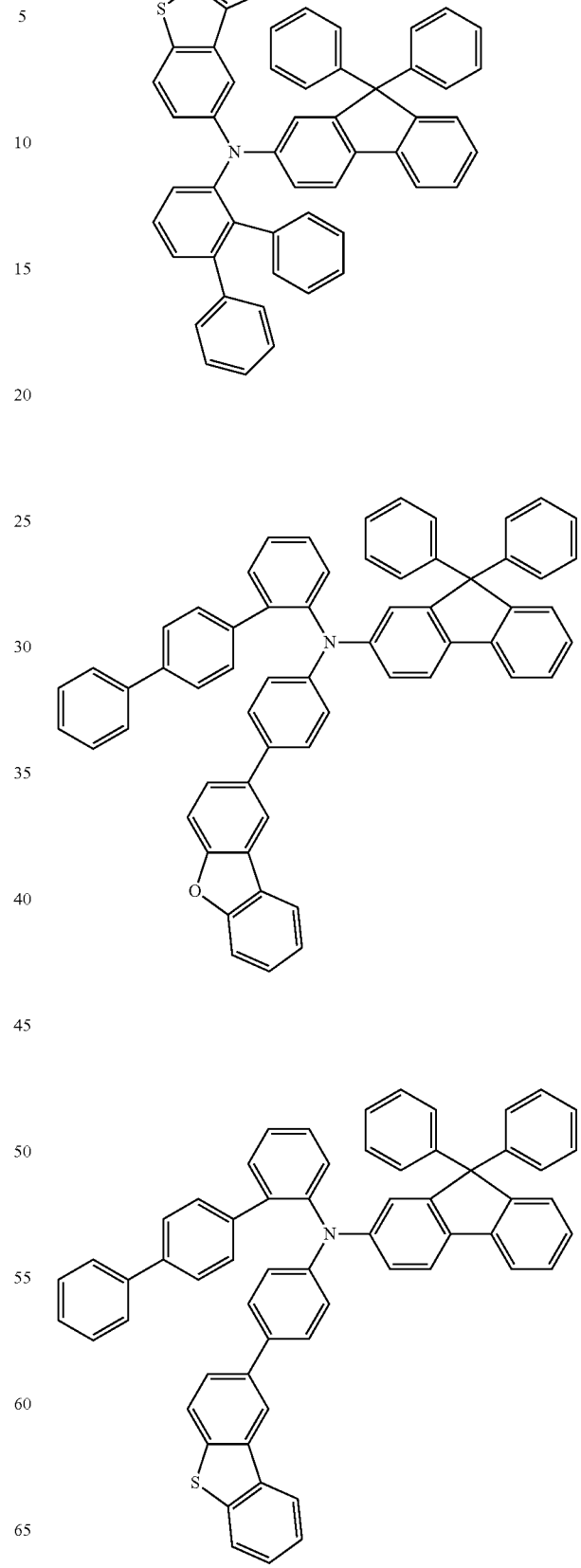

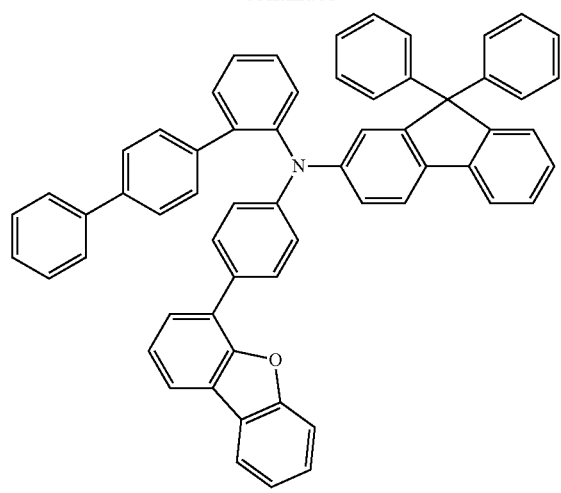
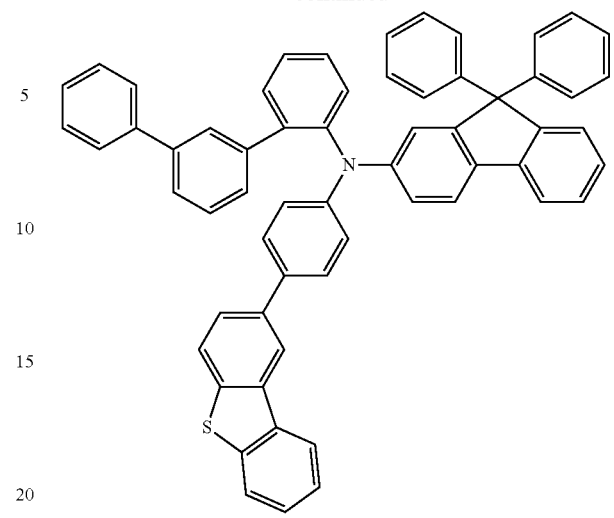
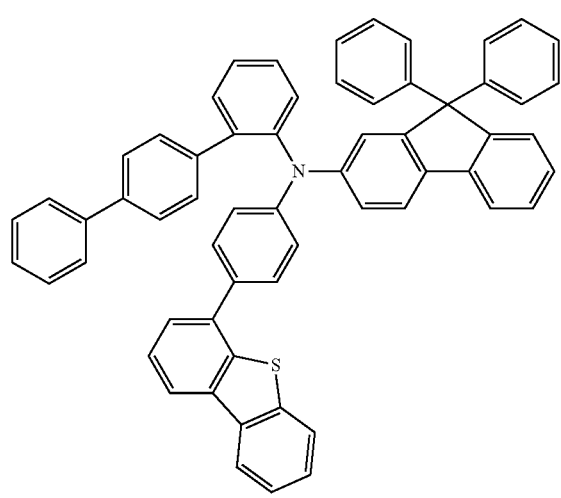
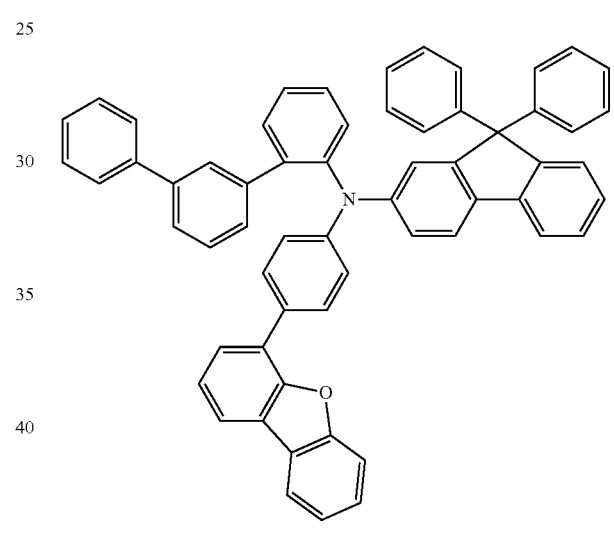
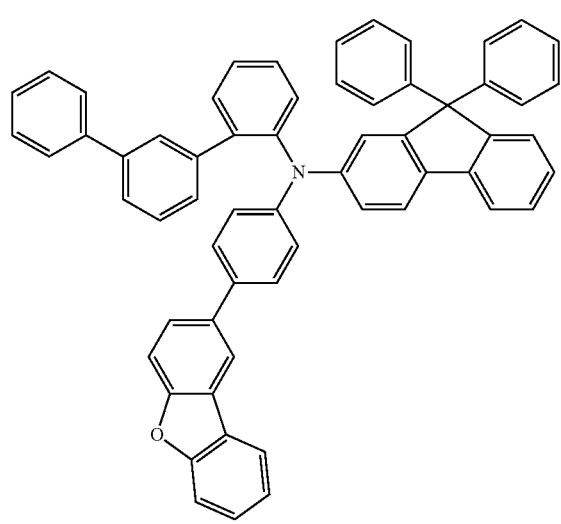
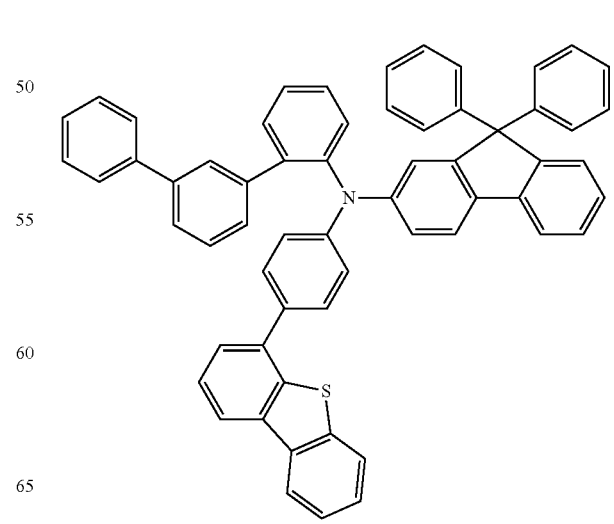

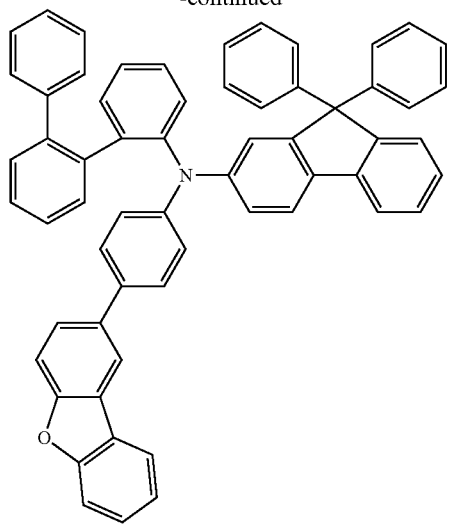
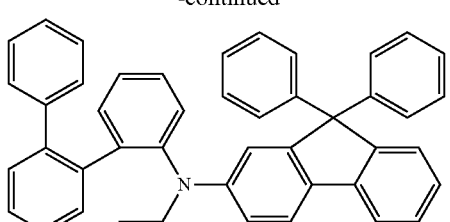
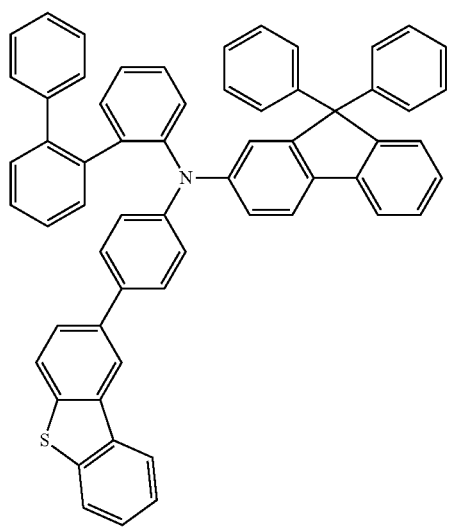
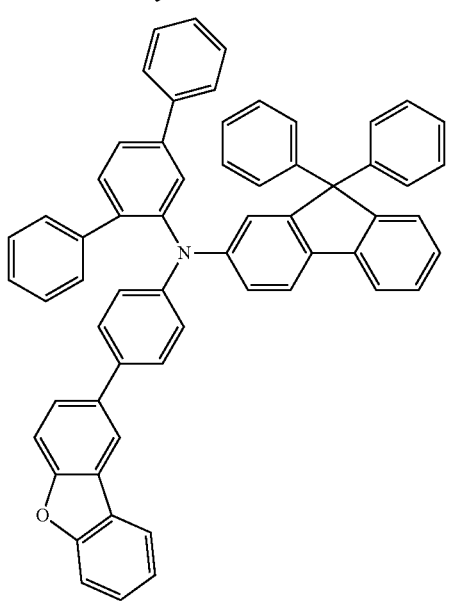
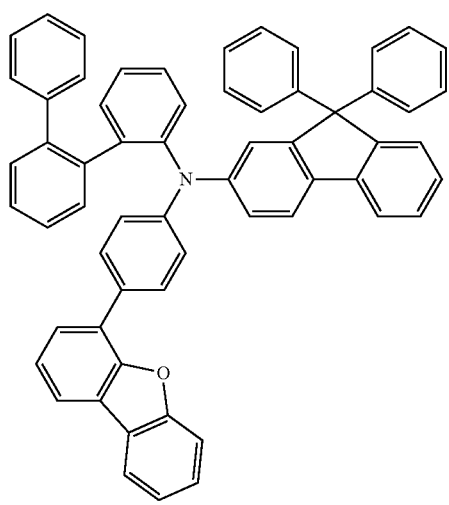
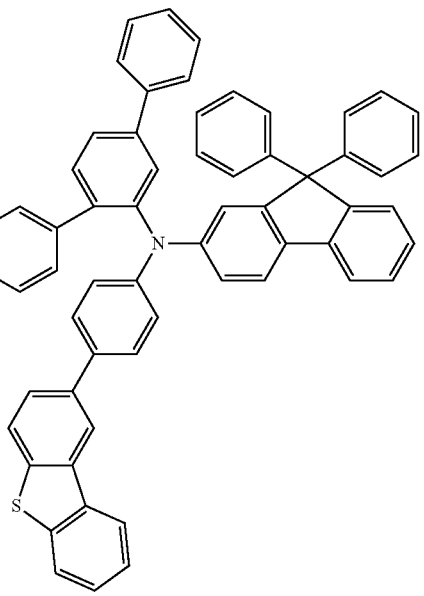

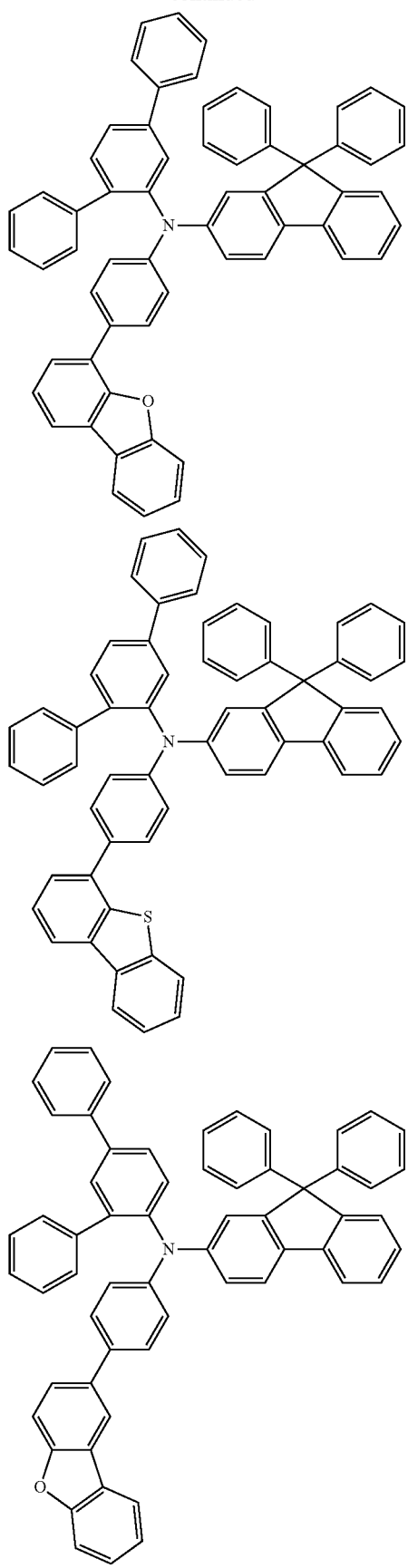
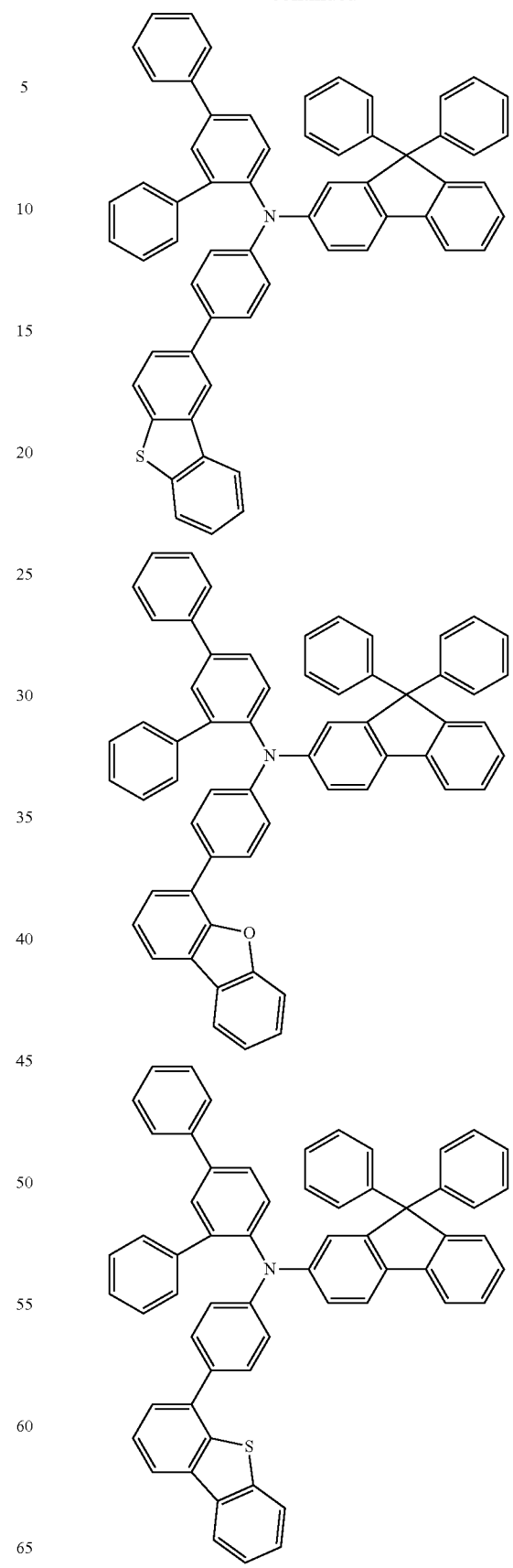

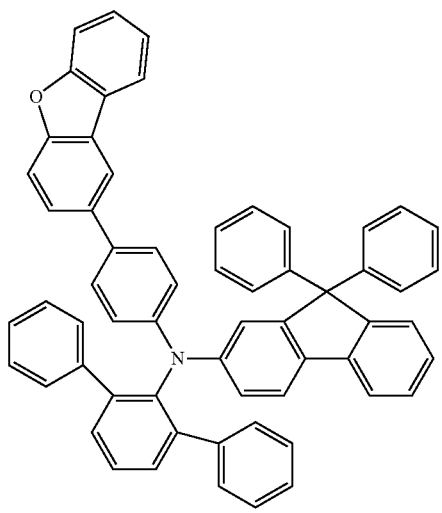
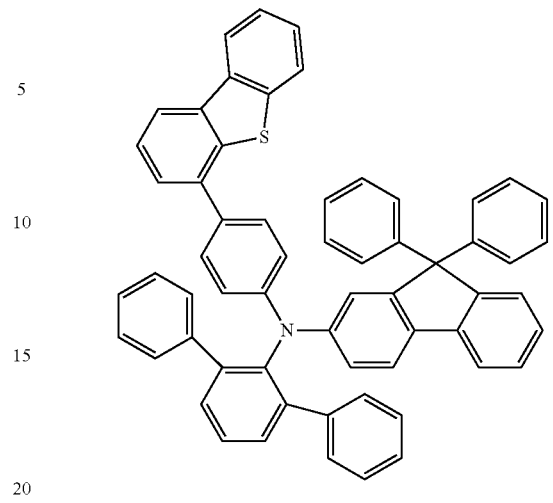
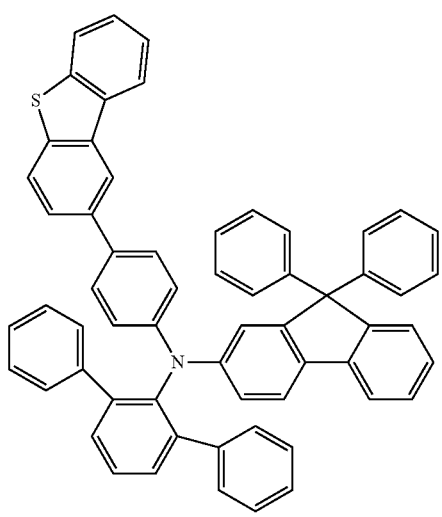
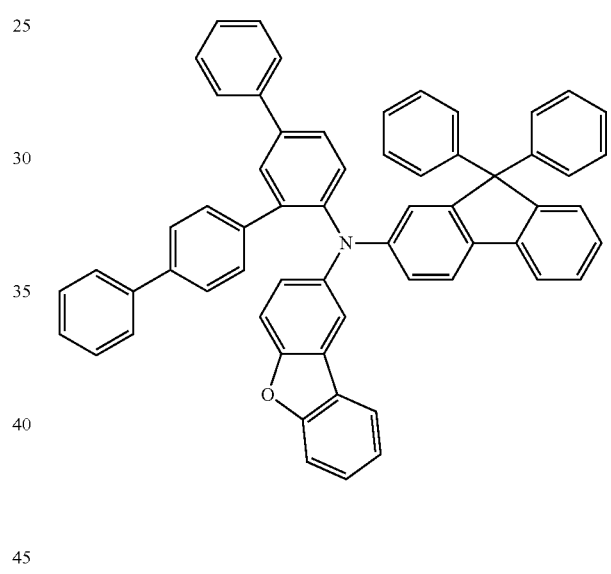
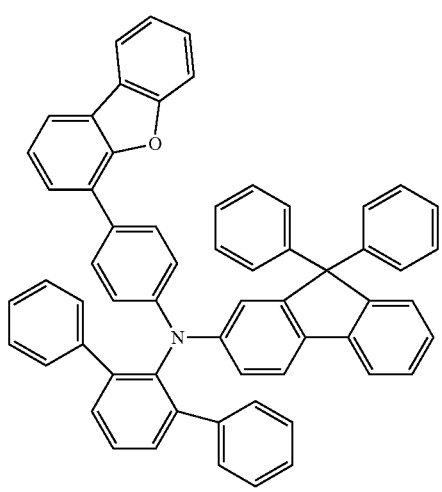
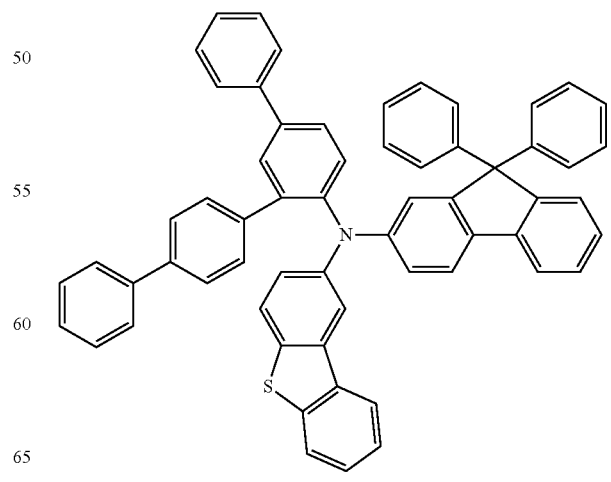

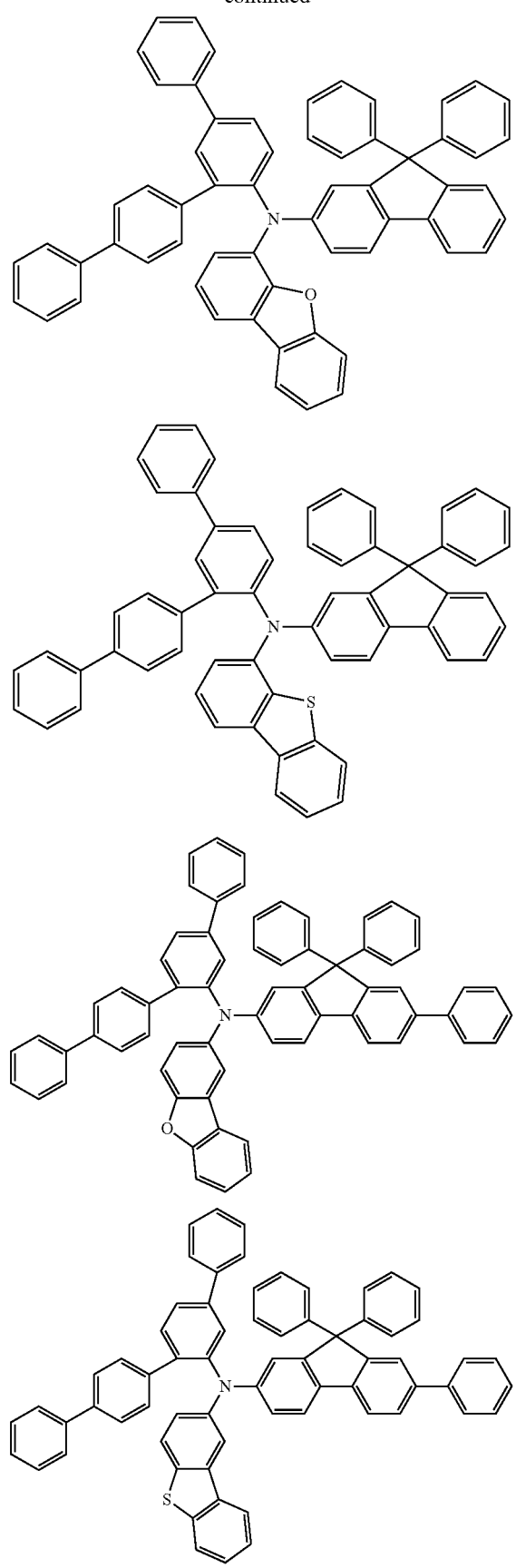
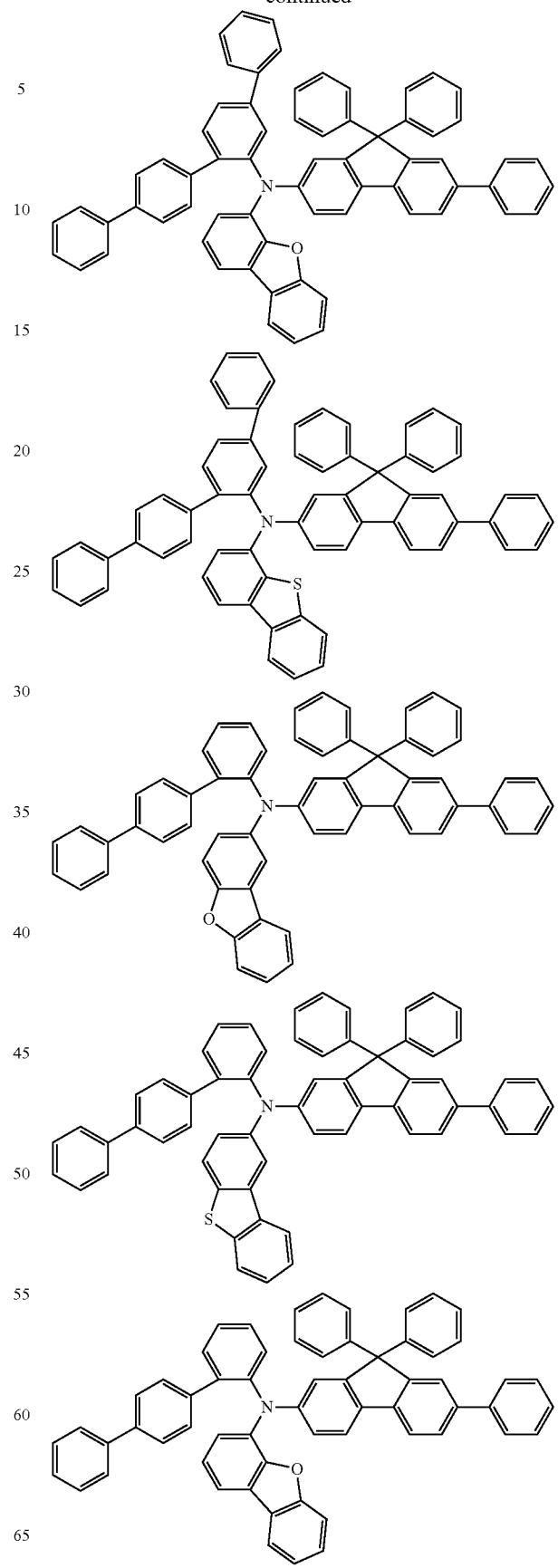

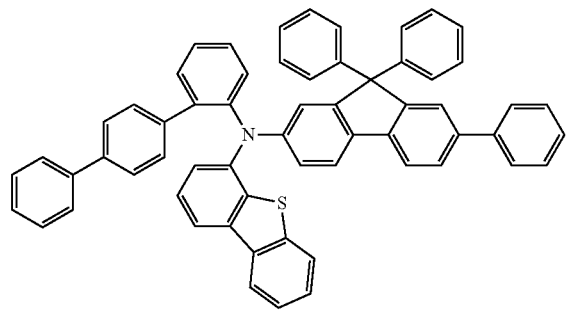
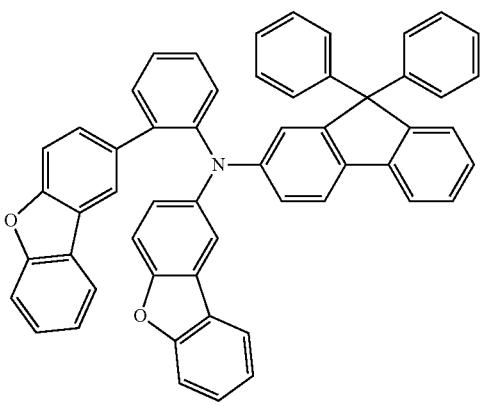
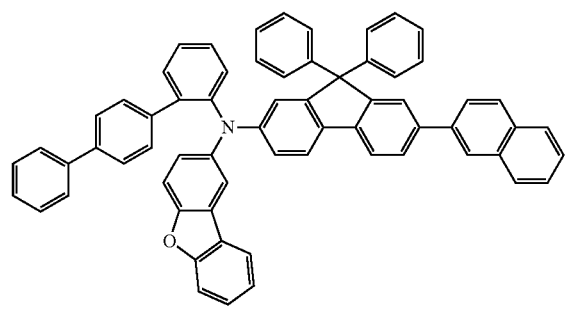
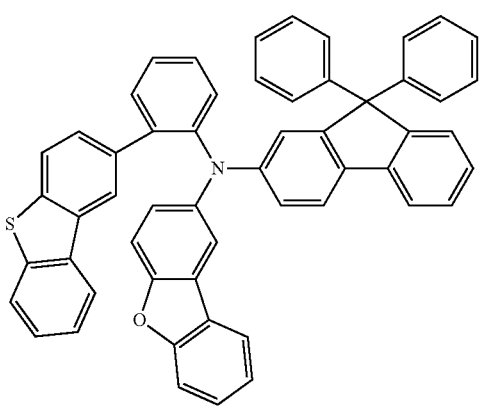
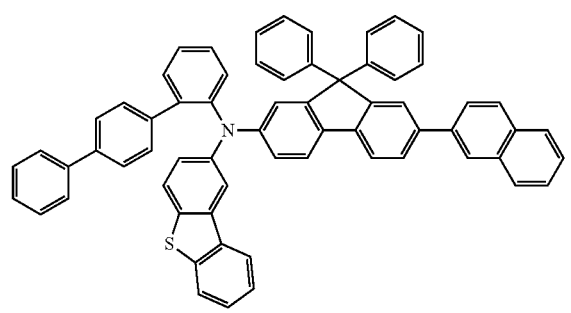
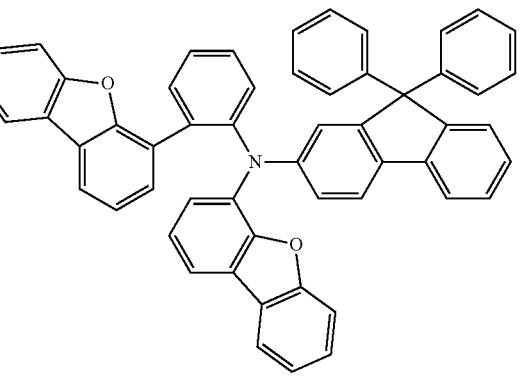
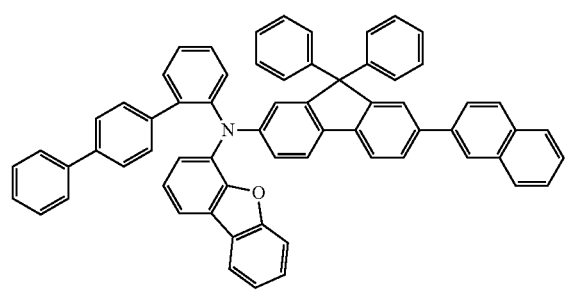
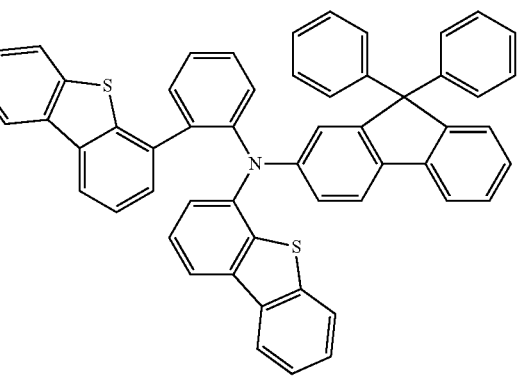

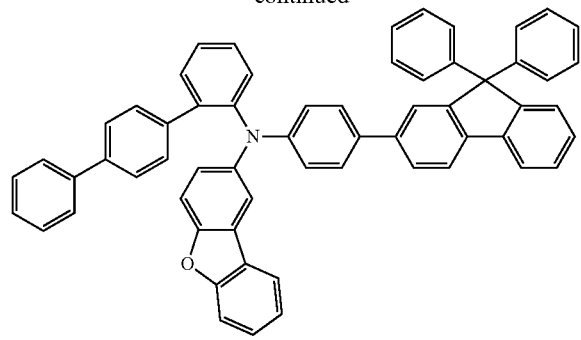
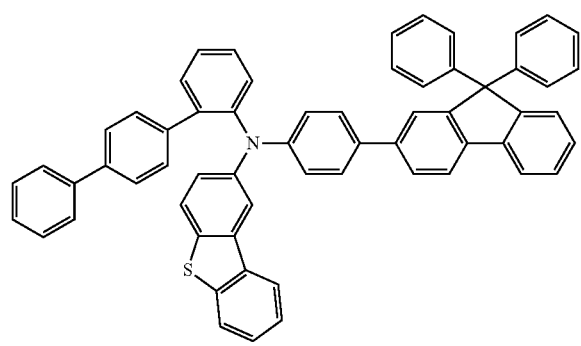
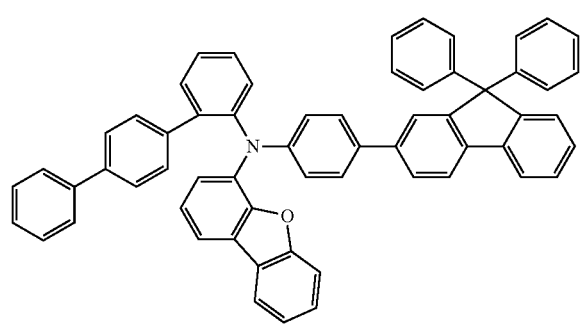
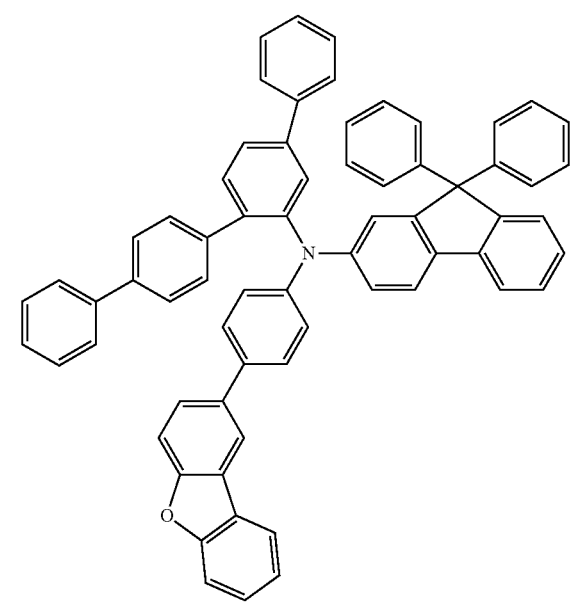
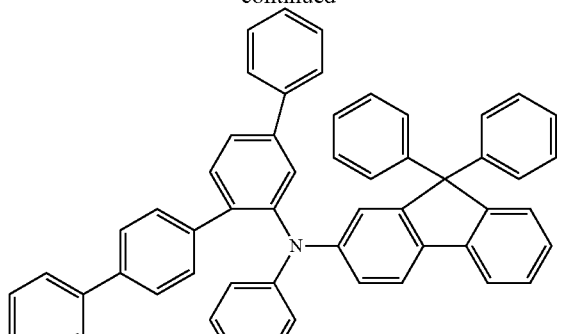
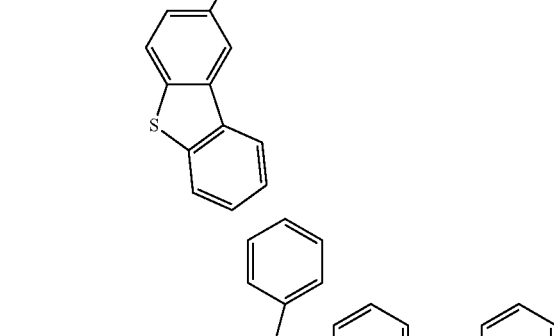
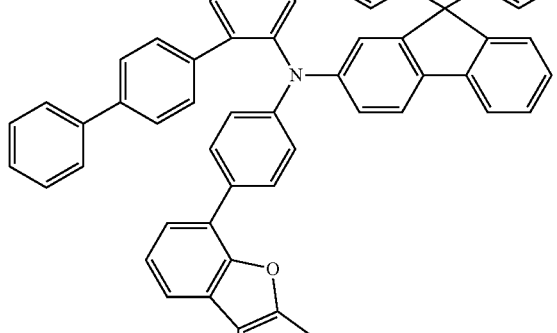
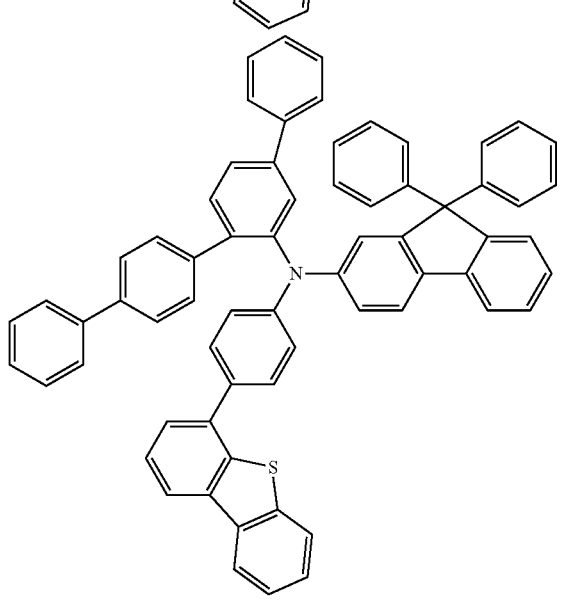

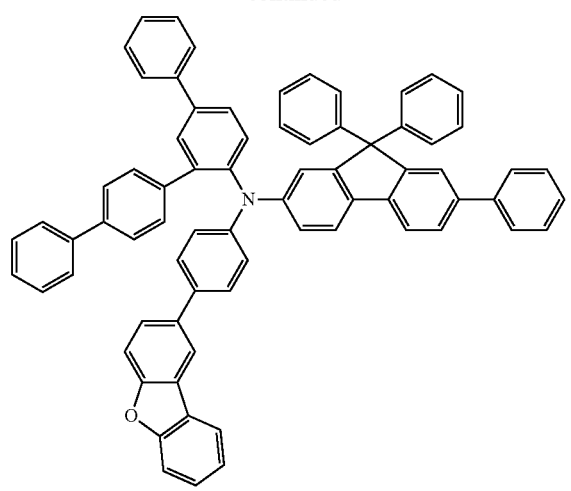
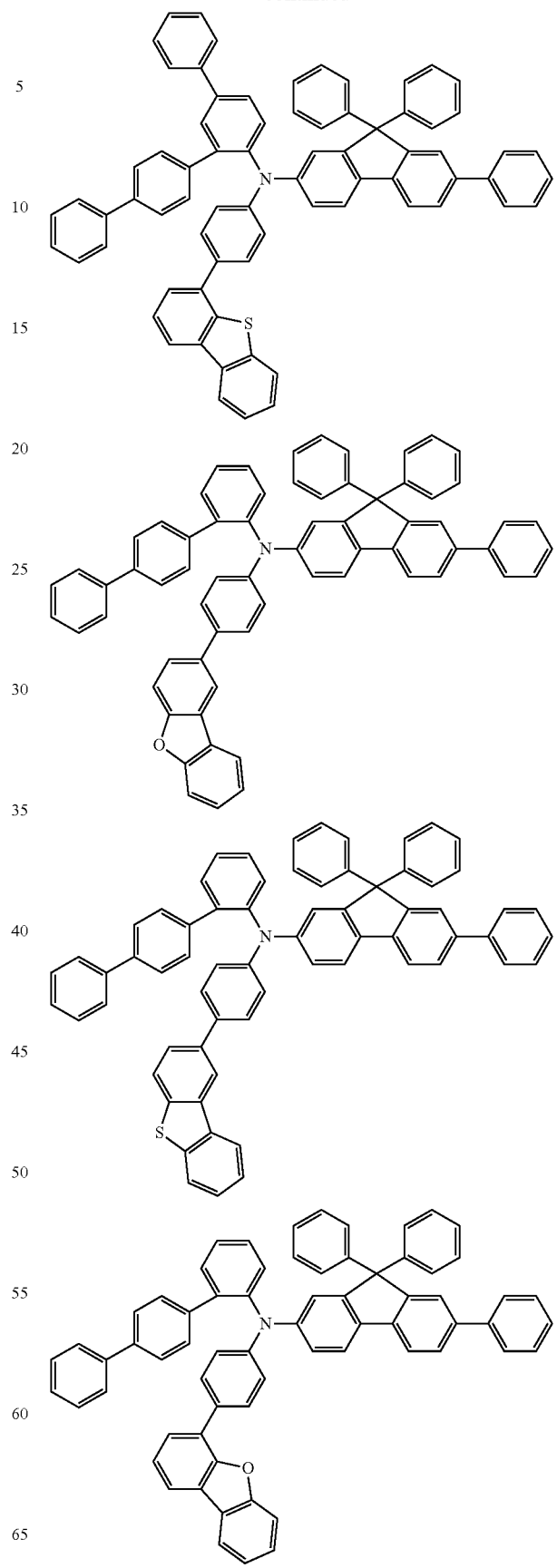

45
-continued
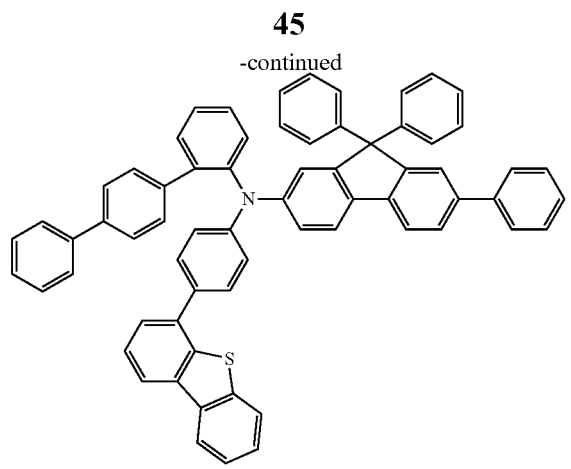
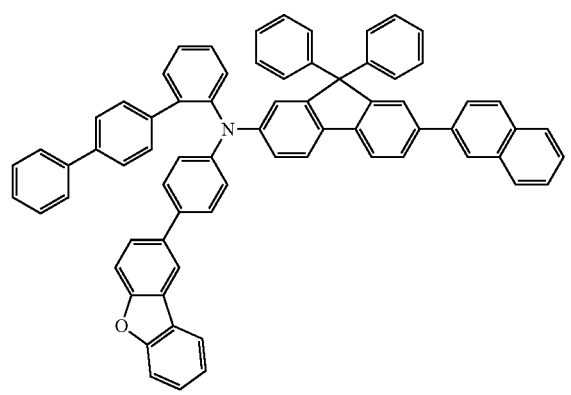
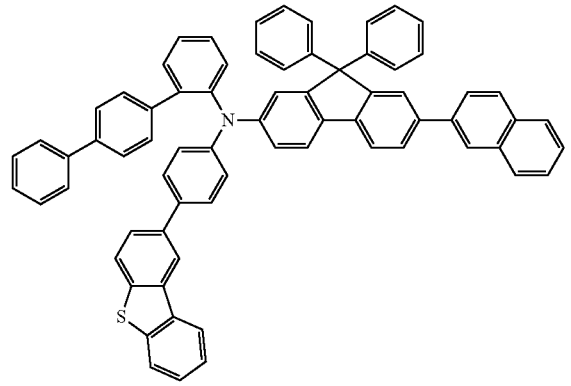
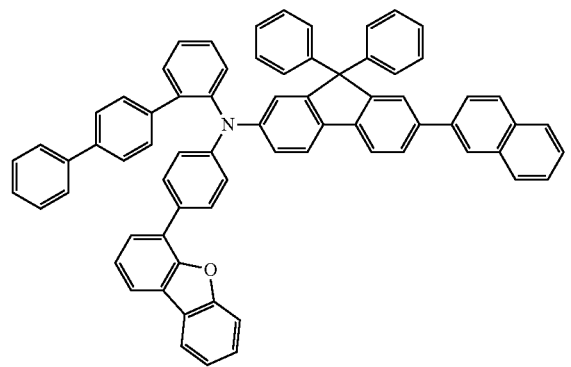
46
-continued
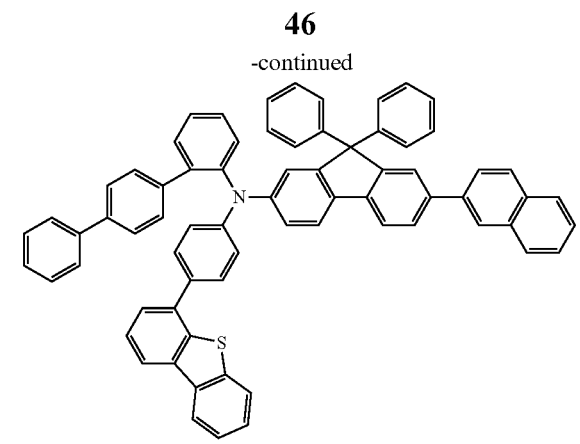
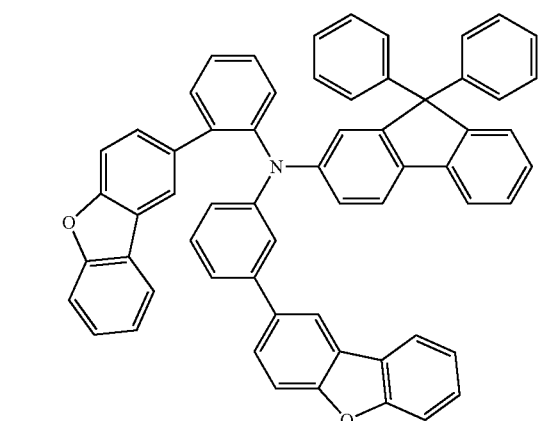
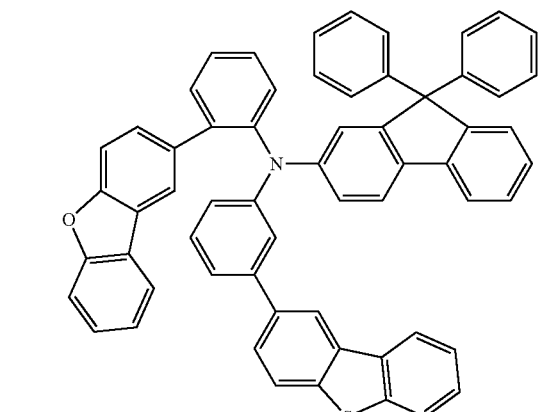
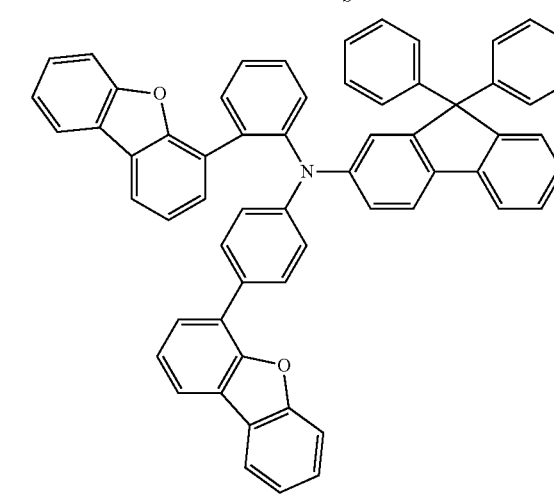

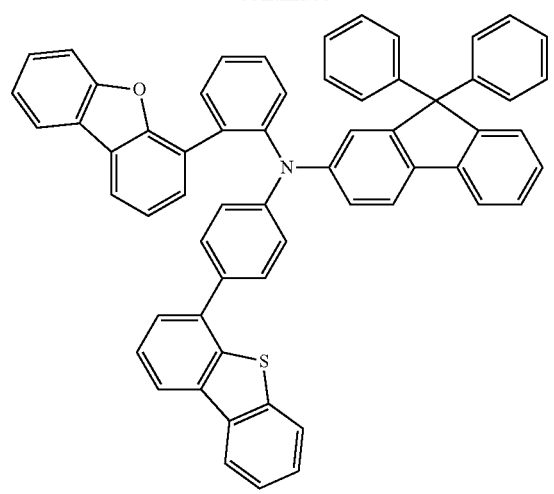
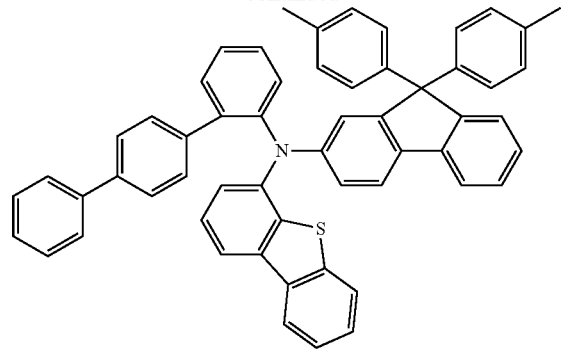
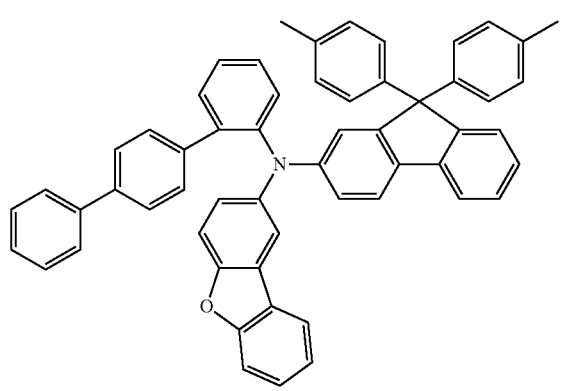
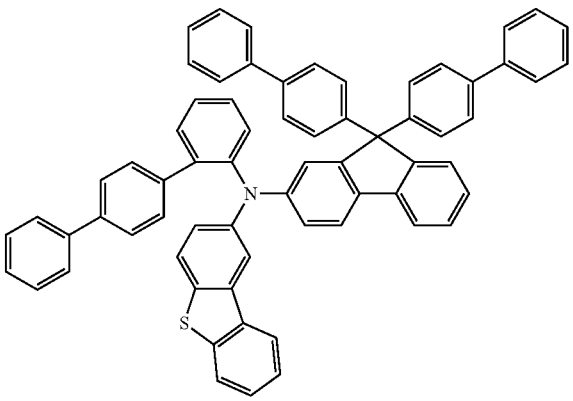
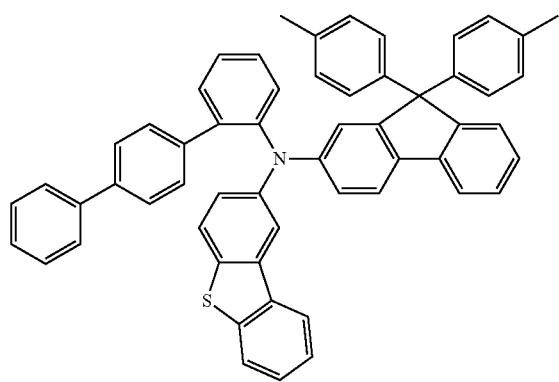
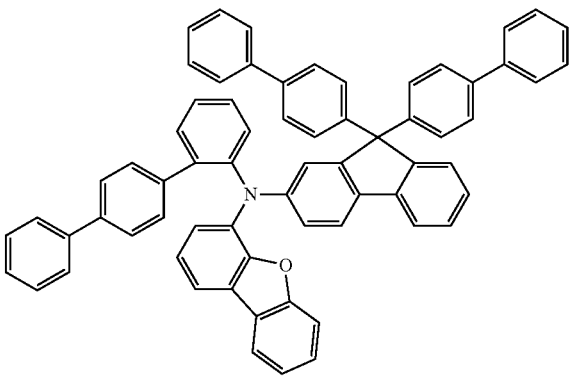
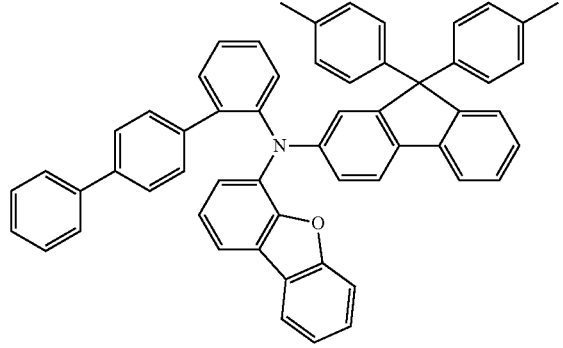

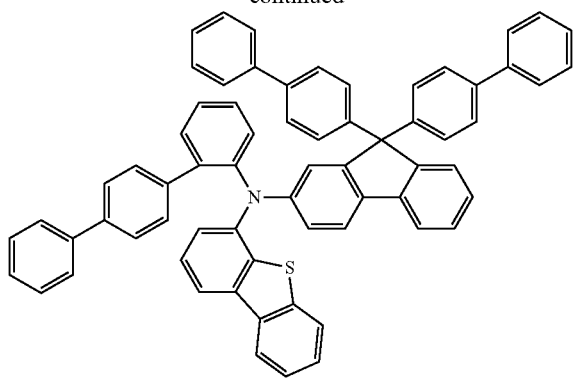
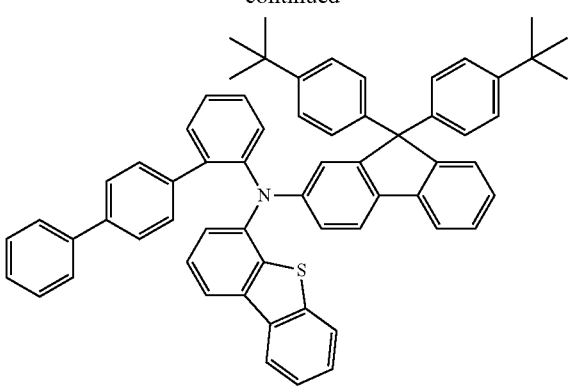

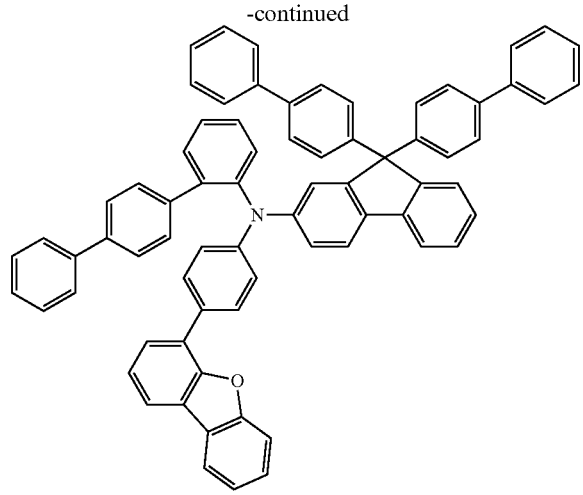
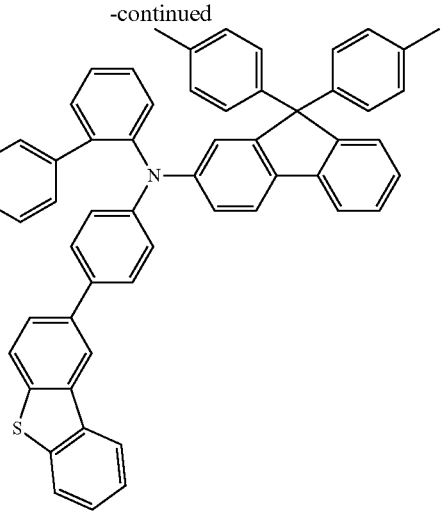
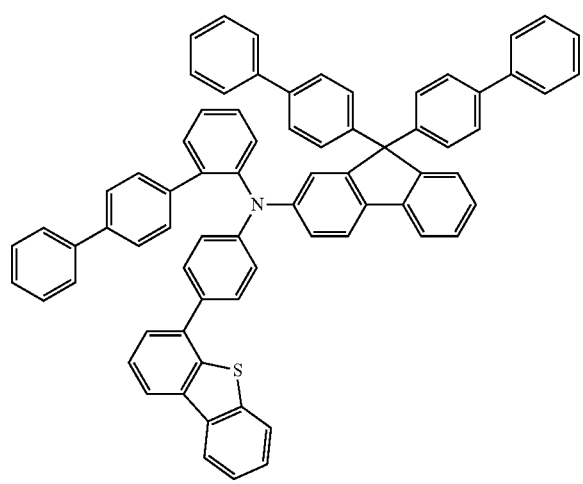
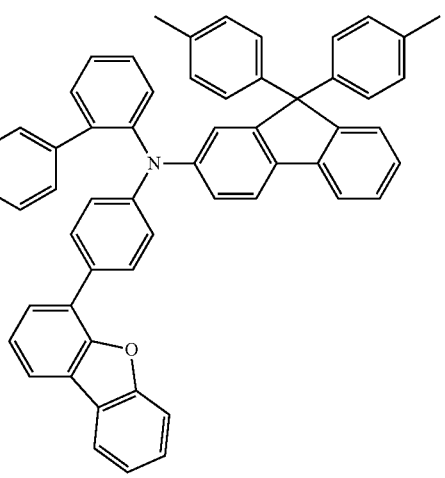
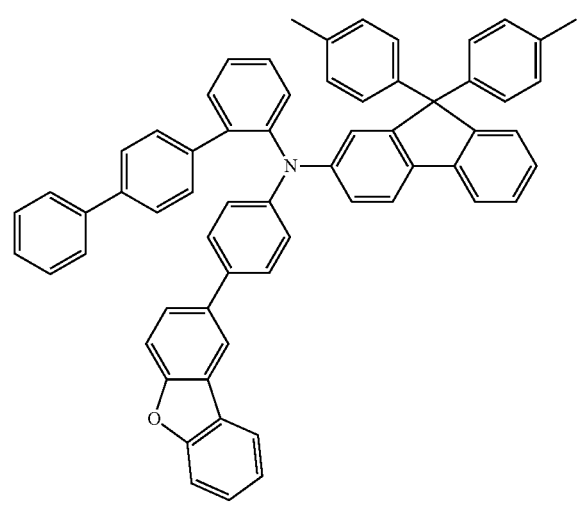
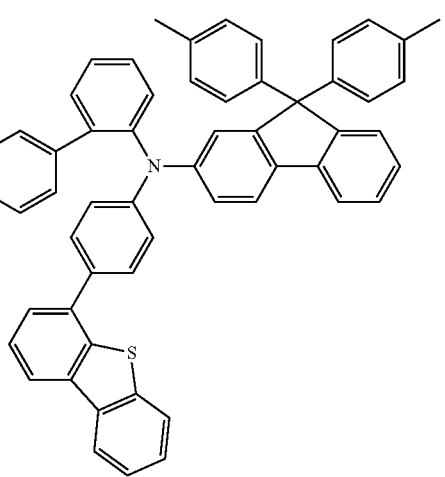

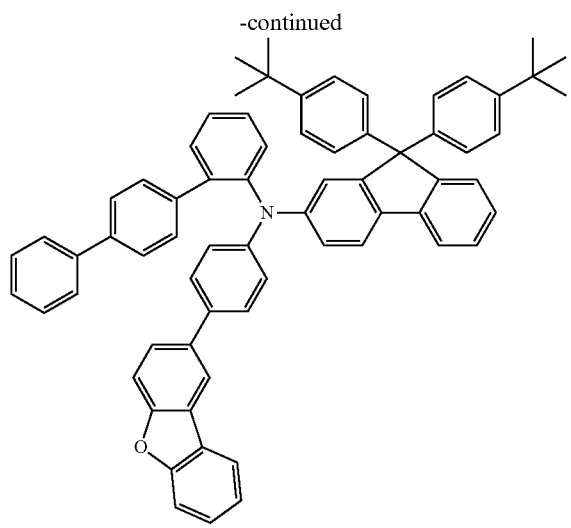
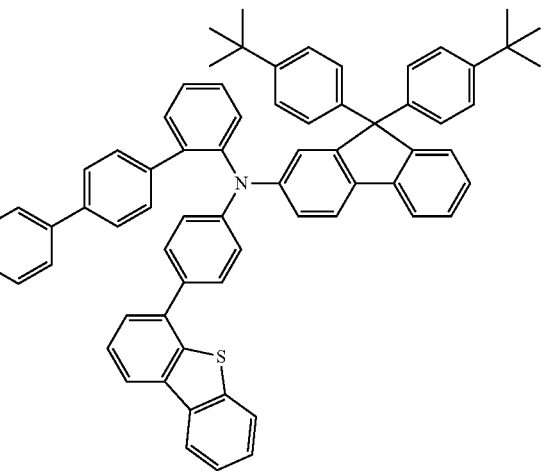
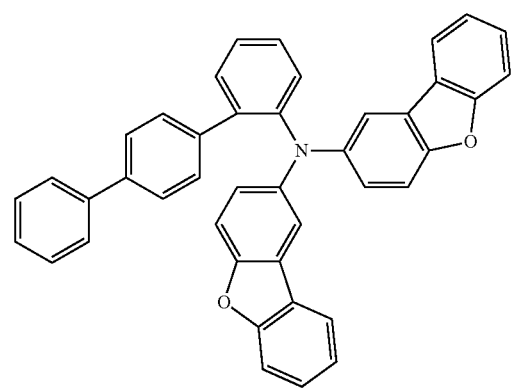
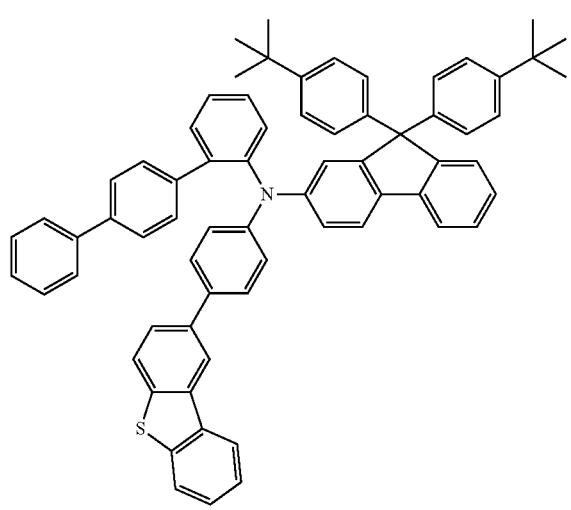
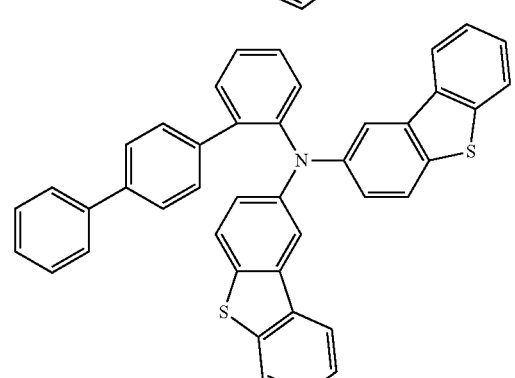
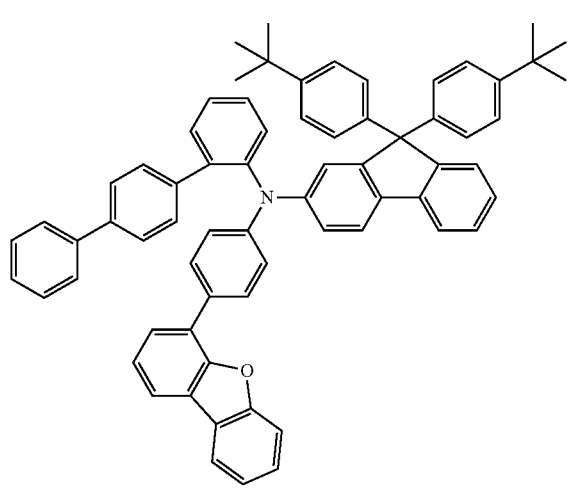
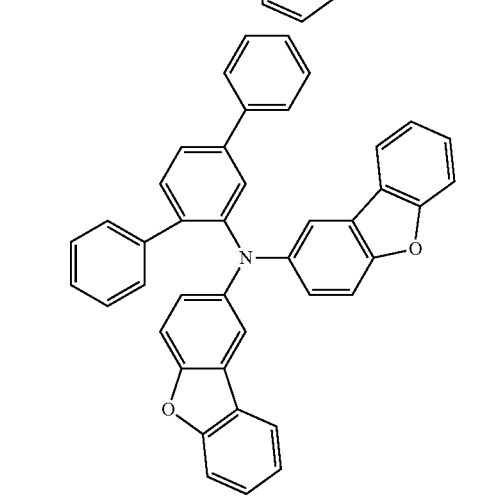

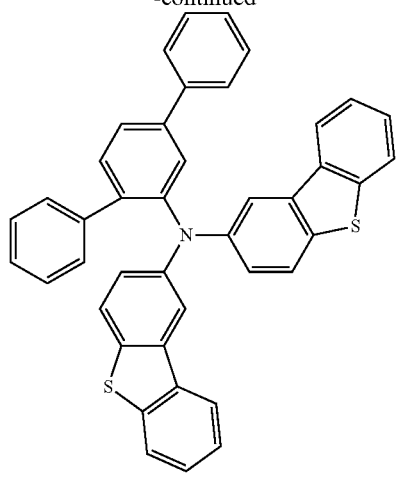
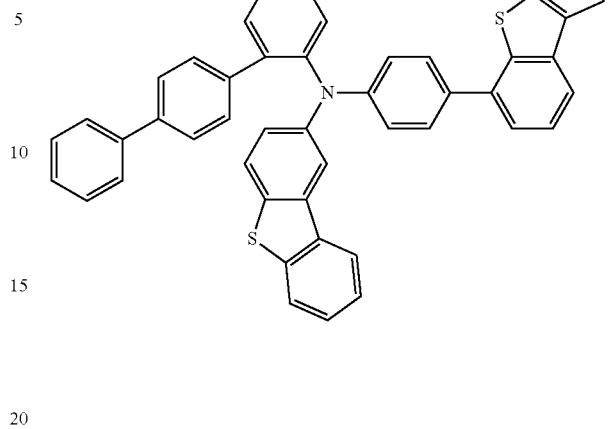
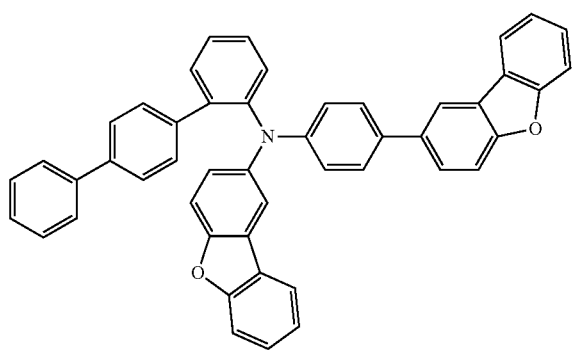
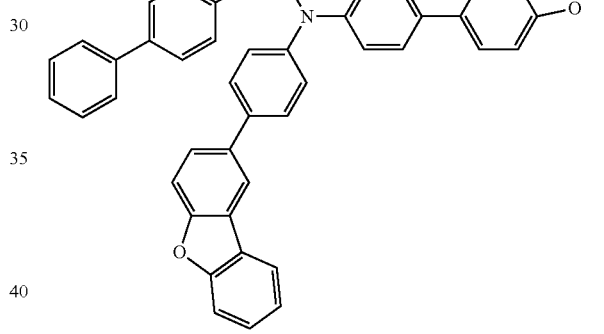
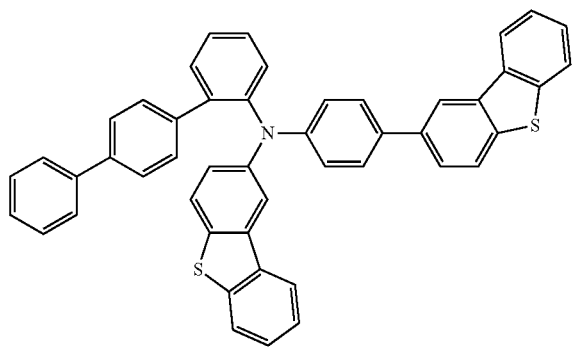
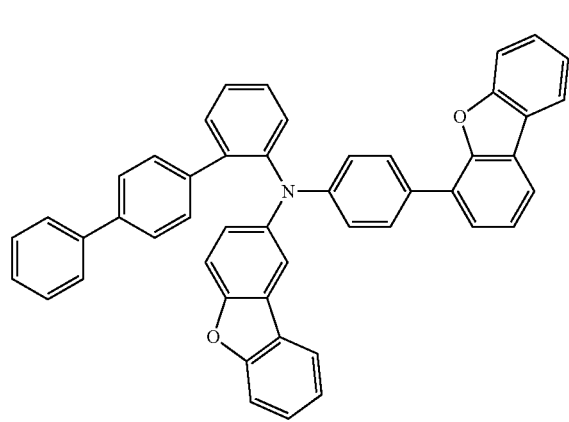
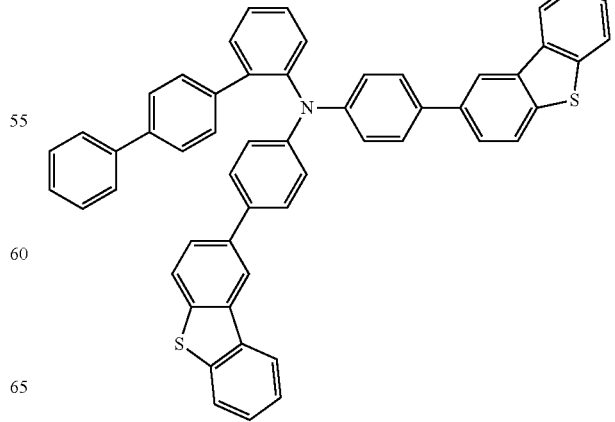

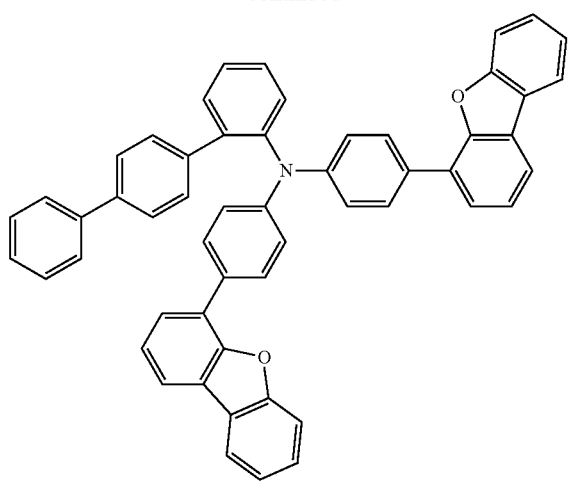
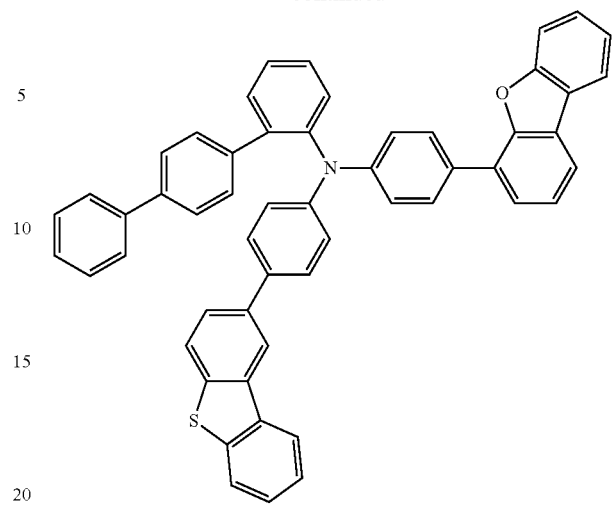
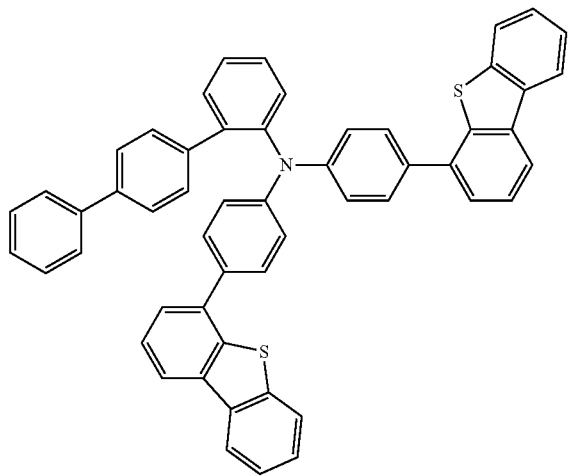
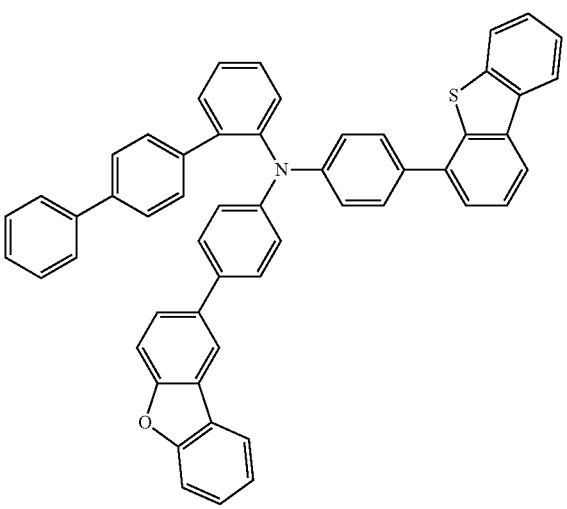
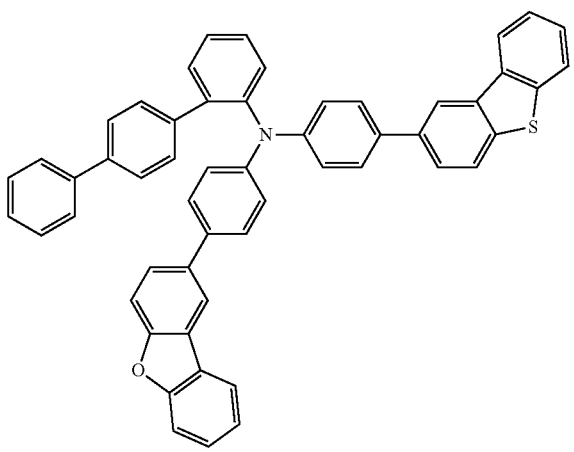
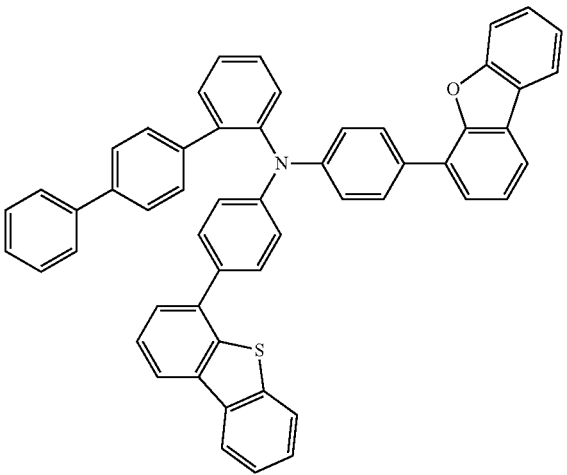

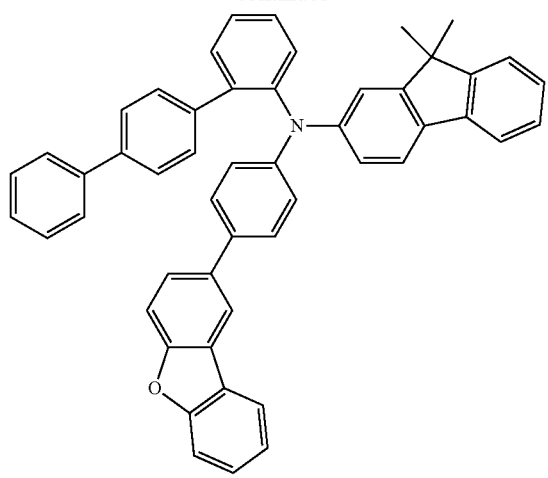
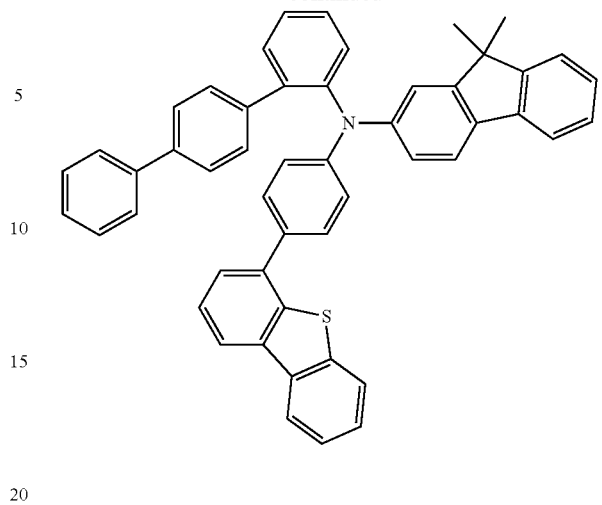
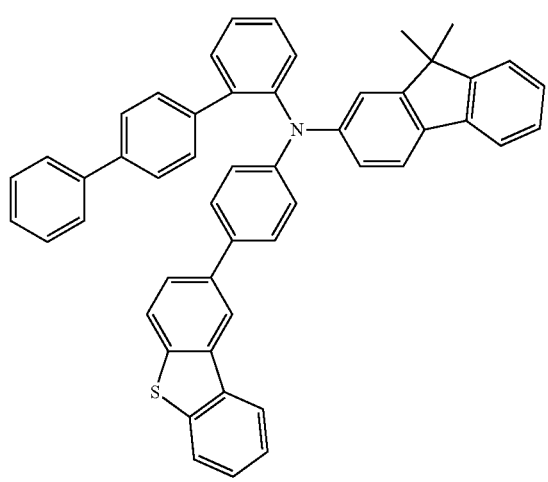
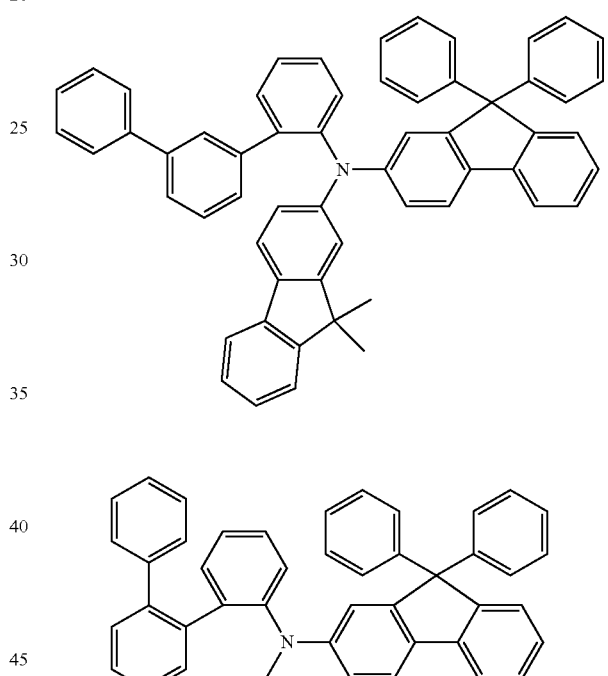
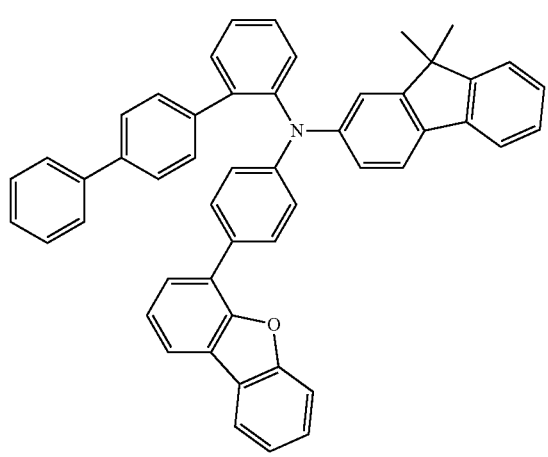

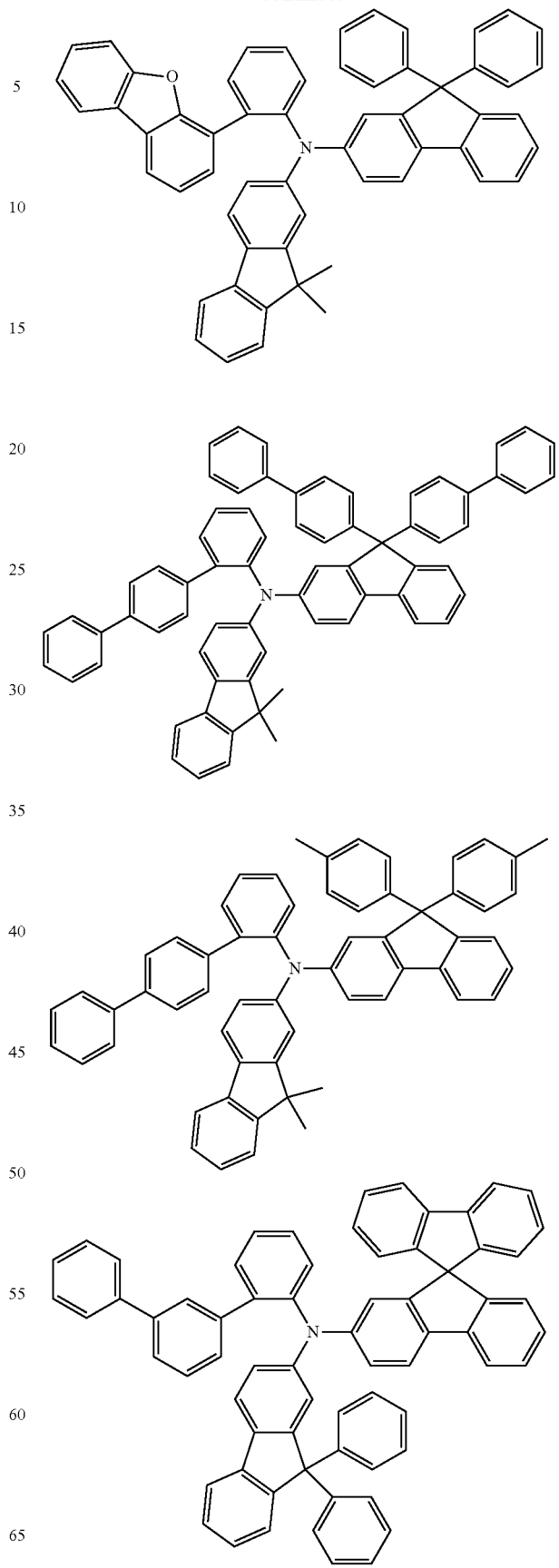
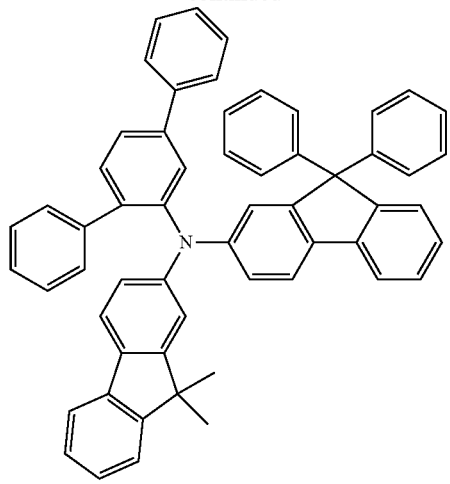

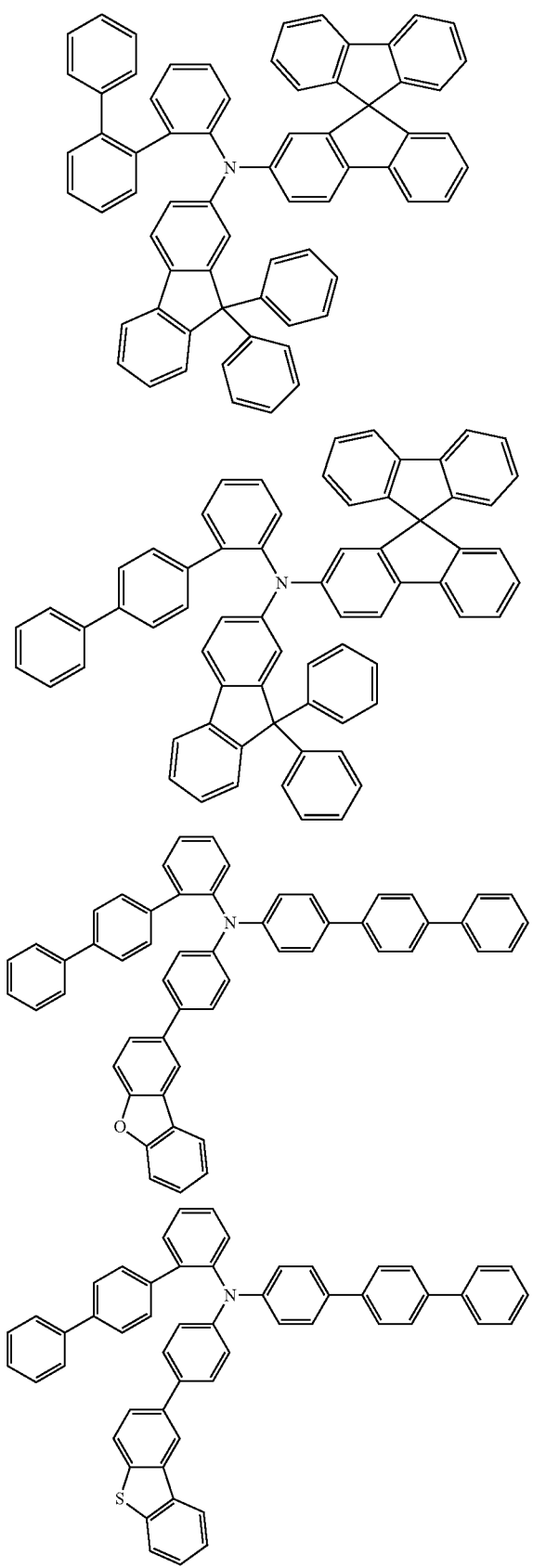
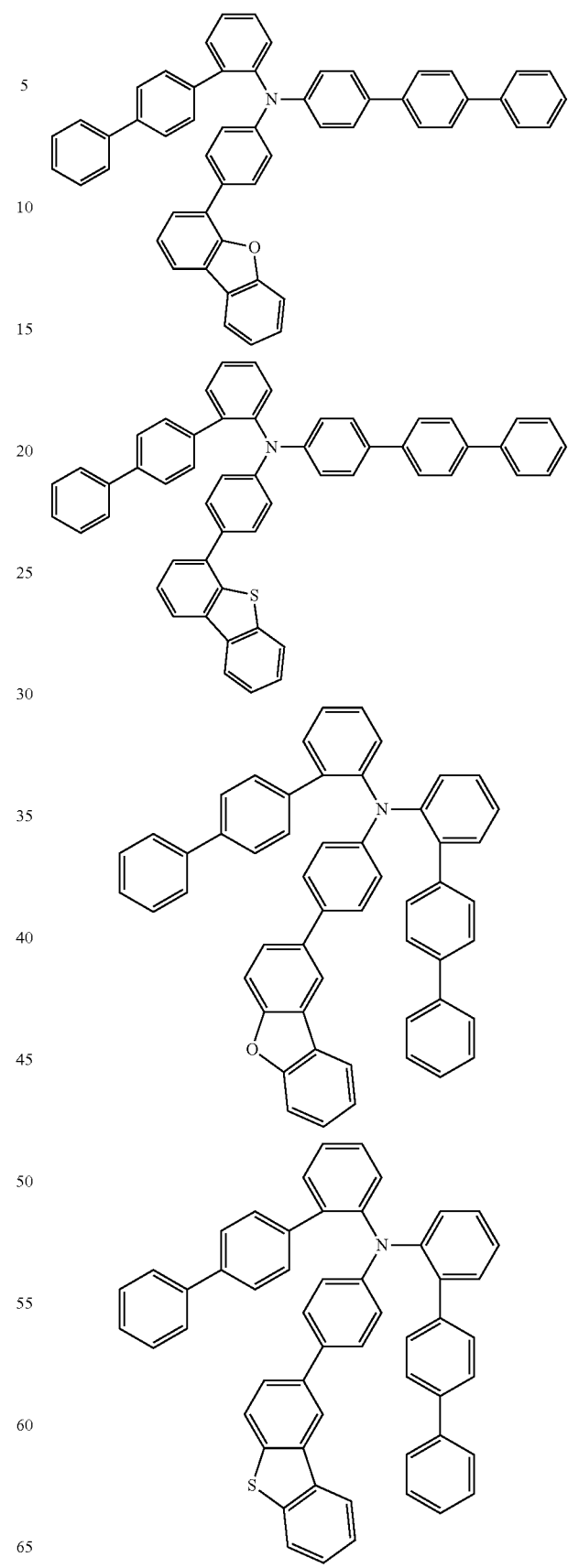

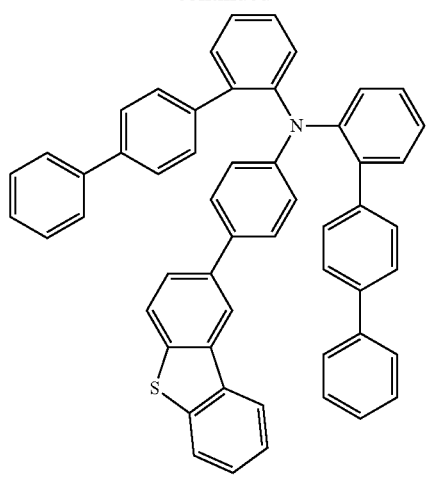
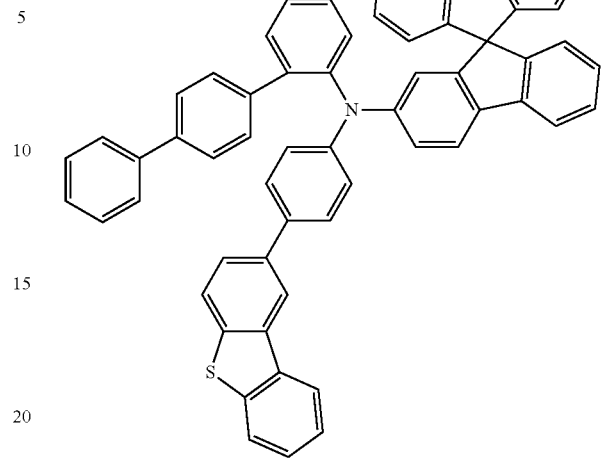
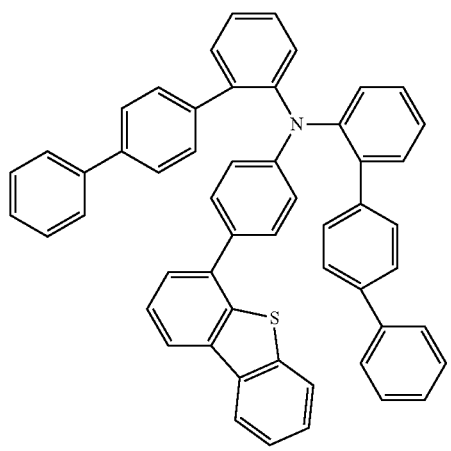
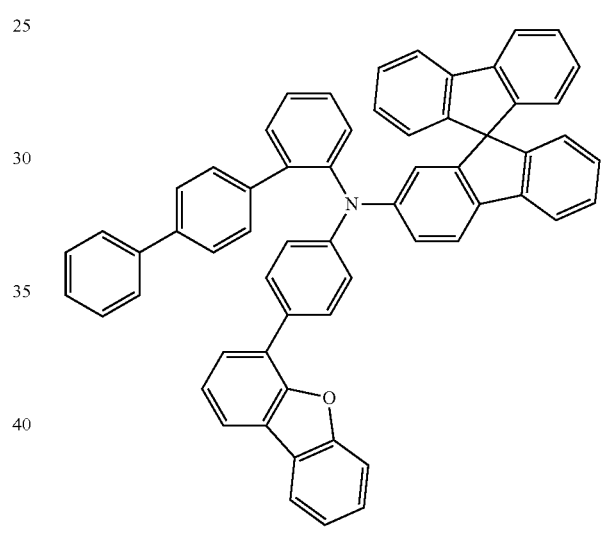
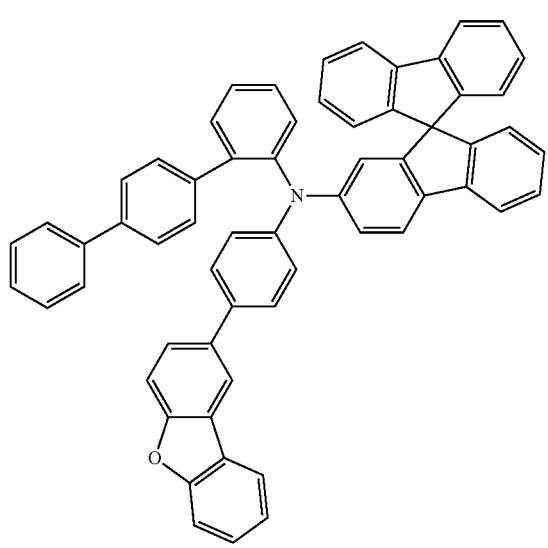
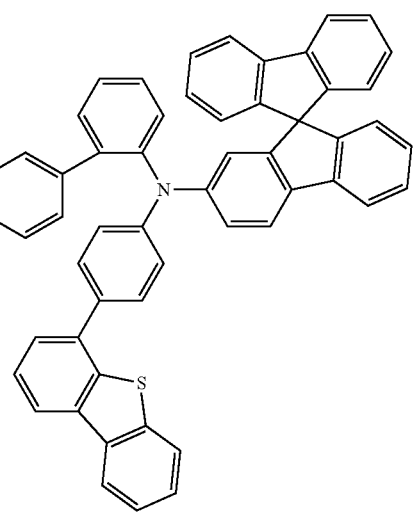

67
-continued
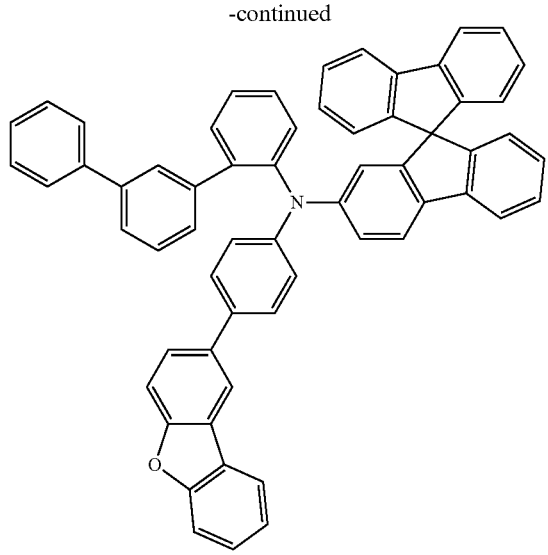
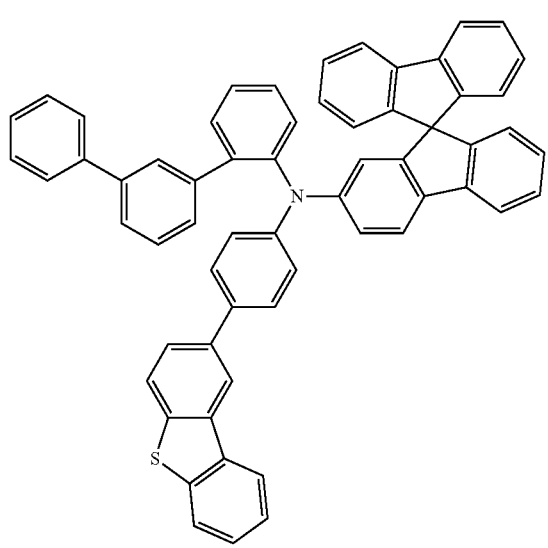
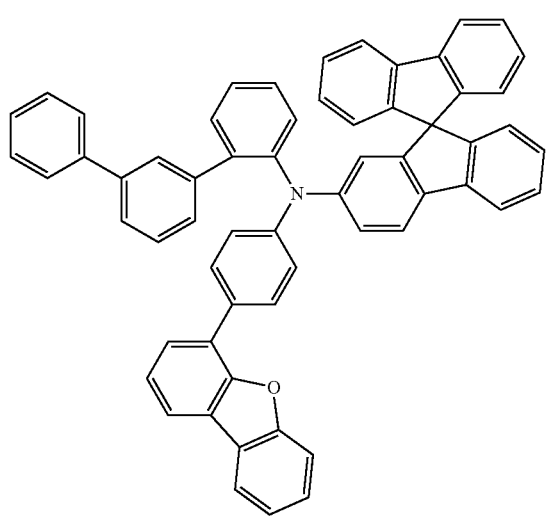
68
-continued
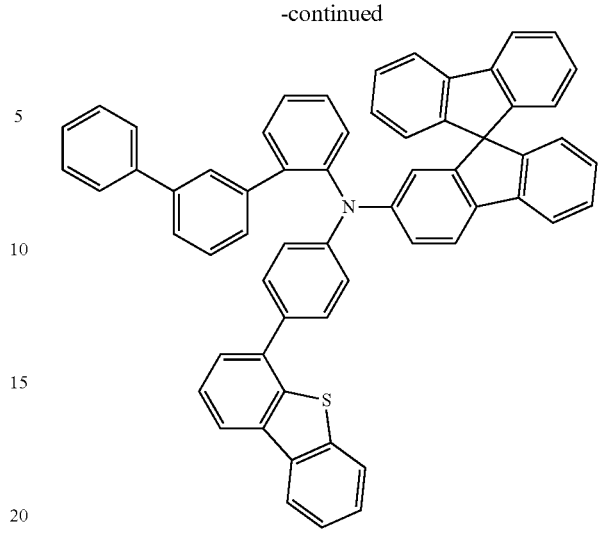
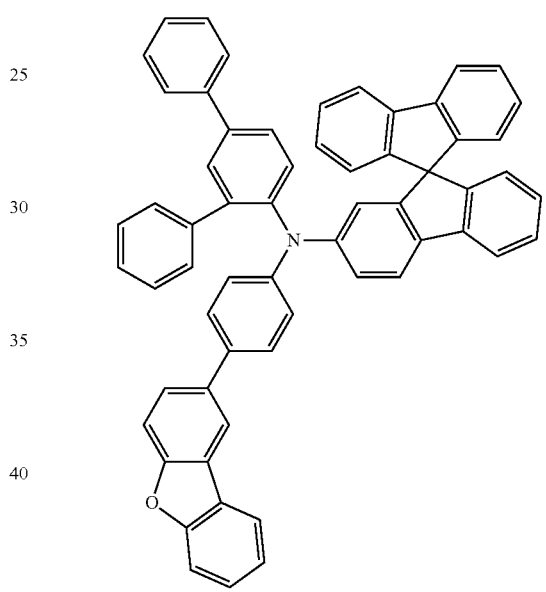
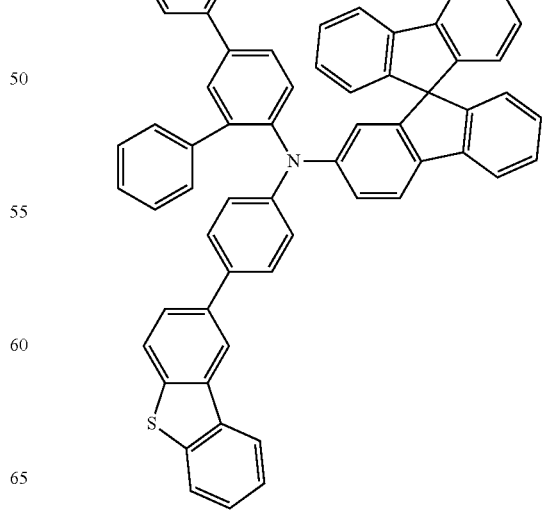

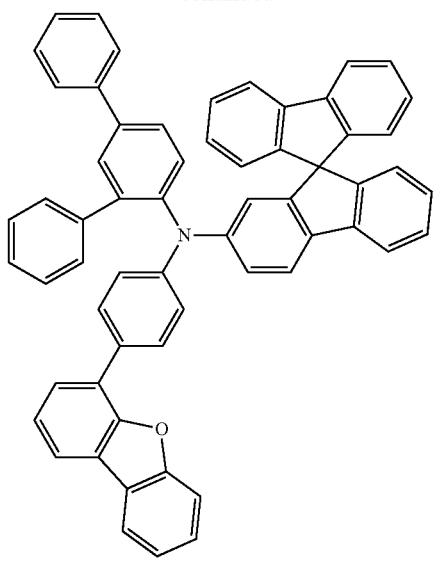
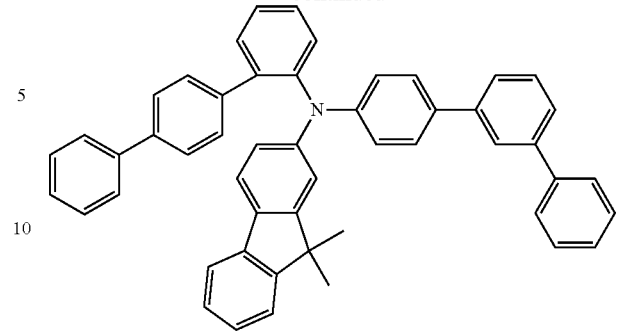
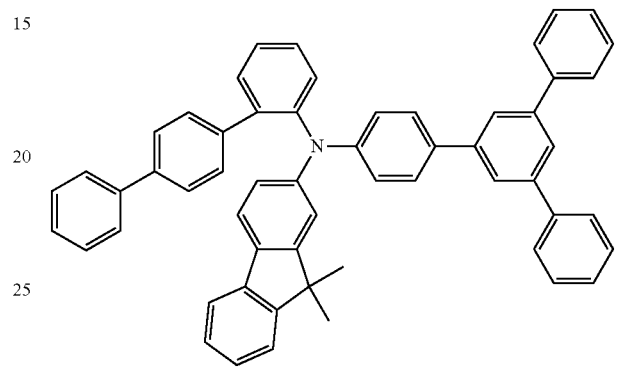
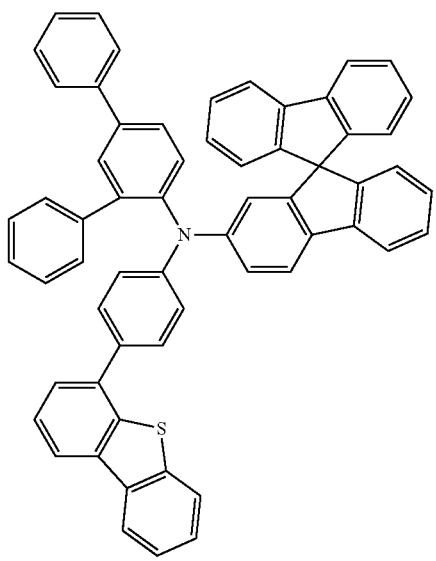
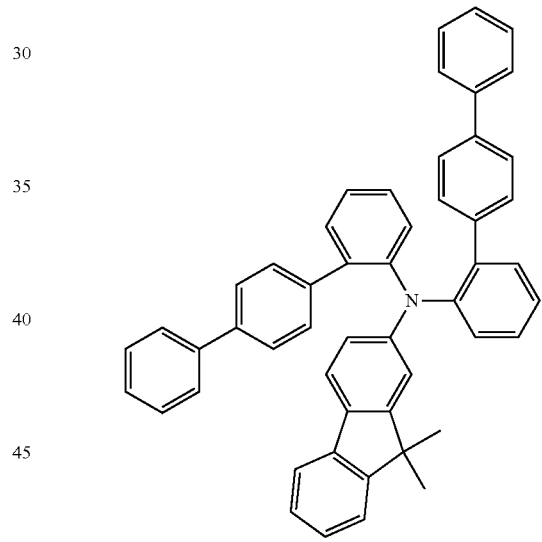
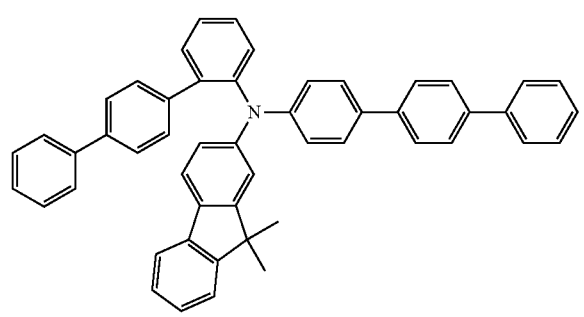
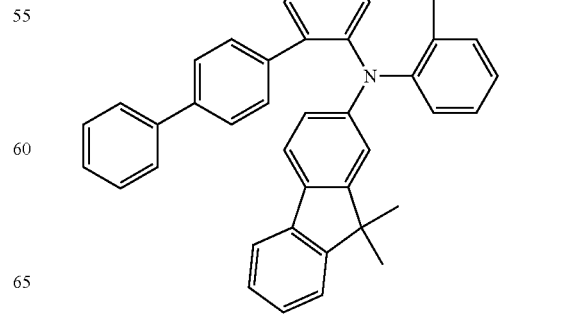

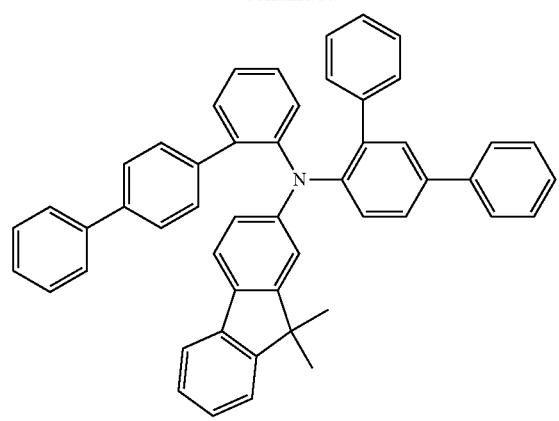
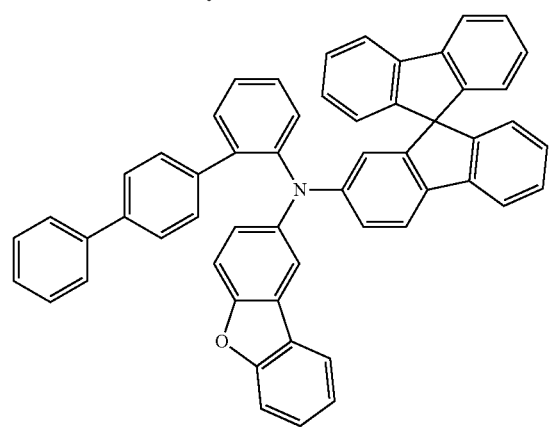
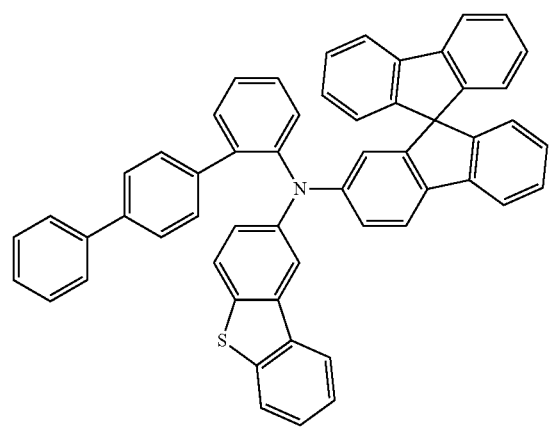
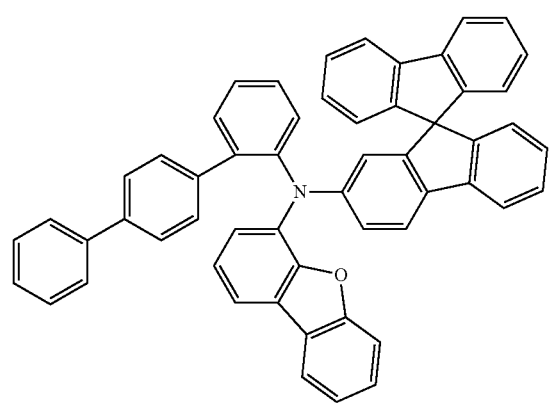
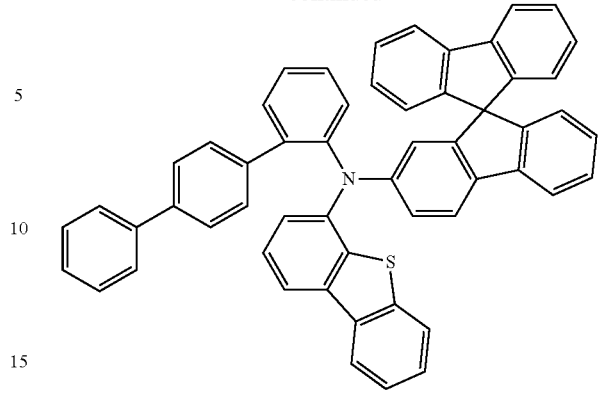
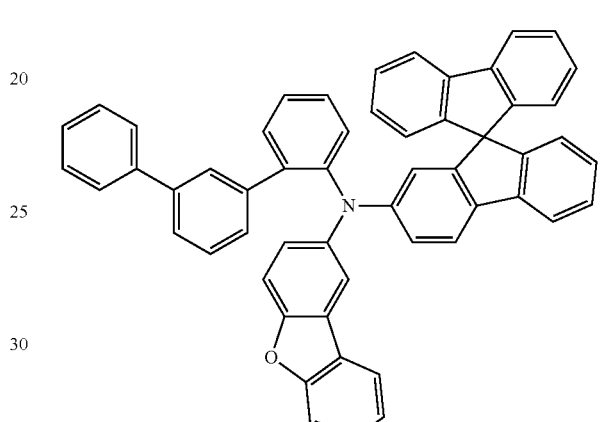
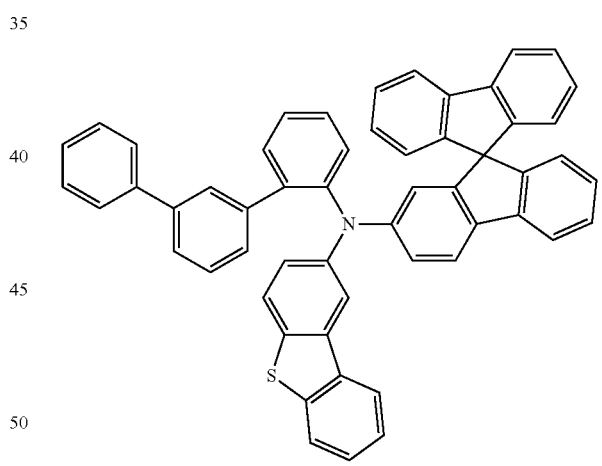
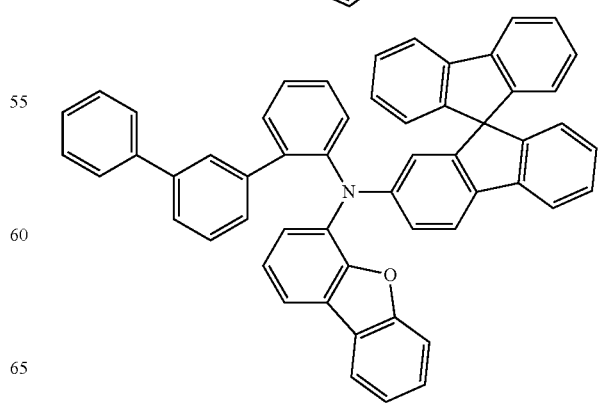

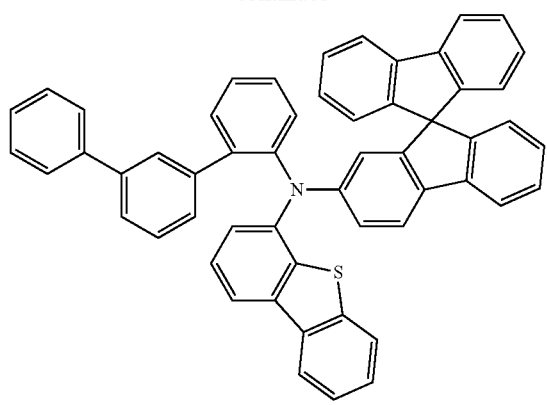

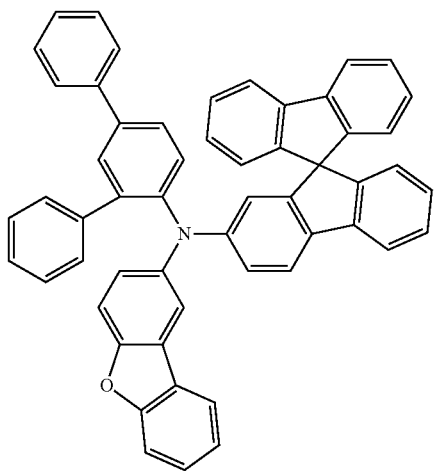

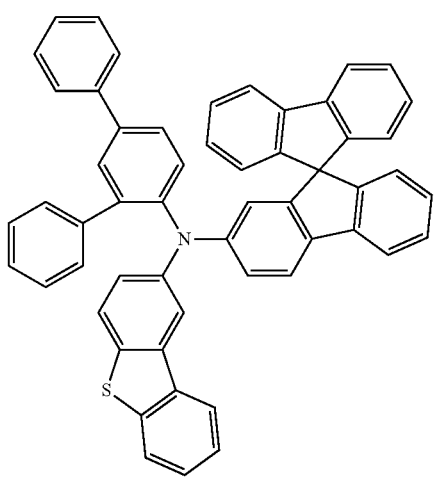

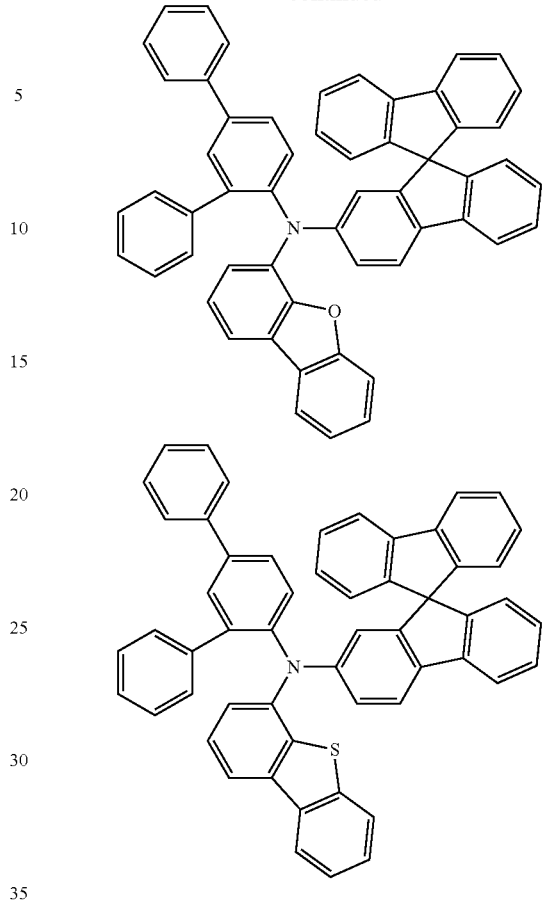

The compound (1) has a high hole mobility.

The compound (1) is useful as a material for organic EL device, a hole transporting material, and a material for an organic thin film layer disposed between an anode and a light emitting layer, such as a hole injecting layer and a hole transporting layer. The production method of the compound (1) is not particularly limited and one of ordinary skill in the art can easily produce it by utilizing or modifying a known synthesis reaction with reference to the examples described below.

The organic EL device in an aspect of the invention will be described below.

Representative device structures (1) to (13) are shown below, although not limited thereto. The device structure (8) is preferably used.

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/(electron transporting layer/) electron injecting layer/cathode;

(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/(electron transporting layer/) electron injecting layer/cathode.

The compound (1) may be used in any of the organic thin film layers of an organic EL device. In view of driving at a lower voltage, the compound (1) is preferably used in a hole injecting layer or a hole transporting layer, more preferably used in a hole transporting layer.

The content of the compound (1) in the organic thin film layer, preferably in a hole injecting layer or a hole transporting layer, is preferably 30 to 100 mol %, more preferably 50 to 100 mol %, still more preferably 80 to 100 mol %, further preferably 95 to 100 mol %, and substantially 100 mol % in a particularly preferred embodiment, each based on the total molar amount of the components in the organic thin film layer.

Each layer will be described below by using an organic EL device wherein the compound (1) is used in a hole transporting layer as an example.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be formed in contact with the anode is formed from a material which is capable of easily injecting holes independently of the work function of the anode. Therefore a material generally used as an electrode material, for example, a metal, an alloy, an electroconductive compound, a mixture thereof, and a group 1 element and a group 2 element of the periodic table are usable.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole-transporting material. The compound (1) may be used in the hole injecting layer alone or in combination with the following compound.

Examples of the highly hole-transporting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrenesulfonic acid) (PEDOT/PSS) and polyalinine/poly(styrenesulfonic acid) (PAni/PSS), is also usable.

Hole Transporting Layer

The hole transporting layer comprises a highly hole-transporting material. The compound (1) may be used in the hole transporting layer alone or in combination with the following compound.

The hole transporting layer may contain an aromatic amine compound, a carbazole derivative, an anthracene derivative, etc., for examples, an aromatic amine compound, such as 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of mainly $10^{-6}$ cm$^2$/Vs or more.

In addition, the hole transporting layer may contain a carbazole derivative, such as CBP, CzPA, and PCzPA, an anthracene derivative, such as t-BuDNA, DNA, and DPAnth, and a macromolecular compound, such as poly(N-vinylcarbazole) (PVK) and poly(4-vinyltriphenylamine) (PVTPA).

Other materials are also usable if their hole transporting ability is higher than their electron transporting ability. The layer comprising a highly hole-transporting material may be a single layer or a laminate of two or more layers each comprising the material mentioned above. For example, the hole transporting layer may be made into a two-layered structure of a first hole transporting layer (anode side) and a second hole transporting layer (cathode side). The compound (1) may be used in either of the first hole transporting layer and the second hole transporting layer.

Guest Material of Light Emitting Layer

The light emitting layer comprises a highly light-emitting material (guest material) and may be formed from a various kind of materials. For example, a fluorescent emitting compound and a phosphorescent emitting compound are usable as the guest material. The fluorescent emitting compound is a compound capable of emitting light from a singlet excited state, and the phosphorescent emitting compound is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N, N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N, C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the guest material mentioned above in another material (host material). The host material may be selected from various kinds of materials and is preferably a material having a lowest unoccupied molecular orbital level (LUMO level) higher than that of the guest material and a highest occupied molecular orbital level (HOMO level) lower than that of the guest material.

The host material may include, for example,
(1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:
a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato) aluminum(III) (BAlq), bis(8-quinolinolato)zinc(II) (Znq), bis[2-(2-benzoxazolyl)phenolato]zinc(II) (ZnPBO), and bis [2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), NPB (or α-NPD), TPD, DFLDPBi, and BSPB.

The host material may be used alone or in combination of tow or more.

Electron Transporting Layer

The electron transporting layer comprises a highly electron-transporting material, for example, (1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the low molecular organic compound include a metal complex, such as Alq, tris(4-methyl-8-quinolinolato)aluminum (Almq$_3$), bis(10-hydroxybenzo[h]quinolinato)beryllium (BeBq$_2$), BAlq, Znq, ZnPBO, and ZnBTZ; and a heteroaromatic compound, such as 2-(4-biphenylyl)-5-(4-tert-butylphenyl)-1,3,4-oxadiazole (PBD), 1,3-bis[5-(ptert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

The above compounds have an electron mobility of mainly $10^{-6}$ cm$^2$/Vs or more. Other materials are also usable in the electron transporting layer if their electron transporting ability is higher than their hole transporting ability. The electron transporting layer may be a single layer or a laminate of two or more layers each comprising the material mentioned above.

A macromolecular compound is also usable in the electron transporting layer. Examples there of include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride(CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

A protective layer may be formed on the surface of an organic EL device in view of improving the stability against temperature, moisture, surrounding atmosphere, etc. The organic EL device may be wholly protected by a silicone oil, a resin, etc.

Each layer of the organic EL device is formed by a dry film-forming method, such as vacuum vapor deposition, sputtering, plasma, and ion plating, and a wet film-forming method, such as spin coating, dip coating, and flow coating.

In the wet film-forming method, the material for each layer is dissolved or dispersed in a suitable solvent, such as ethanol, chloroform, tetrahydrofuran, and dioxane, and then the obtained solution or dispersion is made into a film. To improve the film-forming properties and prevent pin holes on the film, the solution and the dispersion may include a resin or an additive. Examples of the resin include an insulating resin and a copolymer thereof, such as polystyrene, polycarbonate, polyarylate, polyester, polyamide, polyurethane, polysulfone, polymethyl methacrylate, polymethyl acrylate, and cellulose; a photoconductive resin, such as poly-N-vinylcarbazole and polysilane; and an electroconductive resin, such as polythiophene and polypyrrole. Examples of the additive include an antioxidant, an ultraviolet absorber, and a plasticizer.

The thickness of each layer is not particularly limited and selected so as to obtain a good device performance. If extremely thick, a large applied voltage is needed to obtain a desired emission output, thereby reducing the efficiency. If extremely thin, pinholes occur on the film to make it difficult to obtain a sufficient luminance even when applying an electric field. The thickness is generally 5 nm to 10 μm and preferably 10 nm to 0.2 μm.

The organic EL device comprising the compound (1) is applicable to electronic equipment, for example, a display part, such as an organic EL panel module; a display device of television set, mobile phone, personal computer, etc.; and a light emitting source of lighting equipment and vehicle lighting equipment.

EXAMPLES

The present invention will be descried below in more detail with reference to the examples. However, it should be noted that the scope of the present invention is not limited thereto.

Intermediate Synthesis 1-1; Synthesis of Intermediate 1-1

Under an argon atmosphere, into a mixture of 28.3 g (100.0 mmol) of 4-iodobromobenzene, 22.3 g (105.0 mmol) of dibenzofuran-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added. The obtained mixture was refluxed for 10 h under heating and stirring.

After the reaction, the reaction mixture was cooled to room temperature and extracted with dichloromethane in a separating funnel. The organic layer was dried over MgSO$_4$, filtered, and then concentrated. The residual concentrate was purified by silica gel column chromatography to obtain 26.2 g of a white solid, which was identified by FD-MS analysis (field desorption mass spectrometry) as the following intermediate 1-1 (yield: 81%).

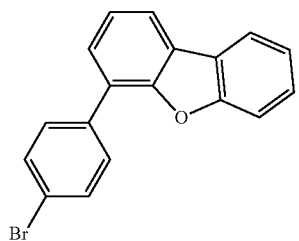

Intermediate 1-1

Intermediate Synthesis 1-2: Synthesis of intermediate 1-2

Under a nitrogen atmosphere, 150 g (0.89 mol) of dibenzofuran was dissolved in 1000 ml of acetic acid under heating. After further adding 188 g (1.18 mol) of bromine dropwise, the resultant solution was stirred at room temperature for 20 h. The precipitated crystal was collected by filtration and successively washed with acetic acid and water. The obtained crude product was recrystallized from methanol several times to obtain 66.8 g of a white crystal, which was identified by FD-MS analysis as the following intermediate 1-2 (yield: 30%).

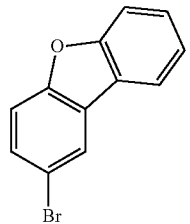

Intermediate 1-2

Intermediate Synthesis 1-3: Synthesis of intermediate 1-3

Under an argon atmosphere, a solution of 24.7 g (100.0 mmol) of the intermediate 1-2 in 400 ml of dehydrated tetrahydrofuran was cooled to −40° C., and then 63 ml (100.0 mmol) of a 1.6 M hexane solution of n-butyllithium was gradually added. After stirring for one hour under heating to 0° C., the reaction solution was again cooled to −78° C. and a solution of 26.0 g (250.0 mmol) of trimethyl borate in 50 ml of dehydrated tetrahydrofuran was added dropwise. After the addition, the reaction solution was stirred at room temperature for 5 h. After adding 200 ml of a 1 N hydrochloric acid, the solution was stirred for one hour and then the aqueous layer was removed. The organic layer was dried over MgSO$_4$ and the solvent was evaporated off under reduced pressure. The obtained solid was washed with toluene to obtain 15.2 g of a white crystal, which was identified by FD-MS analysis as the following intermediate 1-3 (yield: 72%).

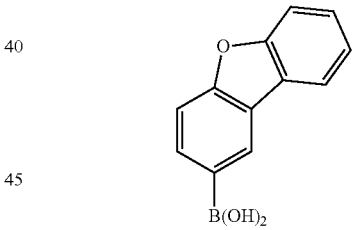

Intermediate 1-3

Intermediate Synthesis 1-4: Synthesis of intermediate 1-4

Under an argon atmosphere, into a mixture of 28.3 g (100.0 mmol) of 4-iodobromobenzene, 22.3 g (105.0 mmol) of the intermediate 1-3, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added. The obtained mixture was refluxed for 10 h under heating and stirring.

After the reaction, the reaction mixture was extracted with dichloromethane in a separating funnel. The organic layer was dried over MgSO$_4$, filtered, and then concentrated. The residual concentrate was purified by silica gel column chromatography to obtain 24.2 g of a white solid, which was identified by FD-MS analysis as the following intermediate 1-4 (yield: 75%).

Intermediate 1-4

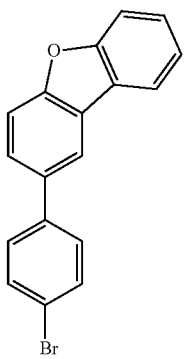

Intermediate 2-1

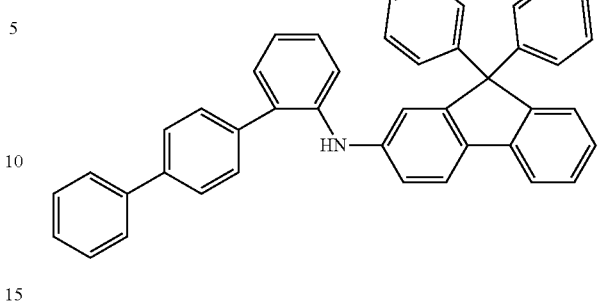

Intermediate Synthesis 1-5: Synthesis of intermediate 1-5

Under an argon atmosphere, into a mixture of 28.3 g (100.0 mmol) of 4-iodobromobenzene, 23.9 g (105.0 mmol) of dibenzothiophene-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added. The obtained mixture was refluxed for 10 h under heating and stirring.

After the reaction, the reaction mixture was cooled to room temperature and extracted with dichloromethane in a separating funnel. The organic layer was dried over MgSO$_4$, filtered, and then concentrated. The residual concentrate was purified by silica gel column chromatography to obtain 27.1 g of a white solid, which was identified by FD-MS analysis as the following intermediate 1-5 (yield: 80%).

Intermediate Synthesis 2-2: Synthesis of intermediate 2-2

In the same manner as in Intermediate Synthesis 2-1 except for using [1,1':3',1"]terphenyl-2-ylamine in place of [1,1':4',1"]terphenyl-2-ylamine, 21.1 g of a white solid was obtained, which was identified by FD-MS analysis as the following intermediate 2-2 (yield: 75%).

Intermediate 2-2

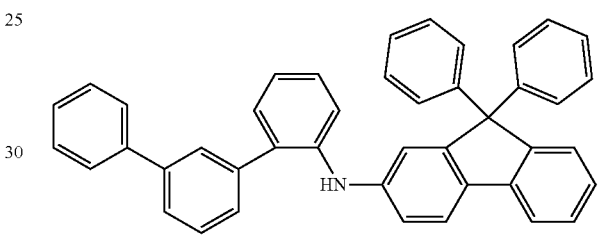

Intermediate Synthesis 2-3: Synthesis of intermediate 2-3

In the same manner as in Intermediate Synthesis 2-1 except for using [1,1':4',1"]terphenyl-3'-ylamine in place of [1,1':4',1"]terphenyl-2-ylamine, 19.7 g of a white solid was obtained, which was identified by FD-MS analysis as the following intermediate 2-3 (yield: 70%).

Intermediate 1-5

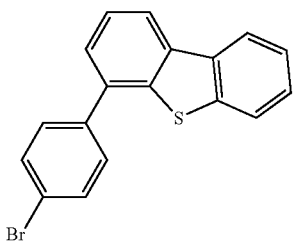

Intermediate 2-3

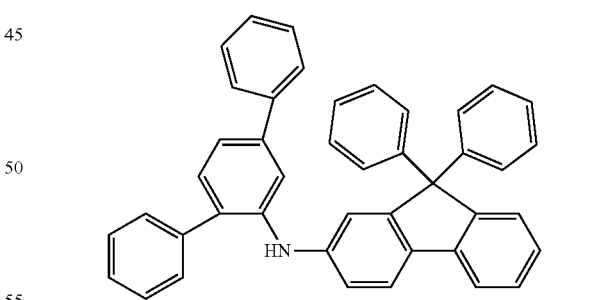

Intermediate Synthesis 2-1: Synthesis of intermediate 2-1

Under an argon atmosphere, into a mixture of 19.9 g (50.0 mmol) of 2-bromo-9,9'-diphenylfluorene, 12.3 g (50.0 mmol) of [1,1':4',1"]terphenyl-2-ylamine, and 9.6 g (100.0 mmol) of sodium t-butoxide, 250 ml of dehydrated toluene was added, and the resultant mixture was stirred. After adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the crystal collected by filtration was dried to obtain 19.7 g of a white solid, which was identified by FD-MS analysis as the following intermediate 2-1 (yield: 70%).

Synthesis Example 1

Production of Compound (H1)

Under an argon atmosphere, into a mixture of 2.5 g (10.0 mmol) of the intermediate 1-2, 5.6 g (10.0 mmol) of the intermediate 2-1, 0.14 g (0.15 mmol) of Pd$_2$(dba)$_3$, 0.087 g (0.3 mmol) of P(tBu)$_3$HBF$_4$, and 1.9 g (20.0 mmol) of sodium t-butoxide, 50 ml of dehydrated xylene was added. The resultant mixture was refluxed for 8 h under heating.

After the reaction, the reaction mixture was cooled to 50° C., filtered through celite/silica gel, and the filtrate was concentrated. The residual concentrate was purified by silica gel column chromatography to obtain a white solid. The crude product was recrystallized from toluene to obtain 3.6 g of a white crystal, which was identified by FD-MS analysis as the following compound (H1) (yield: 50%).

Compound (H1)

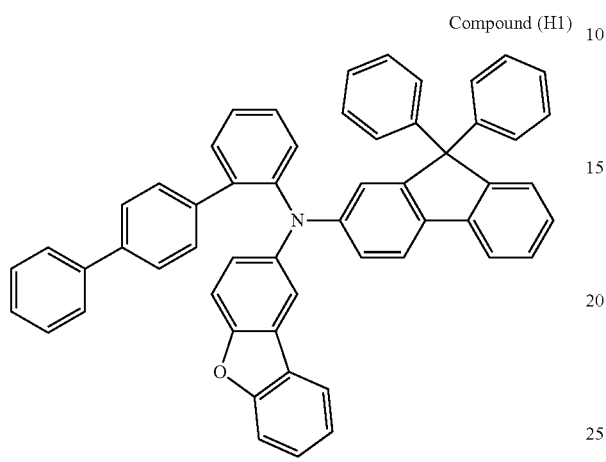

Synthesis Example 2

Production of Compound (H2)

In the same manner as in Synthesis Example 1 except for using 3.2 g of the intermediate 1-4 in place of the intermediate 1-2, 5.1 g of a white crystal was obtained, which was identified by FD-MS analysis as the following compound (H2) (yield: 63%).

Compound (H2)

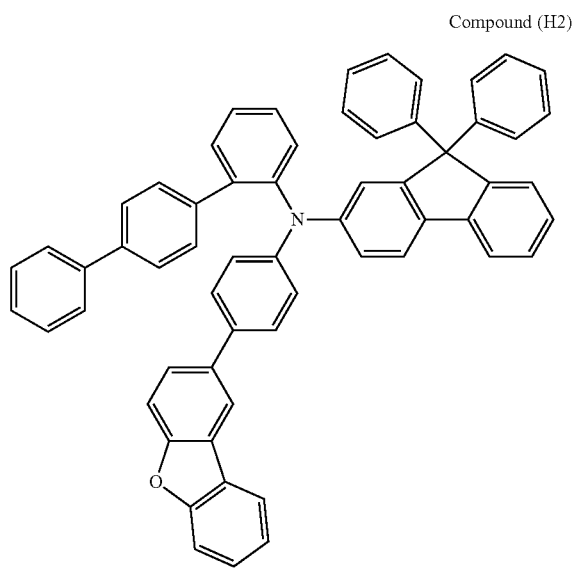 [SMILES: c1ccc(-c2ccc(-c3ccccc3N(c3ccc(-c4ccc5oc6ccccc6c5c4)cc3)c3ccc4c(c3)C(c3ccccc3)(c3ccccc3)c3ccccc3-4)cc2)cc1]

Synthesis Example 3

Production of Compound (H3)

In the same manner as in Synthesis Example 1 except for using 3.4 g of the intermediate 1-5 in place of the intermediate 1-2, 4.1 g of a white crystal was obtained, which was identified by FD-MS analysis as the following compound (H3) (yield: 50%).

Compound (H3)

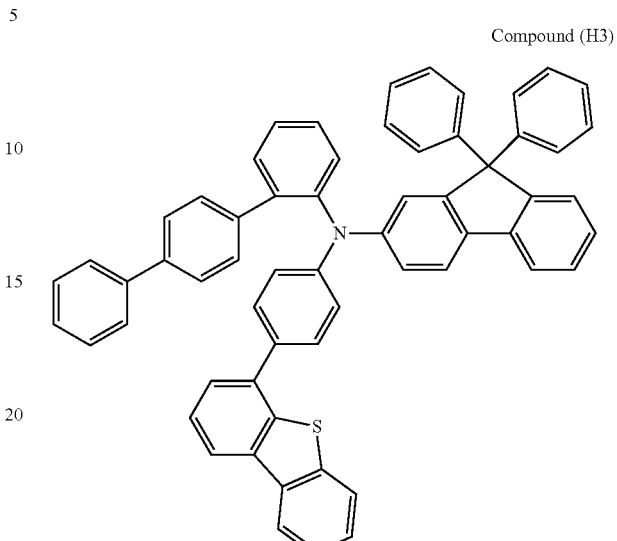

Synthesis Example 4

Production of Compound (H4)

In the same manner as in Synthesis Example 1 except for using 3.2 g of the intermediate 1-1 in place of the intermediate 1-2 and using 5.6 g of the intermediate 2-2 in place of the intermediate 2-1, 4.4 g of a white crystal was obtained, which was identified by FD-MS analysis as the following compound (H4) (yield: 55%).

Compound (H4)

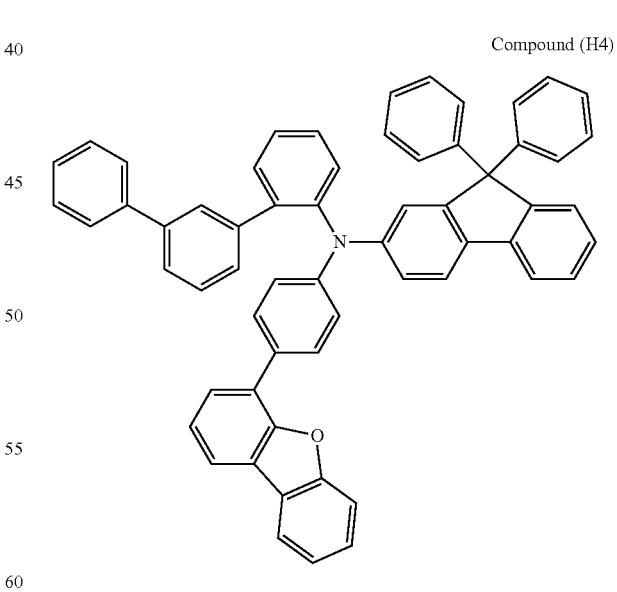

Synthesis Example 5

Production of Compound (H5)

In the same manner as in Synthesis Example 1 except for using 3.2 g of the intermediate 1-1 in place of the intermediate 1-2 and using 5.6 g of the intermediate 2-3 in place of the intermediate 2-1, 4.4 g of a white crystal was obtained, which was identified by FD-MS analysis as the following compound (H5) (yield: 55%).

Compound (H5)

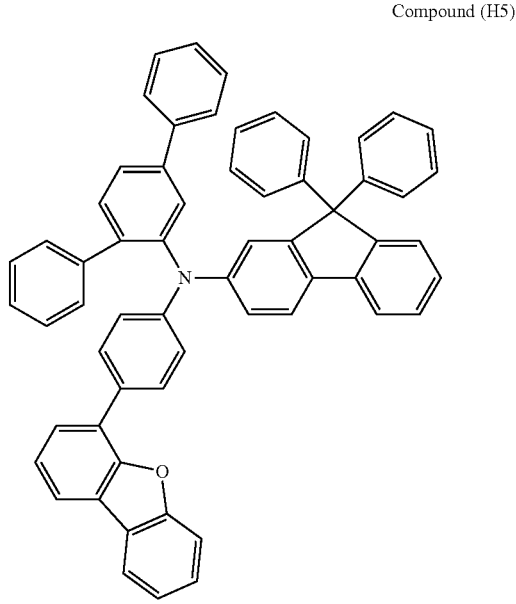 [SMILES: c1ccc(-c2ccc(-c3ccccc3)c(N(c3ccc(-c4cccc5c4oc4ccccc45)cc3)c3ccc4c(c3)C(c3ccccc3)(c3ccccc3)c3ccccc3-4)c2)cc1]

Synthesis Example 6

Production of Compound (H6)

In the same manner as in Synthesis Example 1 except for using 3.2 g of the intermediate 1-1 in place of the intermediate 1-2 and using 1.2 g of [1,1':4',1"]terphenyl-2-ylamine in place of the intermediate 2-1, 1.8 g of a white crystal was obtained, which was identified by FD-MS analysis as the following compound (H6) (yield: 50%).

Compound (H6)

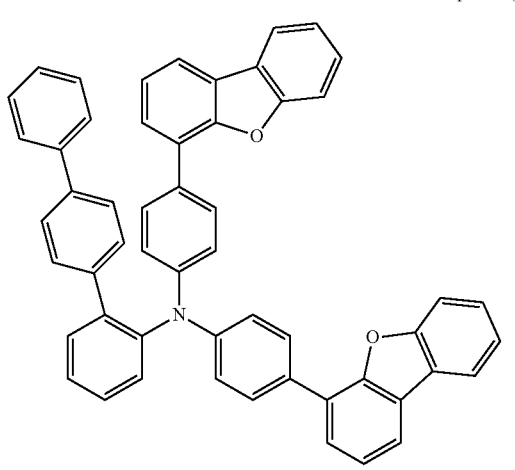

Example 1-1

Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV (ultraviolet) ozone cleaning for 30 min.

The cleaned glass substrate having a transparent electrode line was mounted to a substrate holder of a vacuum vapor deposition apparatus. First, the following acceptor material (A) was vapor-deposited so as to cover the transparent electrode to form an acceptor layer with a thickness of 5 nm.

On the acceptor layer, the following aromatic amine compound (HT1) as a first hole transporting material was vapor-deposited to form a first hole transporting layer with a thickness of 160 nm. Successively after forming the first hole transporting layer, the compound (H1) as a second hole transporting material was vapor-deposited to form a second hole transporting layer with a thickness of 10 nm.

On the second hole transporting layer, the following host material and the following dopant as fluorescent emitting materials were vapor co-deposited to form a fluorescent emitting layer with a thickness of 25 nm. The concentration of the dopant in the fluorescent emitting layer was 4% by mass.

Thereafter, on the fluorescent emitting layer, the following compound ET1, compound ET2, and Li were vapor co-deposited into a thickness of 20 nm, 10 nm, and 25 nm, respectively to form an electron transporting/injecting layer. The concentration of Li was 4% by weight. Further, metallic Al was deposited into a thickness of 80 nm to form a cathode, thereby producing an organic EL device.

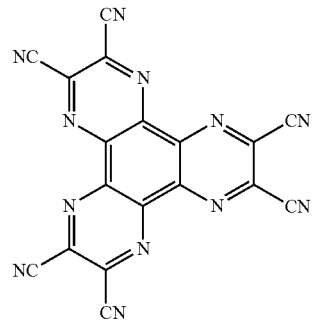

Acceptor material (A)

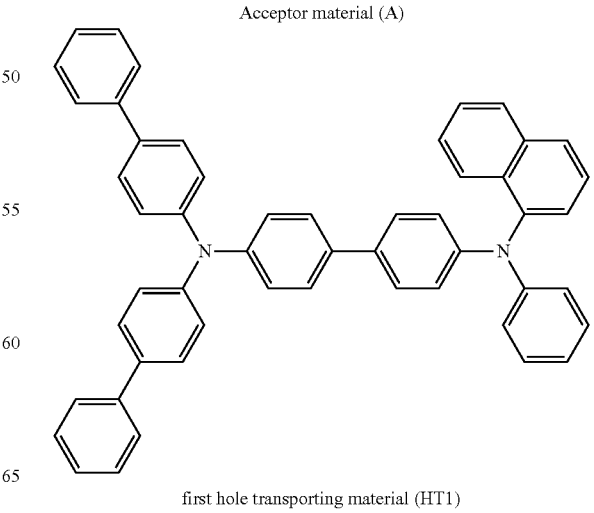

first hole transporting material (HT1)

-continued

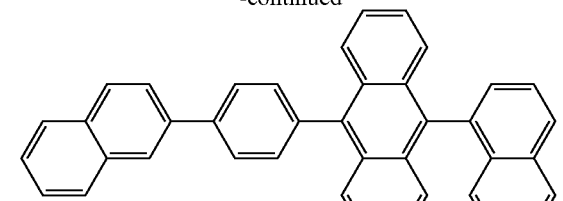

Host material

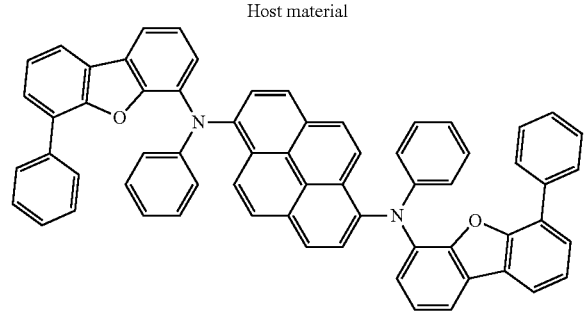

Dopant

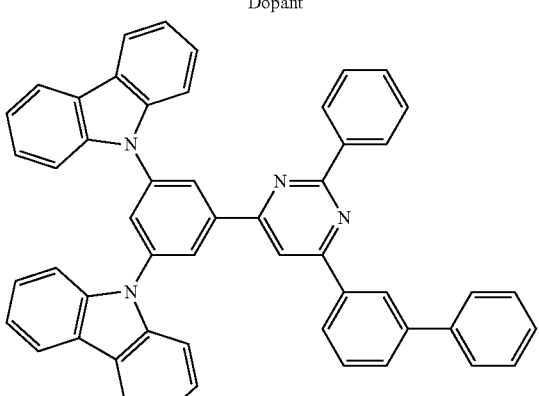

Electron transporting material (ET1)

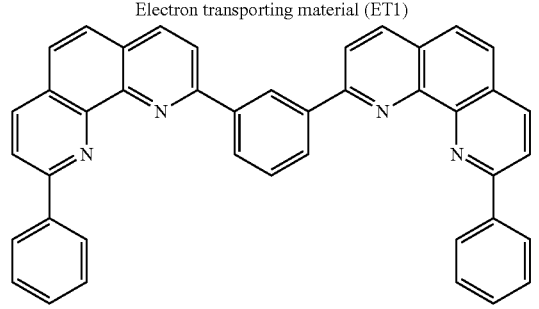

Electron transporting material (ET2)

Examples 1-2 to 1-6

Each organic EL device of Examples 1-2 to 1-6 was produced in the same manner as in Example 1-1 except for forming the second hole transporting layer by using each compound shown in Table 1 as the second hole transporting material.

Comparative Examples 1 and 2

Each organic EL device of Comparative Examples 1 and 2 was produced in the same manner as in Example 1-1 except for forming the second hole transporting layer by using the following comparative compound 1 (Comparative Example 1) or the following comparative compound 2 (Comparative Example 2) as the second hole transporting material.

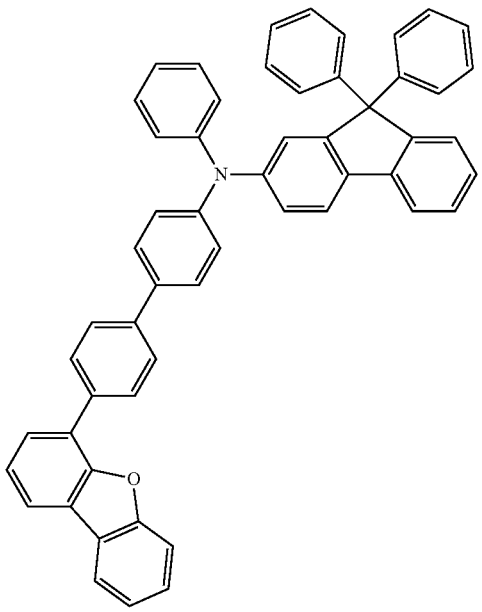

Comparative compound 1

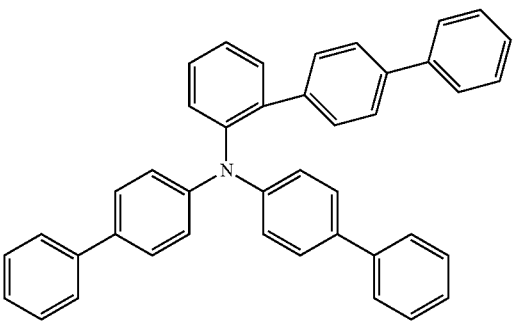

Comparative compound 2

Evaluation of Emission Performance of Organic EL Device

Each organic EL device thus produced was allowed to emit light by driving at a constant current to measure the luminance (L) and the current density. From the measured results, the emission efficiency (cd/A) and the driving voltage (V) at a current density of 10 mA/cm$^2$ were determined. In addition, the 80% lifetime was measured. The 80% lifetime is the time taken until the luminance is reduced to 80% of the initial luminance when driving at a constant current. The results are shown in Table 1.

TABLE 1

|  | Second hole transporting layer | cd/A | V | 80% lifetime (h) |
| --- | --- | --- | --- | --- |
| Example 1-1 | H1 | 6.4 | 4.3 | 200 |
| Example 1-2 | H2 | 7.2 | 4.1 | 210 |
| Example 1-3 | H3 | 6.9 | 4.2 | 240 |
| Example 1-4 | H4 | 6.8 | 4.2 | 230 |
| Example 1-5 | H5 | 6.8 | 4.3 | 200 |
| Example 1-6 | H6 | 6.9 | 4.0 | 220 |
| Comparative | Comparative | 5.5 | 4.2 | 120 |

TABLE 1-continued

| | Second hole transporting layer | cd/A | V | 80% lifetime (h) |
|---|---|---|---|---|
| example 1 | compound 1 | | | |
| Comparative example 2 | Comparative compound 2 | 1.5 | 5.0 | 80 |

As seen from Table 1, it can be found that an organic EL device having high efficiency even when driving at a low voltage and long lifetime is obtained by using each of the compounds (H1) to (H6) within formula (1).

Example 2-1

Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV (ultraviolet) ozone cleaning for 30 min.

The cleaned glass substrate having a transparent electrode line was mounted to a substrate holder of a vacuum vapor deposition apparatus. First, the following acceptor material (A) was vapor-deposited so as to cover the transparent electrode to form an acceptor layer with a thickness of 5 nm.

On the acceptor layer, the compound (H2) as a first hole transporting material was vapor-deposited to form a first hole transporting layer with a thickness of 160 nm. Successively after forming the first hole transporting layer, the following aromatic amine derivative (Y1) as a second hole transporting material was vapor-deposited to form a second hole transporting layer with a thickness of 10 nm.

On the second hole transporting layer, the following host material and the following dopant as fluorescent emitting materials were vapor co-deposited to form a fluorescent emitting layer with a thickness of 25 nm. The concentration of the dopant in the fluorescent emitting layer was 4% by mass.

Thereafter, on the fluorescent emitting layer, the following compound ET1, compound ET2, and Li were vapor co-deposited into a thickness of 20 nm, 10 nm, and 25 nm, respectively to form an electron transporting/injecting layer. The concentration of Li was 4% by weight. Further, metallic Al was deposited into a thickness of 80 nm to form a cathode, thereby producing an organic EL device.

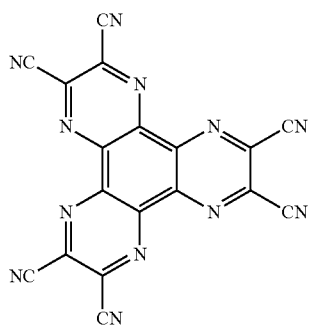

Acceptor material (A)

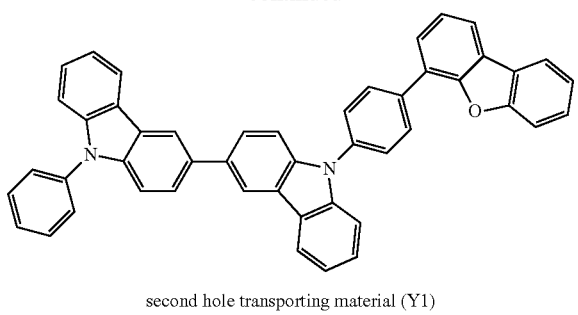

second hole transporting material (Y1)

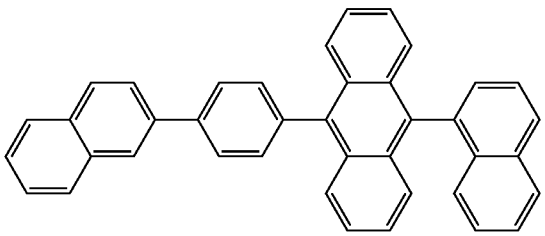

Host material

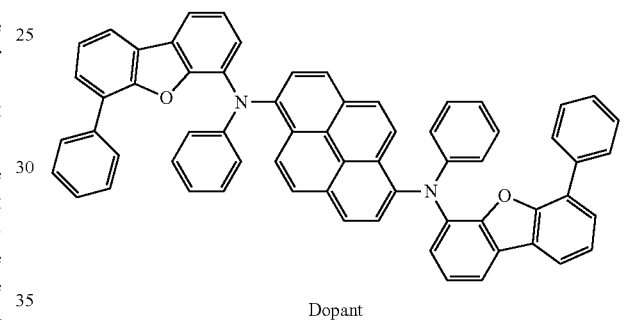

Dopant

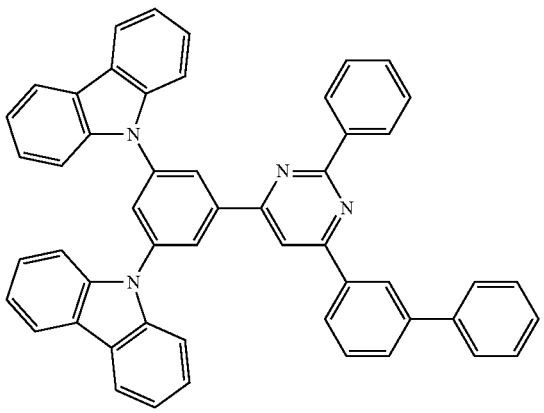

Electron transporting material (ET1)

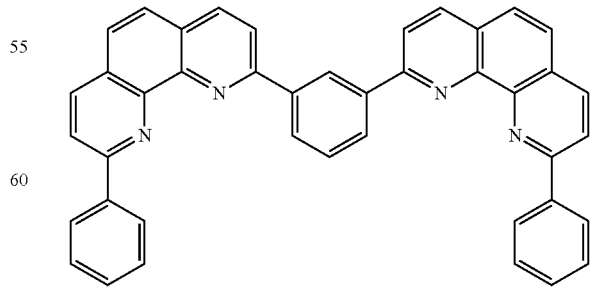

Electron transporting material (ET2)

Examples 2-2 and 2-3

Each organic EL device of Examples 2-2 and 2-3 was produced in the same manner as in Example 2-1 except for forming the first hole transporting layer by using each compound shown in Table 2 as the first hole transporting material.

Comparative Example 3

The organic EL device of Comparative Example 3 was produced in the same manner as in Example 2-1 except for forming the first hole transporting layer by using the following comparative compound 3 as the first hole transporting material.

Comparative compound 3

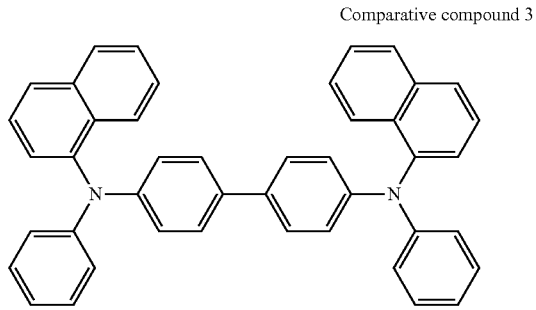 [SMILES: c1ccc(N(c2ccc(-c3ccc(N(c4ccccc4)c4cccc5ccccc45)cc3)cc2)c2cccc3ccccc23)cc1]

Evaluation of Emission Performance of Organic EL Device

Each organic EL device thus produced was measured for the emission efficiency (cd/A) and the driving voltage (V) at a current density of 10 mA/cm$^2$, and the 80% lifetime in the same manner as described above. The results are shown in Table 2.

TABLE 2

| | First hole transporting layer | cd/A | V | 80% lifetime (h) |
|---|---|---|---|---|
| Example 2-1 | H2 | 8.5 | 4.0 | 180 |
| Example 2-2 | H3 | 8.3 | 4.0 | 200 |
| Example 2-3 | H6 | 8.5 | 4.0 | 240 |
| Comparative example 3 | Comparative compound 3 | 7.2 | 4.0 | 110 |

As seen from Table 2, it can be found that an organic EL device having high efficiency even when driving at a low voltage and long lifetime is obtained by using each of the compounds (H2), (H3), and (H6) within formula (1).

What is claimed is:
1. A compound represented by formula (1),

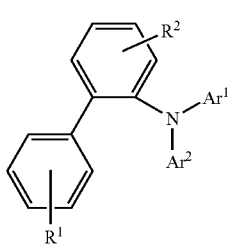

(1)

wherein:
$R^1$ represents a phenyl group, a naphthylphenyl group, a biphenylyl group, a terphenylyl group, a biphenylenyl group, a naphthyl group, or a phenylnaphthyl group;
the aryl group and a benzene ring to which $R^1$ is bonded may be crosslinked;
$R^2$ represents a hydrogen atom;
$Ar^1$ and $Ar^2$ represents a group represented by formula (3):

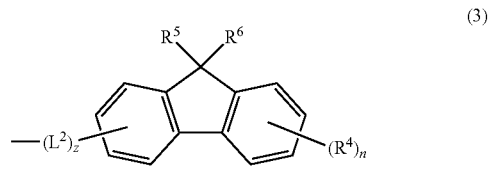

(3)

wherein:
$R^5$ and $R^6$ each independently represent an unsubstituted alkyl group having 1 to 20 carbon atoms,
$L^2$ represents a substituted or unsubstituted arylene group having 6 to 50 ring carbon atoms;
z represents 0 and $(L^2)_0$ represents a single bond;
$R^4$ represents a substituted or unsubstituted alkyl group having 1 to 20 carbon atoms or a substituted or unsubstituted aryl group having 6 to 50 ring carbon atoms;
n represents an integer of 0 to 4, when n is an integer of 2 to 4, two to four groups $R^4$ may be the same or different and may be bonded to each other to form a ring, and when n is 0, $(R^4)_0$ represents a hydrogen atom.

2. The compound according to claim 1, wherein the group of formula (1) represented by formula (4):

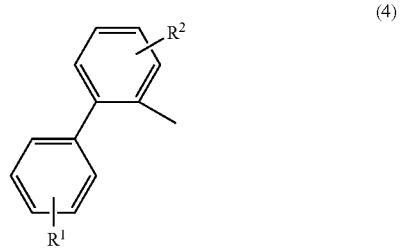

(4)

is represented by formula (4a):

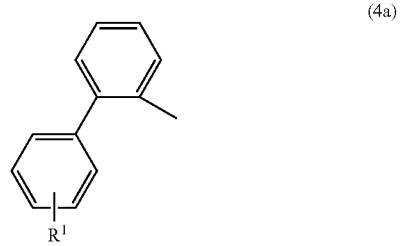

(4a)

wherein $R^1$ is as defined in formula (1).

3. The compound according to claim 1, wherein formula (3) is represented by formula (3a'):

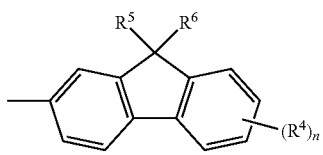

wherein $R^4$, $R^5$, $R^6$, and n are as defined in formula (1).

4. The compound according to claim 1, wherein formula (3) is represented by formula (3a''):

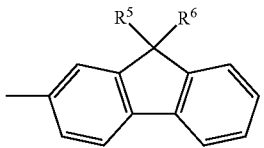

wherein $R^5$ and $R^6$ are as defined in formula (1).

5. The compound according to claim 1, wherein formula (1) is represented by formula (1a):

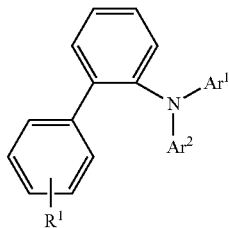

wherein $R^1$, $Ar^2$ and $Ar^2$ are as defined in formula (1).

6. The compound according to claim 1, wherein formula (1) is represented by formulae (1a-3):

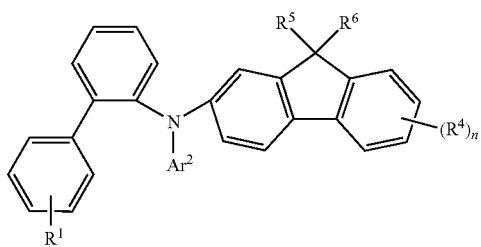

wherein $Ar^2$ represents a group represented by formula (3a'):

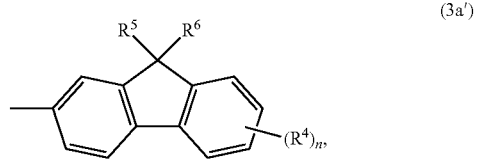

and
$R^1$, $R^4$, $R^5$, $R^6$, and n are as defined in formula 1).

7. The compound according to claim 1, wherein formula (1) is represented by formula (1a-3'):

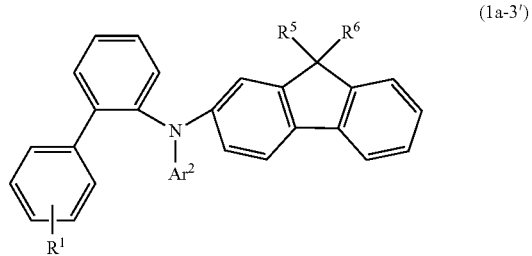

wherein $Ar^2$ represents a group represented by formula (3a''):

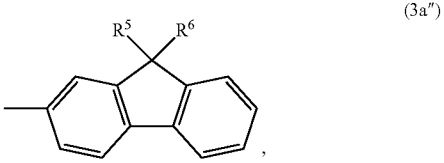

and
$R^1$, $R^5$, and $R^6$ are as defined in formula (1).

8. The compound according to claim 1, wherein $R^5$ and $R^6$ each independently represent a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, a decyl group, an undecyl group, or a dodecyl group.

9. The compound according to claim 1, wherein $R^5$ and $R^6$ each independently represent a methyl group, an ethyl group, a n-propyl group, an isopropyl group, a n-butyl group, an isobutyl group, a s-butyl group, a t-butyl group, or a pentyl group.

10. The compound according to claim 1, wherein $R^5$ and $R^6$ each independently represent a methyl group, an ethyl group, a n-propyl group, an isopropyl group, a n-butyl group, an isobutyl group, a s-butyl group, or a t-butyl group.

11. The compound according to claim 1, wherein $R^5$ and $R^6$ each independently represent a methyl group or a t-butyl group.

12. The compound according to claim 1, wherein $R^5$ and $R^6$ both represent methyl groups.

13. The compound according to claim 1, wherein $R^1$ represents a phenyl group, a naphthylphenyl group, a biphenylyl group, a terphenylyl group, a biphenylenyl group, a naphthyl group, or a phenylnaphthyl group;

R² represents a hydrogen atom;
Ar¹ and Ar² each independently represent a group represented by formula (3a')

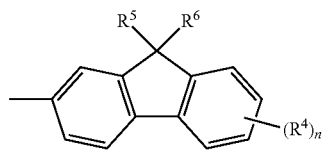

(3a')

wherein:
R⁴ represents a substituted or unsubstituted alkyl group having 1 to 20 carbon atoms or a substituted or unsubstituted aryl group having 6 to 50 ring carbon atoms;
R⁵ and R⁶ each independently represent a methyl group, an ethyl group, a n-propyl group, an isopropyl group, a n-butyl group, an isobutyl group, a s-butyl group, or a t-butyl group; and
n represents an integer of 0 to 4, when n is an integer of 2 to 4, two to four groups R⁴ may be the same or different and may be bonded to each other to form a ring, and when n is 0, (R⁴)₀ represents a hydrogen atom.

14. The compound according to claim 1, wherein R¹ represents a phenyl group, a naphthylphenyl group, a biphenylyl group, a terphenylyl group, or a phenylnaphthyl group;
R² represents a hydrogen atom;
Ar¹ and Ar² each independently represent a group represented by formula (3a'):

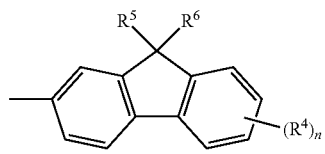

(3a')

wherein:
R⁴ represents a substituted or unsubstituted alkyl group having 1 to 20 carbon atoms or a substituted or unsubstituted aryl group having 6 to 50 ring carbon atoms;
R⁵ and R⁶ each independently represent a methyl group or a t-butyl group; and
n represents an integer of 0 to 4, when n is an integer of 2 to 4, two to four groups R⁴ may be the same or different and may be bonded to each other to form a ring, and when n is 0, (R⁴)₀ represents a hydrogen atom.

15. The compound according to claim 1, wherein
R¹ represents a biphenylyl group;
R² represents a hydrogen atom;
Ar¹ and Ar² each independently represent a group represented by formula (3a'):

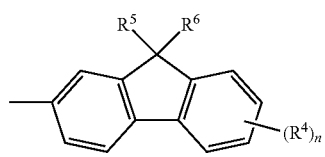

(3a')

wherein:
R⁴ represents a substituted or unsubstituted alkyl group having 1 to 20 carbon atoms or a substituted or unsubstituted aryl group having 6 to 50 ring carbon atoms;
R⁵ and R⁶ both represent methyl groups; and
n represents an integer of 0 to 4, when n is an integer of 2 to 4, two to four groups R⁴ may be the same or different and may be bonded to each other to form a ring, and when n is 0, (R⁴)₀ represents a hydrogen atom.

16. The compound according to claim 1, wherein
R¹ represents a phenyl group, a naphthylphenyl group, a biphenylyl group, a terphenylyl group, a biphenylenyl group, a naphthyl group, or a phenylnaphthyl group;
R² represents a hydrogen atom;
Ar¹ and Ar² each independently represent a group represented by formula (3a"):

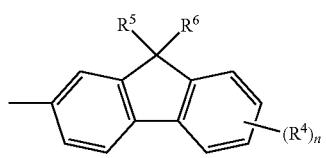

(3a")

wherein:
R⁵ and R⁶ each independently represent a methyl group, an ethyl group, a n-propyl group, an isopropyl group, a n-butyl group, an isobutyl group, a s-butyl group, or a t-butyl group.

17. The compound according to claim 1, wherein
R¹ represents a phenyl group, a naphthylphenyl group, a biphenylyl group, a terphenylyl group, or a phenylnaphthyl group;
R² represents a hydrogen atom;
Ar¹ and Ar² each independently represent a group represented by formula (3a'

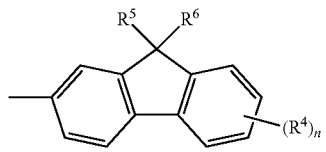

(3a")

wherein:
R⁵ and R⁶ each independently represent a methyl group or a t-butyl group.

18. The compound according to claim 1, wherein
R¹ represents a biphenylyl group;
R² represents a hydrogen atom;
Ar¹ and Ar² each independently represent a group represented by formula (3a"):

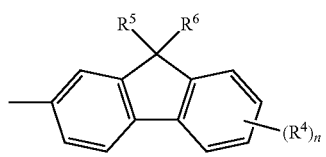

(3a")

wherein:

R⁵ and R⁶ both represent methyl groups.

19. A material for organic electroluminescence devices which comprises the compound according to claim 1.

20. An organic electroluminescence device which comprises an anode, a cathode, and at least one organic thin film layer between the anode and the cathode, wherein:

the at least one organic thin film layer comprises a light emitting layer; and at least one layer of the at least one organic thin film layer comprises the compound according to claim 1.

21. The organic electroluminescence device according to claim 20, wherein the organic electroluminescence device comprises an organic thin film layer between the anode and the light emitting layer and the organic thin film layer comprises the compound.

22. The organic electroluminescence device according to claim 21, wherein:

the organic thin film layer comprises a hole injecting layer and a hole transporting layer; and the hole injecting layer or the hole transporting layer comprises the aromatic amine derivative.

23. The organic electroluminescence device according to claim 20, wherein:

the at least one organic thin film layer comprises a hole transporting layer between the anode and the light emitting layer;

the hole transporting layer comprises a first hole transporting layer at an anode side and a second hole transporting layer at a cathode side; and any of the first hole transporting layer and the second hole transporting layer comprises the aromatic amine derivative.

24. The organic electroluminescence device according to claim 23, wherein the first hole transporting layer comprises the aromatic amine derivative.

25. The organic electroluminescence device according to claim 23, wherein the second hole transporting layer comprises the aromatic amine derivative.

26. The organic electroluminescence device according to claim 20, wherein:

the at least one organic thin film layer between the anode and the light emitting layer consists of in the order of listed:

a hole injecting layer, a first hole transporting layer at an anode side, and a second hole transporting layer at a cathode side, wherein any of the first hole transporting layer and the second hole transporting layer comprises the aromatic amine derivative.

27. The organic electroluminescence device according to claim 20, comprising, in the order listed:

the anode;

a hole injecting layer;

a hole transporting layer that consists of a first hole transporting layer at an anode side and a second hole transporting layer at a cathode side;

the light emitting layer; and the cathode;

wherein any of the first hole transporting layer and the second hole transporting layer comprises the aromatic amine derivative.

28. The organic electroluminescence device according to claim 27, wherein the first hole transporting layer comprises the aromatic amine derivative.

29. The organic electroluminescence device according to claim 27, wherein the second hole transporting layer comprises the aromatic amine derivative.

30. An electronic equipment which comprises the organic electroluminescence device according to claim 20.

* * * * *